US008722637B2

(12) United States Patent
Prabhakar

(10) Patent No.: US 8,722,637 B2
(45) Date of Patent: May 13, 2014

(54) METHODS AND COMPOSITIONS OF IG20 AND DENN-SV SPLICE VARIANTS

(75) Inventor: Bellur S. Prabhakar, Oak Brook, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1611 days.

(21) Appl. No.: 10/572,582

(22) PCT Filed: Sep. 22, 2004

(86) PCT No.: PCT/US2004/030986
§ 371 (c)(1),
(2), (4) Date: Jul. 13, 2007

(87) PCT Pub. No.: WO2005/037303
PCT Pub. Date: Apr. 28, 2005

(65) Prior Publication Data
US 2008/0233645 A1    Sep. 25, 2008

Related U.S. Application Data

(60) Provisional application No. 60/505,264, filed on Sep. 22, 2003.

(51) Int. Cl.
*C12N 15/11*     (2006.01)
*A61K 48/00*     (2006.01)

(52) U.S. Cl.
USPC ..................................... 514/44 A; 514/44 R

(58) Field of Classification Search
CPC ........... A61K 38/1709; C07K 14/4703; C07K 14/82; C07K 16/18
USPC .............................. 514/44; 435/375; 536/23.1
See application file for complete search history.

(56) References Cited

U.S. PATENT DOCUMENTS

| 2003/0162734 A1 | 8/2003 | Miller et al. | |
| 2007/0031844 A1* | 2/2007 | Khvorova et al. | 435/6 |
| 2009/0075929 A1 | 3/2009 | Prabhakar et al. | |

FOREIGN PATENT DOCUMENTS

| WO | WO 2005/037303 A1 | 4/2005 |
| WO | WO 2005037303 A1 | 4/2005 |

OTHER PUBLICATIONS

Antignani et al., "How do Bax and Bak lead to permeabilization of the outer mitochondrial membrane?," *Current Opinion in Cell Biology*, 18: 685-689 (2006).
Barber et al., "Membrane Translocation of P-Rex1 is Mediated by G Protein Betagamma Subunits and Phosphoinositide 3-Kinase," *The Journal of Biological Chemistry*, 282 (41): 29967-29976 (2007).
Bhaskar et al., "The Two TORCS and Akt," *Developmental Cell*, 12: 487-502 (2007).

Brinkman et al., "Engagement of Tumor Necrosis Factor (TNF) Receptor 1 Leads to ATF-2- and p38 Mitogen-activated Protein Kinase-dependent TNF-alpha Gene Expression," *The Journal of Biological Chemistry*, 274 (43): 30882-30886 (1999).
Brown et al., "MADD is highly homologous to a Rab3 guanine-nucleotide exchange protein (Rab3-GEP)," *Curr Biol.*, 8 (6): R191 (1998).
Brunet et al., "Akt Promotes Cell Survival by Phosphorylating and Inhibiting a Forkhead Transcription Factor," *Cell*, 96 (43): 857-868 (1999).
Chow et al., "DENN, a novel human gene differentially expressed in normal and neoplastic cells," *DNA Sequence—The Journal of Sequencing and Mapping*, 6: 263-273 (1996).
Chow et al., "The human DENN gene: genomic organization, alternative splicing, and localization to chromosome 11 p11.21-.p11.22." *Genome*, 41: 543-552 (1998).
Cuevas et al., "Role of mitogen-activated protein kinase kinase kinases in signal integration," *Oncogene*, 26: 3159-3171 (2007).
Datta et al., "Akt Phosphorylation of BAD Couples Survival Signals to the Cell-Intrinsic Death Machinery," *Cell*, 91: 231-241 (1997).
De Cesare et al., "Rsk-2 activity is necessary for epidermal growth factor-induced phosphorylation of CREB protein and transcription of c-fos gene," *Proc. Natl. Acad. Sci.*, 95: 12202-12207 (1998).
Del Villar et al., "Down Regulation of DENN/MADD, A TNF receptor binding protein, correlates with neuronal cell death in Alzheimer's disease brain and hippocampal neurons," *PNAS*, 101 (12): 4210-4215 (2004).
Dhillon et al., "MAP kinase signaling pathways in cancer," *Oncogene*, 26: 3279-3290 (2007).
Dohi et al., "Comparmentalized Phosphorylation of IAP by Protein Kinase A Regulates Cytoprotection," *Molecular Cell*, 27: 17-28 (2007).
Du et al., "Smac, a Mitochondrial Protein that Promotes Cytochrome c-Dependent Caspase Activation by Eliminating IAP Inhibition," *Cell*, 102: 33-42 (2000).
Efimova et al., "IG20, a MADD Splice Variant, Increases Cell Susceptibility to gamma-Irradiation and induces Soluble Mediators That Suppress Tumor Cell Growth," *Cancer Research*, 63: 8768-8776 (2003).
Garcia-Blanco et al., "Alternative splicing in disease and therapy," *Nature Biotechnology*, 22 (5): 535-546 (2004).
Gardai et al., "Phosphorylation of Bax Ser184 by Akt Regulates Its Activity and Apoptosis in Neutrophils," *The Journal of Biological Chemistry*, 279 (20): 21085-21095 (2004).
Goto et al., "A Novel Human Insulinoma-associated cDNA, IA-1, Encodes a Protein with "Zinc-finger" DNA-binding Motifs," *The Journal of Biological Chemistry*, 267 (21): 15252-15257 (1992).
Herdegen et al., "Inducible and constitutive transcription factors in the mammalian nervous system: control of gene expression by Jun, Fos and Krox, and CREB/ATF proteins," *Brain Research Reviews*, 28: 370-490 (1998).
Iwasaki et al., "The Rab3 GDP/GTP exchange factor homolog AEX-3 has a dual function in synaptic transmission," *The EMBO Journal*, 19 (17): 4806-4816 (2000).

(Continued)

*Primary Examiner* — Catherine Hibbert
(74) *Attorney, Agent, or Firm* — Barnes & Thornbug LLP; Alice O. Martin

(57) ABSTRACT

Methods and compositions relating to IG20 expression, splice variants of IG20, effects of endogenous DENN-SV function with respect to processes regulating cell proliferation, cell survival and cell death are disclosed.

3 Claims, 40 Drawing Sheets

(56) References Cited

OTHER PUBLICATIONS

Kalnina et al., "Alterations of Pre-mRNA Splicing in Cancer," *Genes, Chromosomes & Cancer*, 42: 342-357 (2005).
Kozielski et al., "A model of the microtubule-kinesin complex based on electron cryomicroscopy and X-ray crystallography," *Current Biology*, 8: 191-198 (1998).
Lee et al., "Interaction of HCV core protein with 14-3-3xi protein releases Bax to activate apoptosis," *Biochemical and Biophysical Research Communications*, 352: 756-762 (2007).
Levivier et al., "uDENN, DENN, and dDENN: Indissociable Domains in Rab and MAP Kinasis Signaling Pathways," *Biochemical and Biophysical Research Communications*, 287: 688-695 (2001).
Li et al., "Cytochrome c and dATP-Dependent Formation of Apaf-1/ Caspase-9 Complex Initiates and Apoptotic Protease Cascade," *Cell*, 91: 479-489 (1997).
Li et al., "p53 regulates mitochondrial membrane potential through reactive oxygen species and induces cytochrome c-independent apoptosis blocked by Bcl-2," *The EMBO Journal*, 18 (21): 6027-6036 (1999).
Li et al., "Phosphorylation by Protein Kinase CK2: A Signaling Switch for the Caspase-Inhibiting Protein ARC," *Molecular Cell*, 10: 247-258 (2002).
Lim et al., "Induction of Marked Apoptosis in Mammalian Cancer Cell Lines by Antisense DNA Treatment to Abolish Expression of DENN (Differently Expressed in Normal and Neoplastic Cells)," *Molecular Carcinogenesis*, 35: 110-126 (2002).
Lim et al., "Antisense Abrogation of DENN Expression Induces Apoptosis of Leukemia Cells in Vitro, Causes Tumor Regression In Vivo and Alters the Transcription of Genes Involved in Apoptosis and the Cell Cycle," *Int. J. Cancer*, 109: 24-37 (2004).
Liu et al., "Dissection of TNF Receptor 1 Effector Functions: JNK Activation is Not Linked to Apoptosis While NF-kappaB Activation Prevents Cell Death," *Cell*, 87: 565-576 (1996).
LoPiccolo et al., "Targeting Akt in cancer therapy," *Anti-Cancer Drugs*, 18: 861-874 (2007).
Manning et al., "AKT/PKB Signaling: Navigating Downstream," *Cell*, 129: 1261-1274 (2007).
Mayo et al., "A phosphatidylinositol 3-kinase/Akt pathway promotes translocation of Mdm2 from the cytoplasm to the nucleus," *PNAS*, 98 (20): 11598-11603 (2001).
Micheau et al., "Induction of TNF Receptor 1-Mediated Apoptosis via Two Sequential Signaling Complexes," *Cell*, 114: 181-190 (2003).
Mulherkar et al., "MADD/DENN splice variant of the *IG20* gene is necessary and sufficient for cancer cell survival," *Oncogene*, 25: 6252-6261 (2006).
Mulherkar et al., "MADD/DENN Splice Variant of the IG20 Gene is a Negative Regulator of Caspase-8 Activation," *The Journal of Biological Chemistry*, 282 (16): 11715-11721 (2007).
Murakami-Mori et al., "Implication of TNF Receptor-I-Mediated Extracellular Signal-Related Kinases 1 and 2 (ERK1/2) Activation in Growth of AIDS-Associated Kaposi's Sarcoma Cells: A Possible Role of a Novel Death Domain Protein MADD in TNF-alpha-Induced ERK1/2 Activation in Kaposi's Sarcoma Cells," *The Journal of Immunology*, 162: 3672-3679 (1999).
Nomura et al., "14-3-3 Interacts Directly with and Negatively Regulates Pro-apoptotic Bax," *The Journal of Biological Chemistry*, 278 (3): 2058-2065 (2003).
Ottmann et al., "Phosphorylation-independent interaction between 14-3-3 and endoenzyme S: from structure to pathogenesis," *The EMBO Journal*, 26: 902-913 (2007).
Pan et al., "The Receptor for the Cytotoxic Ligand TRAIL," *Science*, 276: 111-113 (1997).
Ramaswamy et al., "IG20 (MADD splice variant-5), a proapoptotic protein, interacts with DR4/DR5 and enhances TRAIL-induced apoptosis by increasing recruitment of FADD and caspase-8 to the DISC," *Oncogene*, 23: 6083-6094 (2004).
Shumueli et al., "Mdm2: p53's Lifesaver?," *Molecular Cell*, 25: 794-795 (2007).
Susin et al., "Molecular characterization of mitochondrial apoptosis-inducing factor," *Nature*, 397: 441-446 (1999).
Tanaka et al., "Role of Rab3 GDP/GTP Exchange Protein in Synaptic Vesicle Trafficking at the Mouse Neuomuscular Junction," *Molecular Biology of the Cell*, 12: 1421-1430 (2001).
Telliez et al., "LRDD, a novel leucine rich repeat and death domain containing protein," *Biochimica et Biophysica Acta*, 1478: 280-288 (2000).
Thornberry et al., "Caspases: Enemies Within," *Science*, 281: 1312-1316 (1998).
Tsuruta et al., "JNK promotes Bax translocation to mitochondria through phosphorylation of 14-3-3 proteins," *The EMBO Journal*, 23 (8): 1889-1899 (2004).
Venables, "Aberrant and Alternative Splicing in Cancer," *Cancer Research*, 64: 7647-7654 (2004).
Verhagen et al., "Identification of DIABLO, a Mammalian Protein that Promotes Apoptosis by Binding to and Antagonizing IAP Proteins," *Cell*, 102: 43-53 (2000).
Wada et al., "Isolation and Characterization of a GDP/GTP Exchange Protein Specific for the Rab3 Subfamily Small G Proteins," *The Journal of Biological Chemistry*, 272 (7): 3875-3878 (1997).
Xin et al., "Nicotine Inactivation of the Proapoptotic Function of Bax through Phophorylation," *The Journal of Biological Chemistry*, 280 (11): 10781-10789 (2005).
Yamaguchi et al., "The protein kinase PKB/Akt regulates cell survival and apoptosis by inhibiting Bax conformational change," *Oncogene*, 20: 7779-7786 (2001).
Yamaguchi et al., "A GDP/GTP exchange protein for the Rab3 small G protein family up-regulates a postdocking step of synaptic exocytosis in central synapses," *PNAS*, 99 (22): 14536-14541 (2002).
Zha et al., "Serine Phosphorylation of Death Agonist BAD in Response to Survival Factor Results in Binding to 14-3-3 Not BCX-XL," *Cell*, 87: 619-628 (1996).
Zhai et al., "Identification of a Novel Interaction of 14-3-3 with 190RhoGEF," *The Journal of Biological Chemistry*, 276 (44): 41318-41324 (2001).
Zhang et al., "Mechanisms of resistance to TRAIL-induced apoptosis in cancer," *Cancer Gene Therapy*, 12: 228-237 (2005).
Zhou et al., "HER-2/neu induces p53 ubiquitination via Akt-mediated MDM2 phosphorylation," *Nature Cell Biology*, 3: 973-982 (2001).
International Search Report issued in PCT/US2004/030986 (2005).
International Search Report issued in PCT/US2007/060712 (2007).
Al-Zoubi et al., "Contrasting Effects of IG20 and its Splice Isoforms, MADD and DENN-SV, on Tumor Necrosis Factor α-induced Apoptosis and Activation of Caspase-8 and -3," *Jrnl. of Biological Chem.*, 276:50 47202-47211 (2001).
Efimova et al., "Differential Effects of IG20 and Its Splice Isoform, DENN-SV, on Cell Proliferation and Apoptosis," *FASEB Jrnl.*, 16:5 A1083 (2002).
Efimova et al., "IG20, in contrast to DENN-SV, (MADD splice variants) suppresses tumor cell survival, and enhances their susceptibility to apoptosis and cancer drugs," *Oncogene*, 23:5 1076-1087 (2004).
Hilger et al., "The Ras-Raf-MEK-ERK Pathway in the Treatment of Cancer," *Onkologie*, 25:6 511-518 (2002).
Schievella et al., "MADD, a Novel Death Domain Protein That Interacts with the Type 1 Tumor Necrosis Factor Receptor and Activates Mitogen-Activated Protein Kinase," *Jrnl. of Biological Chem.*, 272:18 12069-12075 (1997).
Zhang et al., "A splicing variant of a death domain protein that is regulated by a mitogen-activated kinase is a substrate for c-Jun N-terminal kinase in the human central nervous system," *Proc. Natl. Acad. Sci. USA*, 95: 2586-2591 (1998).
Li et al., "Regulation of Apoptosis and Caspace-8 Expression in Neuroblastoma Cells by Isoforms of the *IG20* Gene," *DDT*, 68 (18): 912-917 (2008).
Thompson, "Applications of antisense and siRNAs during preclinical drug development," *Cancer Res.*, 7 (17): 7352-7361 (2002).
International Search Report issued in PCT/US2009/050219 (2010).

\* cited by examiner

A

B

C

D

A

B

A

B

C

D

E

A

B

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtaccagctt cagtctttc                                              19

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgggactctg actccgaacc tac                                         23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcggttcagc ttgctcagga c                                           21

<210> SEQ ID NO 4
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aagtgccaca ggaaagggtc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgcgctgatc tgggactttt                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agccatgcat aaaggagaag                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtcccataa agtagaacgc                                              20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgcaggtga ccctggaagg gatc                                         24

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtacccggg tcagctagag acaggcc                                      27

<210> SEQ ID NO 10
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 10

Leu Glu Thr Asp
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Glu Val Asp
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu His Asp
1

<210> SEQ ID NO 13
<211> LENGTH: 6002
<212> TYPE: DNA
<213> ORGANISM: Homo sapiens

<400> SEQUENCE: 13
cacgtgcatg tgtagcatgc cttggttttt cctttggcat ctgaaaaagg cacaacctga     60
aagacctaga acccagtgtc ggtccccagg ccctttggga caggaagaga agagccgtgt    120
ggccgcgggg aggatgtcct gcggcgggc tgtcctcgcg gactgactgg actccatctc    180
ccagcgggcg ccgcggcgcg gccacgcccc cccactcccc gcgcgcgccc ggtgagact    240 tcgattttca gaattcctcc tgggaatgct gactccttgc ttggtgccct gatgcttctc    300
tgagataaac tgatgaattg gaaccatggt gcaaaagaag aagttctgtc ctcggttact    360
tgactatcta gtgatcgtag gggccaggca cccgagcagt gatagcgtgg cccagactcc    420
tgaattgcta cggcgatacc ccttggagga tcacactgag tttcccctgc ccccagatgt    480
agtgttcttc tgccagcccg agggctgcct gagcgtgcgg cagcggcgca tgagccttcg    540
ggatgatacc tcttttgtct tcaccctcac tgacaaggac actggagtca cgcgatatgg    600
catctgtgtt aacttctacc gctccttcca aaagcgaatc tctaaggaga aggggaagg    660 tggggcaggg tcccgtggga aggaaggaac ccatgccacc tgtgcctcag aagagggtgg    720
cactgagagc tcagagagtg gctcatccct gcagcctctc agtgctgact ctaccccctga   780 tgtgaaccag tctcctcggg gcaaacgccg ggccaaggcg gggagccgct cccgcaacag    840
tactctcacg tccctgtgcg tgctcagcca ctaccctttc ttctccacct tccgagagtg    900
tttgtatact ctcaagcgcc tggtggactg ctgtagtgag cgccttctgg gcaagaaact    960
gggcatccct cgaggcgtac aaagggacac catgtggcgg atcttactg gatcgctgct   1020 ggtagaggag aagtcaagtg cccttctgca tgaccttcga gagattgagg cctggatcta   1080
```

```
tcgattgctg cgctccccag tacccgtctc tgggcagaag cgagtagaca tcgaggtcct   1140
accccaagag ctccagccag ctctgacctt tgctcttcca gacccatctc gattcaccct   1200
agtggatttc ccactgcacc ttcccttgga acttctaggt gtggacgcct gtctccaggt   1260
gctaacctgc attctgttag agcacaaggt ggtgctacag tcccgagact acaatgcact   1320
ctccatgtct gtgatggcat cgtggcaat gatctaccca ctggaatata tgtttcctgt   1380
catcccgctg ctacccacct gcatggcatc agcagagcag ctgctgttgg ctccaacccc   1440
gtacatcatt ggggttcctg ccagcttctt cctctacaaa ctggacttca aaatgcctga   1500
tgatgtatgg ctagtggatc tggacagcaa tagggtgatt gccccacca atgcagaagt   1560 gctgcctatc ctgccagaac cagaatcact agagctgaaa aagcatttaa agcaggcctt   1620
ggccagcatg agtctcaaca cccagcccat cctcaatctg gagaaatttc atgagggcca   1680
ggagatcccc cttctcttgg aaggccttc taatgacctg cagtccacac cgtccactga   1740
attcaaccca ctcatctatg caatgatgt ggattctgtg gatgttgcaa ccagggttgc   1800
catggtacgg ttcttcaatt ccgccaacgt gctgcaggga tttcagatgc acacgcgtac   1860
cctgcgcctc tttcctcggc ctgtggtagc ttttcaagct ggctccttc tagcctcacg   1920 tccccggcag actccttttg ccgagaaatt ggccaggact caggctgtgg agtactttgg   1980
ggaatggatc cttaaccccca ccaactatgc ctttcagcga attcacaaca atatgtttga   2040
tccagccctg attggtgaca agccaaagtg gtatgctcat cagctgcagc ctatccacta   2100
tcgcgtctat gacagcaatt cccagctggc tgaggccctg agtgtaccac cagagcggga   2160
ctctgactcc gaacctactg atgatagtgg cagtgatagt atggattatg acgattcaag   2220
ctcttcttac tcctcccttg gtgactttgt cagtgaaatg atgaaatgtg acattaatgg   2280
tgatactccc aatgtggacc ctctgacaca tgcagcactg ggggatgcca gcgaggtgga   2340
gattgacgag ctgcagaatc agaaggaagc agaagagcct ggcccagaca gtgagaactc   2400
tcaggaaaac ccccactgc gctccagctc tagcaccaca gccagcagca gccccagcac   2460
tgtcatccac ggagccaact ctgaacctgc tgactctacg gagatggatg ataaggcagc   2520
agtaggcgtc tccaagcccc tcccttccgt gcctcccagc attggcaaat cgaacatgga   2580
cagacgtcag gcagaaattg gagaggggtc agtgcgccgg cgaatctatg acaatccata   2640
cttcgagccc caatatggct ttccccctga ggaagatgag gatgagcagg gggaaagtta   2700
cactccccga ttcagccaac atgtcagtgg caatcgggct caaaagctgc tgcggcccaa   2760
cagcttgaga ctggcaagtg actcagatgc agagtcagac tctcgggcaa gctctcccaa   2820
ctccaccgtc tccaacacca gcaccgaggg cttcggggc atcatgtctt ttgccagcag   2880
cctctatcgg aaccacagta ccagcttcag tctttcaaac ctcacactgc ccaccaaagg   2940
tgcccgagag aaggccacgc ccttcccccag tctgaaagga acaggaggg cgttagtgga   3000 tcagaagtca tctgtcatta aacacagccc aacagtgaaa agagaacctc catcaccca   3060 gggtcgatcc agcaattcta gtgagaacca gcagttcctg aaggaggtgg tgcacagcgt   3120 gctgacggc cagggagttg gctggctcaa catgaaaaag gtgcgccggc tgctggagag   3180
cgagcagctg cgagtctttg tcctgagcaa gctgaaccgc atggtgcagt cagaggacga   3240
tgcccggcag gacatcatcc cggatgtgga gatcagtcgg aaggtgtaca agggaatgtt   3300
agacctcctc aagtgtacag tcctcagctt ggagcagtcc tatgcccacg cgggtctggg   3360
tggcatggcc agcatctttg gcttttgga gattgcccag acccactact atagtaaaga   3420
accagacaag cggaagagaa gtccaacaga aagtgtaaat accccagttg gcaaggatcc   3480
```

```
tggcctagct gggcgggggg acccaaaggc tatggcacaa ctgagagttc cacaactggg    3540
acctcgggca ccaagtgcca caggaaaggg tcctaaggaa ctggacacca gaagtttaaa    3600
ggaagaaaat tttatagcat ctattgggcc tgaagtaatc aaacctgtct ttgacccttgg   3660
tgagacagag gagaaaaagt cccagatcag cgcagacagt ggtgtgagcc tgacgtctag    3720
ttcccagagg actgatcaag actctgtcat cggcgtgagt ccagctgtta tgatccgcag    3780
ctcaagtcag gattctgaag ttagcaccgt ggtgagtaat agctctggag agacccttgg    3840
agctgacagt gacttgagca gcaatgcagg tgatggacca ggtggcgagg gcagtgttca    3900
cctggcaagc tctcggggca ctttgtctga tagtgaaatt gagaccaact ctgccacaag    3960
caccatcttt ggtaaagccc acagcttgaa gccaagcata aaggagaagc tggcaggcag    4020
ccccattcgt acttctgaag atgtgagcca gcgagtctat ctctatgagg gactcctagg    4080
caaagagcgt tctactttat gggaccaaat gcaattctgg gaagatgcct tcttagatgc    4140
tgtgatgttg gagagagaag ggatgggtat ggaccagggt ccccaggaaa tgatcgacag    4200
gtacctgtcc cttggagaac atgaccggaa gcgcctggaa gatgatgaag atcgcttgct    4260
ggccacactt ctgcacaacc tcatctccta catgctgctg atgaaggtaa ataagaatga    4320
catccgcaag aaggtgaggc gcctaatggg aaagtcgcac attgggcttg tgtacagcca    4380
gcaaatcaat gaggtgcttg atcagctggc gaacctgaat ggacgcgatc tctctatctg    4440
gtccagtggc agccggcaca tgaagaagca gacatttgtg gtacatgcag gacagatac    4500
aaacggagat atcttttttca tggaggtgtg cgatgactgt gtggtgttgc gtagtaacat    4560
cggaacagtg tatgagcgct ggtggtacga gaagctcatc aacatgacct actgtcccaa    4620
gacgaaggtg ttgtgcttgt ggcgtagaaa tggctctgag acccagctca acaagttcta    4680
tactaaaaag tgtcgggagc tgtactactg tgtgaaggac agcatggagc gcgctgccgc    4740
ccgacagcaa agcatcaaac ccggacctga attgggtggc gagttccctg tgcaggacct    4800
gaagactggt gagggtggcc tgctgcaggt gaccctggaa gggatcaacc tcaaattcat    4860
gcacaatcag gttttcatag agctgaatca cattaaaaag tgcaatacag ttcgaggcgt    4920
ctttgtcctg gaggaatttg ttcctgaaat taaagaagtg gtgagccaca agtacaagac    4980
accaatggcc cacgaaatct gctactccgt attatgtctc ttctcgtacg tggctgcagt    5040
tcatagcagt gaggaagatc tcagaacccc gccccggcct gtctctagct gatggagagg    5100
ggctacgcag ctgccccagc ccagggcacg cccctggccc cttgctgttc ccaagtgcac    5160
gatgctgctg tgactgagga gtggatgatg ctcgtgtgtc ctctgcaagc cccctgctgt    5220
ggcttggttg gttaccggtt atgtgtccct ctgagtgtgt cttgagcgtg tccaccttct    5280
ccctctccac tcccagaaga ccaaactgcc ttcccctcag ggctcaagaa tgtgtacagt    5340
ctgtggggcc ggtgtgaacc cactattttg tgtccttgag acatttgtgt tgtggttcct    5400
tgtccttgtc cctggcgtta taactgtcca ctgcaagagt ctggctctcc cttctctgtg    5460
acccggcatg actgggcgcc tggagcagtt tcactctgtg aggagtgagg gaaccctggg    5520
gctcaccctc tcagaggaag ggcacagaga ggaagggaag aattgggggg cagccggagt    5580
gagtggcagc ctcccctgctt ccttctgcat tcccaagccg gcagctactg cccagggccc    5640
gcagtgttgg ctgctgcctg ccacagcctc tgtgactgca gtggagcggc gaattccctg    5700
tggcctgcca cgccttcggc atcagaggat ggagtggtcg aggctagtgg agtcccaggg    5760
accgctggct gctctgcctg agcatcaggg aggggggcagg aaagaccaag ctgggtttgc    5820
acatctgtct gcaggctgtc tctccaggca cggggtgtca ggagggagag acagcctggg   5880
```

| | |
|---|---|
| tatgggcaag aaatgactgt aaatatttca gccccacatt atttatagaa aatgtacagt | 5940 |
| tgtgtgaatg tgaaataaat gtcctcaact cccaaaaaaa aaaaaaaaaa aaaaaaaaaa | 6000 |
| aa | 6002 |

```
<210> SEQ ID NO 14
<211> LENGTH: 5689
<212> TYPE: DNA
<213> ORGANISM: Homo sapiens

<400> SEQUENCE: 14
```

| | |
|---|---|
| cccgctgccc aggattggta gactccaccg ctcggcagcc ggcttccctg ctcggacgcc | 60 |
| gagcaccgcc aaagcgcact tcgattttca gaattcctcc tgggaatgct gactccttgc | 120 |
| ttggtgccct gatgcttctc tgagataaac tgatgaattg gaaccatggt gcaaagaaag | 180 |
| aagttctgtc ctcggttact tgactatcta gtgatcgtag gggccaggca cccgagcagt | 240 |
| gatagcgtgg cccagactcc tgaattgcta cggcgatacc ccttggagga tcacactgag | 300 |
| tttcccctgc ccccagatgt agtgttcttc tgccagcccg agggctgcct gagcgtgcgg | 360 |
| cagcggcgca tgagccttcg ggatgatacc tcttttgtct tcaccctcac tgacaaggac | 420 |
| actggagtca cgcgatatgg catctgtgtt aacttctacc gctccttcca aaagcgaatc | 480 |
| tctaagggga aggggaagg tggggcaggg tcccgtggga aggaaggaac ccatgccacc | 540 |
| tgtgcctcag aagagggtgg cactgagagc tcagagagtg gctcatccct gcagcctttc | 600 |
| agtgctgact ctaccccctga tgtgaaccag tctcctcggg gcaaacgccg ggccaaggcg | 660 |
| gggagccgct cccgcaacag tactctcacg tccctgtgcg tgctcagcca ctacccttc | 720 |
| ttctccacct tccgagagtg tttgtatact ctcaagcgcc tggtggactg ctgtagtgag | 780 |
| cgccttctgg gcaagaaact gggcatccct cgaggcgtac aaagggacac catgtggcgg | 840 |
| atctttactg gatcgctgct ggtagaggag aagtcaagtg cccttctgca tgaccttcga | 900 |
| gagattgagg cctggatcta tcgattgctg cgctccccag tacccgtctc tgggcagaag | 960 |
| cgagtagaca tcgaggtcct accccaagag ctccagccag ctctgacctt tgctcttcca | 1020 |
| gacccatctc gattcaccct agtggatttc ccactgcacc ttcccttgga acttctaggt | 1080 |
| gtggacgcct gtctccagtt gctaacctgc attctgttag agcacaaggt ggtgctacag | 1140 |
| tcccgagact acaatgcact ctccatgtct gtgatggcat tcgtggcaat gatctaccca | 1200 |
| ctggagtata tgtttcctgt catcccgctg ctacccacct gcatggcatc agcagagcag | 1260 |
| ctgctgttgg ctccaacccc gtacatcatt ggggttcctg ccagcttctt cctctacaaa | 1320 |
| ctggacttca aaatgcctga tgatgtatgg ctagtggatc tggacagcaa tagggtgatt | 1380 |
| gccccccacca atgcagaagt gctgcctatc ctgccagaac cagaatcact agagctgaaa | 1440 |
| aagcatttaa agcaggcctt ggccagcatg agtctcaaca cccagcccat cctcaatctg | 1500 |
| gagaaatttc atgagggcca ggagatcccc cttctcttgg gaaggccttc taatgacctg | 1560 |
| cagtccacac cgtccactga attcaaccca ctcatctatg caatgatgc ggattctgtg | 1620 |
| gatgttgcaa ccagggttgc catggtacgg ttcttcaatt ccgccaacgt gctgcaggga | 1680 |
| tttcagatgc acacgcgtac cctgcgcctc tttcctcggc ctgtggtagc ttttcaagct | 1740 |
| ggctcctttc tagcctcacg tccccggcag actccttttg ccgagaaatt ggccaggact | 1800 |
| caggctgtgg agtactttgg ggaatggatc cttaacccca ccaactatgc ctttcagcga | 1860 |
| attcacaaca atatgtttga tccagccctg attggtgaca agccaaagtg gtatgctcat | 1920 |
| cagctgcagc ctatccacta tcgcgtctat gacagcaatt cccagctggc tgaggccctg | 1980 |

```
agtgtaccac cagagcggga ctctgactcc gaacctactg atgatagtgg cagtgatagt    2040
atggattatg acgattcaag ctcttcttac tcctcccttg gtgactttgt cagtgaaatg    2100
atgaaatgtg acattaatgg tgatactccc aatgtggacc ctctgacaca tgcagcactg    2160
ggggatgcca gcgaggtgga gattgacgag ctgcagaatc agaaggaagc agaagagcct    2220
ggcccagaca gtgagaactc tcaggaaaac cccccactgc gctccagctc tagcaccaca    2280
gccagcagca gccccagcac tgtcatccac ggagccaact ctgaacctgc tgactctacg    2340
gagatggatg ataaggcagc agtaggcgtc tccaagcccc tcccttccgt gcctcccagc    2400
attggcaaat cgaacgtgga cagacgtcag gcagaaattg agaggggggc tcaaaagctg    2460
ctgcggccca cagcttgag actggcaagt gactcagatg cagagtcaga ctctcgggca    2520
agctctccca actccaccgt ctccaacacc agcaccgagg gcttcggggg catcatgtct    2580
tttgccagca gcctctatcg gaaccacagt accagcttca gtctttcaaa cctcacactg    2640
cccaccaaag gtgcccgaga aaggccacg cccttcccca gtctgaaagg aaacaggagg    2700
gcgttagtgg atcagaagtc atctgtcatt aaacacagcc caacagtgaa aagagaacct    2760
ccatcacccc agggtcgatc cagcaattct agtgagaacc agcagttcct gaaggaggtg    2820
gtgcacagcg tgctggacgg ccagggagtt ggctggctca acatgaaaaa ggtgcgccgg    2880
ctgctggaga gcgagcagct gcgagtcttt gtcctgagca gctgaaccg catggtgcag    2940 tcagaggacg atgcccggca ggacatcatc ccggatgtgg agatcagtcg aaggtgtac    3000 aagggaatgt tagacctcct caagtgtaca gtcctcagct tggagcagtc ctatgcccac    3060
gcgggtctgg gtggcatggc cagcatcttt gggcttttgg agattgccca gacccactac    3120
tatagtaaag aaccagacaa gcggaagaga agtccaacag aaagtgtaaa taccccagtt    3180
ggcaaggatc ctggcctagc tgggcgggg gacccaaagg ctatggcaca actgagagtt    3240
ccacaactgg gacctcgggc accaagtgcc acaggaaagg gtcctaagga actggacacc    3300
agaagtttaa aggaagaaaa ttttatagca tctattgggc ctgaagtaat caaacctgtc    3360
tttgaccttg gtgagacaga ggagaaaaag tcccagatca gcgcagacag tggtgtgagc    3420
ctgacgtcta gttcccagag gactgatcaa gactctgtca tcggcgtgag tccagctgtt    3480
atgatccgca gctcaagtca ggattctgaa gttagcaccg tggtgagtaa tagctctgga    3540
gagacccttg gagctgacag tgacttgagc agcaatgcag gtgatggacc aggtggcgag    3600
ggcagtgttc acctggcaag ctctcggggc actttgtctg atagtgaaat tgagaccaac    3660
tctgccacaa gcaccatctt tggtaaagcc cacagcttga agccatgcat aaaggagaag    3720
ctggcaggca gccccattcg tacttctgaa gatgtgagcc agcgagtcta tctctatgag    3780
ggactcctag gcaaagagcg ttctacttta tgggaccaaa tgcaattctg ggaagatgcc    3840
ttcttagatg ctgtgatgtt ggagagagaa gggatgggta tggaccaggg tcccaggaa    3900 atgatcgaca ggtacctgtc ccttggagaa catgaccgga gcgcctgga agatgatgaa    3960 gatcgcttgc tggccacact tctgcacaac ctcatctcct acatgctgct gatgaaggta    4020
aataagaatg acatccgcaa gaaggtgagg cgcctaatgg gaaagtcgca cattgggctt    4080
gtgtacagcc agcaaatcaa tgaggtgctt gatcagctgg cgaacctgaa tggacgcgat    4140
ctctctatct ggtccagtgg cagccggcac atgaagaagc agacatttgt ggtacatgca    4200
gggacagata caaacggaga tatctttttc atggaggtgt gcgatgactg tgtggtgttg    4260
cgtagtaaca tcggaacagt gtatgagcgc tggtggtacg agaagctcat caacatgacc    4320
tactgtccca agacgaaggt gttgtgcttg tggcgtagaa atggctctga gacccagctc    4380
```

```
aacaagttct atactaaaaa gtgtcgggag ctgtactact gtgtgaagga cagcatggag    4440
cgcgctgccg cccgacagca aagcatcaaa cccggacctg aattgggtgg cgagttccct    4500
gtgcaggacc tgaagactgg tgagggtggc ctgctgcagg tgaccctgga agggatcaac    4560
ctcaaattca tgcacaatca ggttttcata gagctgaatc acattaaaaa gtgcaataca    4620
gttcgaggcg tctttgtcct ggaggaattt gttcctgaaa ttaaagaagt ggtgagccac    4680
aagtacaaga caccaatggc ccacgaaatc tgctactccg tattatgtct cttctcgtac    4740
gtggctgcag ttcatagcag tgaggaagat ctcagaaccc cgccccggcc tgtctctagc    4800
tgatggagag gggctacgca gctgcccag cccagggcac gcccctggcc ccttgctgtt     4860
cccaagtgca cgatgctgct gtgactgagg agtggatgat gctcgtgtgt cctctgcaac    4920
ccccctgctg tggcttggtt ggttaccggt tatgtgtccc tctgagtgtg tcttgagcgt    4980
gtccaccttc tccctctcca ctcccagaag accaaactgc cttcccctca gggctcaaga    5040
atgtgtacag tctgtggggc cggtgtgaac ccactatttt gtgtccttga gacatttgtg    5100
ttgtggttcc ttgtccttgt ccctggcgtt ataactgtcc actgcaagag tctggctctc    5160
ccttctctgt gacccggcat gactgggcgc ctggagcagt tcactctgtg aggagtgagg    5220
gaaccctggg gctcaccctc tcagaggaag ggcacagaga ggaagggaag aattgggggg    5280
cagccggagt gagtggcagc ctccctgctt ccttctgcat tcccaagccg gcagccactg    5340
cccagggccc gcagtgttgg ctgctgcctg ccacagcctc tgtgactgca gtggagcggc    5400
gaattccctg tggcctgcca cgccttcggc atcagaggat ggagtggtcg aggctagtgg    5460
agtcccaggg accgctggct gctctgcctg agcatcaggg aggggcagg aaagaccaag     5520 ctgggtttgc acatctgtct gcaggctgtc tctccaggca cggggtgtca ggagggagag    5580
acagcctggg tatgggcaag aaatgactgt aaatatttca gccccacatt atttatagaa    5640
aatgtacagt tgtgtgaatg tgaaataaat gtcctcaatt cccaaaaaa                5689
```

METHODS AND COMPOSITIONS OF IG20 AND DENN-SV SPLICE VARIANTS

SEQUENCE LISTING

The instant application contains a Sequence Listing which has been submitted electronically in ASCII format, created on Nov. 13, 2013, and is named 103049_Amd_SEQ.txt.

BACKGROUND

This application claims priority from copending PCT application PCT/US2004/030986 filed Sep. 9, 2004 and U.S. 60/505,264 filed Sep. 22, 2003. Methods and compositions of multiple splice variants of IG20 are useful to regulate cell death and replication.

Eukaryotes have evolved the process of alternative mRNA splicing for generating multiple protein isoforms from the same gene. It is a highly regulated process that ensures removal of nucleotides at specific locations without disrupting the open reading frame. Alternative mRNA splicing could remove either a whole exon or part of an exon resulting in different transcripts capable of encoding related, but distinct, proteins. Since the completion of the human genome sequencing, it has become apparent that the biological complexity seen in humans, relative to other lower species, is most likely due to a higher degree of alternative splicing in human genes. IG20 is one such gene that undergoes alternative mRNA splicing resulting in the production of multiple proteins.

cDNAs, including that encoding IG20 are differentially expressed in human insulinomas. cDNAs encoding MADD/DENN (MAP Kinase-Activating Death Domain-containing protein/Differentially Expressed in Normal and Neoplastic cells), KIAA0368 and DENN-SV (a short variant of DENN-SV) have near identical sequences, yet different actions.

Over-expression of MADD can enhance MAPK and both ERK and JNK activity, and lead to the phosphorylation of cPLA2 upon TNFα treatment. Additionally, MADD can induce TNFα gene expression and promote TNFα-induced proliferation of Kaposi's sarcoma (KS) cells, which can be inhibited by blocking MADD transcription. The GDP-GTP exchange protein (GEP), a rat homolog of IG20, mediates conversion of GDP-bound inactive form of the Rab-3 subfamily of small G proteins into the GTP-bound active form. Characterization of Rab3 GEP knockout mice showed that the protein is required for vesicle trafficking at the neuromuscular junction and might play a role in the formation of synaptic vesicles Rab3 GEP−/− mice fully develop but die shortly after birth. A related gene with minimal sequence homology to MADD is the AEX gene of the C. elegans. When the above human cDNAs were identified it was not apparent whether they represented products of related but distinct genes or different splice variants arising from a single gene.

Expression studies and sequence comparisons between cDNAs and with human genome data base showed that the above mentioned human cDNAs are splice variants encoded by the IG20 gene. The IG20 gene consists of 36 exons that range in size from 47 to 986 nucleotides, including the 5' and 3' un-translated regions. The IG20 splice variants result from alternative splicing of only exons 13L, 16, 21, 26, and 34. Human genome sequencing has revealed that the biological complexity seen in humans, relative to other species, is due to a higher degree of alternative splicing in human genes that could result in multiple proteins with different functions from the same gene.

In an attempt to understand the functional relevance of different splice variants of IG20 gene, HeLa cells were reported because they express all four splice variants, namely, IG20, MADD, IG20-SV2 and DENN-SV, detected to date in human cells and tissues. HeLa cell lines permanently transfected with cDNAs encoding IG20, MADD, and DENN-SV were assessed for TNFα-induced cell death. Consistently, relative to controls, HeLa-IG20 cells were most susceptible and HeLa-DENN-SV cells were most resistant to TNFα-induced cell death. Results obtained with HeLa-MADD cells were comparable to those obtained with HeLa cells transfected with an empty vector.

To understand why cells transfected with different splice variants of IG20 gene responded differently to TNFα treatment, potential functional motifs in the spliced regions were sought. An extensive search failed to reveal any apparent functional domains in the spliced regions. This suggested that splicing most likely results in conformational changes that affect their cellular localization or interactions with other proteins. Upon treatment with TNFα, all variants could interact with TNFR1 and enhance ERK activation. Differences in response to TNFα treatment of cells transfected with different IG20 splice variants are most likely not due to differences in these properties.

TNFα induced cell death is mediated through recruitment of FADD to the TNFR1/TRADD complex and activation of initiator caspase 8. Activation of caspase 8 leads to the activation of effector caspase 3 that cleaves a wide range of substrates ultimately leading to cell death. Upon treatment with TNFα/CHX, HeLa-IG20 cells showed maximal caspase activation. As expected, HeLa-Vector and HeLa-MADD cells showed only a moderate activation of caspase 8. Surprisingly, HeLa-DENN-SV cells showed little, if any, caspase 8 activity upon identical treatment. Consistent with these data, higher and lower levels of cleaved-active caspase 8 and caspase 3 were noted in HeLa-IG20 and HeLa-DENN-SV cells, respectively, compared to control cells. Activation of caspases was critical by inhibiting cell death in the presence of CrmA, which preferentially inhibits caspases 1 and 8 and thus can block activation of caspase 3 and prevent TNFα-induced cell death. IG20 appears to be acting primarily upstream of caspase-8 and its interaction with TNFR1 can enhance TNFα-induced caspase 8 activation. This also indicated that enhancing caspase activation is the dominant function of IG20 since it can override its own up-regulation of ERK activation commonly associated with cell survival.

Although the IG20 gene can encode multiple splice variants that are functionally different, how many are naturally expressed in various human tissues was not known prior to the present disclosure. Whether splice variants (e.g. DENN-SV) that are highly expressed in tumors contribute to enhanced cell proliferation and/or resistance to cell death was unknown.

IG20 and IG20-VB2, and the previously reported KIAA0358, MADD, and DENN-SV are splice variants of the IG20 gene, which is localized to chromosome 11p11 and consists of 36 exons. Differences among the above variants are due to alternative splicing of exons 13L, 16, 21, 26 and 34. Cell transfection studies showed that IG20 and DENN-SV conferred susceptibility and resistance respectively, to TNFα-induced apoptosis, whereas, MADD expression had no discernible effect. All three variants interacted with tumor necrosis factor type 1 (TNFR1) and enhanced activation of the extracellular-regulated kinase (ERK), but only IG20 enhanced activation of caspases 8 and 3. Further, IG20-mediated, TNFα-induced apoptosis could be abrogated by the caspase inhibitor, CrmA. These results suggested that enhancement of apoptosis by IG20 is mainly dependent on activation of caspases 8 and 3. In addition, several studies have implicated a role for IG20 splice variants in tumor formation. However, to date, no systematic study has been conducted to determine which variants are naturally expressed in human tumors and whether they might influence tumor cell growth and/or susceptibility to various treatments leading to induced cell death.

The tumor necrosis factor (TNF) super family of ligands and receptors play a critical role in the regulation of organogenesis, homeostasis, inflammation, innate, and adaptive immunity. A subset of TNF family ligands can bind to their cognate death receptors on cells and activate apoptosis. Inappropriate regulation of apoptosis could result in chronic inflammation, autoimmunity, or development of cancer.

TNF Related Apoptosis Inducing Ligand (TRAIL) can selectively kill some cancer cells and render others susceptible to co-treatment with drugs and irradiation, with little or no effect on most normal cells. TRAIL induced apoptosis is of considerable interest and has significant implications for developing novel cancer therapies.

The TNF Related Apoptosis Inducing Ligand (TRAIL) is a unique member of the TNF super family that can kill cancer cells selectively with little or no effect on most normal cells. Recombinant TRAIL, when systemically administered, can result in tumor shrinkage in vivo and in some cases, their complete elimination without resulting in any of the adverse systemic side effects often associated with TNF-α or CD95L. TRAIL, when used alone, can kill some tumor cell lines, however, its efficacy, when used in combination with chemotherapy and γ-irradiation, is high.

TRAIL can bind to 5 distinct receptors—Death Receptor 4 (DR4 or TRAILR-1), Death Receptor 5 (DR5 or TRAILR-2), Decoy Receptor 1 (DcR1, TRAILR-3, LIT or TRID), Decoy Receptor 2 (DcR2, TRAILR-4, TRUNDD) and Osteoprotegerin (OPG). Among these receptors, only DR4 and DR5 contain cytoplasmic Death Domains (DD) and are able to transduce apoptotic signals upon TRAIL binding. Although TRAIL can ligate both the DcR1 and DcR2, since their cytoplasmic tails lack a DD or have a partial DD, they are unable to transduce apoptotic signals. Little is known about OPG except that it is a soluble receptor and its association with TRAIL is relatively weak. Similar to TNFα and CD95L induced signaling, upon TRAIL treatment, FADD and caspase-8 are recruited to the DR4 and DR5 death inducing signaling complexes (DISC). Thus TRAIL; TNF-α and CD95L induced apoptotic signaling pathways share some common features. Earlier, the ability of TRAIL to selectively kill cancer cells was attributed to the dominant negative effects of the decoy receptors (DcRs) expressed on normal, but not on cancer cells, that can compete for TRAIL binding. More recent studies have shown that factors other than DcR expression confer resistance to TRAIL induced cell death.

IG20, MADD and DENN-SV could increase activity of TNF-α induced Mitogen Activated Protein (MAP) Kinase and Extracellular Signal Regulated (ERK) Kinase. Their ability to promote apoptosis however, varied. The IG20 and the DENN-SV splice variants rendered cells more susceptible and resistant to apoptosis respectively, whereas, the MADD splice variant had little or no apparent effect. Additional studies showed that all the three splice variants could interact with the TNFR1 upon TNF-α treatment, but only HeLa cells transfected with IG20 splice variant showed enhanced activation of caspase-8 and -3 that could be blocked by CrmA. IG20 acts as a pro-apoptotic molecule in enhancing TNF-α induced apoptosis.

IG20 can directly interact with TNFR1 and TRADD, but not CD95 and FADD indicating a potential role in TNFR1, but not CD95, mediated signaling. Analyses of DD sequences from different adaptor proteins showed that the DD of IG20 is more homologous to the DDs of DR4 and DR5 than it is to the DD of TNFR1 and TRADD.

The contrasting effects of DENN-SV and IG20 on susceptibility to death inducing stimuli suggests that the eventual outcome of these signaling pathways in tumor cells is determined, at least in part, by a balance in the expression levels of these two proteins. Indeed, HeLa cells that normally express all 4 variants, upon treatment with TNF-α undergo apoptosis, however, approximately only one half of the cells die. When dying cells were separated, on the basis of expression of apoptotic markers, from living cells and tested for expression of various splice variants, it was noted that while cells undergoing apoptosis expressed higher levels of the IG20 the viable cells expressed higher levels of DENN-SV.

Radiation therapy takes advantage of the inherently unstable nature of tumors. The DNA lesions induced by γ-irradiation activate an intrinsic cellular pathway for dealing with DNA damage. Cells initiate a set of physiological responses thought to facilitate DNA repair processes that include cell cycle arrest in G1, S phase, and G2, a slowing of DNA replication, and increased transcription of genes encoding proteins that participate in DNA replication and repair. If the degree of damage suffered by a cell is extensive, then the apoptotic pathway is activated leading to cell death. At the molecular level, several pathways have been studied, including p53 dependent and p53 independent pathways. Other molecules involved in the response to DNA damage include ATM, ATR, DNA-PK, hCds1/Chk2 and p21. Molecular mechanisms that regulate DNA damage, remain unclear.

SUMMARY OF THE INVENTION

A novel human gene (IG20) encodes multiple splice variants. The gene is essential for survival of the animal (knockout mice die immediately after birth). Splice variants have very important biological functions, but differ in their ability to affect cell death, survival and replication. The-IG20 splice variant is pro-apoptotic, anti-proliferative, and renders cells more susceptible to induced cell death (i.e. is a tumor suppressor).

IG20, or a fragment thereof, can be over expressed to control cell proliferation, cell cycle, and to render cells more susceptible to chemotherapy, radiation therapy or death receptor mediated cell death.

DENN-SV is pro-proliferative, anti-apoptotic, and renders cells more resistant to induced cell death (i.e. is an oncogene)

DENN-SV, or a fragment thereof, can be used to control cell proliferation, cell death and cell cycle, and to enhance survival and replication of primary cells such as beta cells, neuronal cells and others.

DENN-SV expression can be down modulated to reduce cell proliferation, affect cell cycle and increase susceptibility to treatment with chemotherapy, radiation therapy and death receptor mediated cell death.

Levels of these splice variants may be regulated to modulate functions of each other to affect cell cycle, death, and survival.

There are significant implications for cancer therapy, treatment of autoimmune diseases, stem cell therapy and establishment of cells and tissues that could be used for grafting, in the IG20/DENN-SV interactions.

Seven putative splice variants of the human IG20 gene were identified. Four variants namely, IG20, MADD, IG20-

SV2 and DENN-SV are expressed in human tissues with higher expression in tumors. While DENN-SV is constitutively expressed in all tissues, expression of IG20 appears to be regulated. Interestingly, over expression of DENN-SV enhanced cell replication and resistance to apoptosis induced by e.g. treatments with TNF-alpha, vinblastine, etoposide and gamma-radiation. In contrast, IG20 expression suppressed cell replication and increased susceptibility to the above treatments. Moreover, cells that were resistant and susceptible to TNF-alpha induced apoptosis exclusively expressed endogenous DENN-SV and IG20 respectively. When PA-1 ovarian cancer cells that are devoid of endogenous IG20 variant, but express higher levels of DENN-SV, were transfected with IG20, they showed reduced cell proliferation and increased susceptibility to apoptosis induced by TNF-alpha, TRAIL, and gamma-radiation. This indicated that over-expression of IG20 can override endogenous DENN-SV function. CrmA reversed the effects of IG20, but not DENN-SV. In contrast, dominant negative-I-kappa B reversed the effects of DENN-SV, but not IG20, and showed that DENN-SV most likely exerted its effects through NF-kappa B activation. IG20 gene plays a novel and significant role in regulating cell proliferation, survival and death through alternative mRNA splicing.

Additionally, while CrmA reversed TNFα induced apoptosis in cells expressing IG20, dominant-negative IBα, which inhibits NFκB activation, reversed DENN-SV-mediated resistance to apoptosis. Transfection of cDNA encoding a IG20 variant into cells of an ovarian cancer cell line that do not naturally express it, led to a significant decrease in their proliferation and a marked increase in susceptibility to various apoptosis-inducing agents. Collectively these studies show that IG20 expression can be used to render cells susceptible to apoptosis with potential implications for cancer therapy.

IG20 renders cells more susceptible to TRAIL induced apoptosis, which is inhibited by caspase inhibitors, p35 and CrmA, and dominant negative Fas associated death domain containing protein (FADD). Results from co-localization and immunoprecipitation studies showed that IG20 can interact with both TRAIL death receptors (DR), DR4 and DR5. Moreover, IG20 increased recruitment of FADD and caspase-8 into the TRAIL death inducing signaling complex (DISC). These results indicate that IG20 is a pro-apoptotic signaling molecule that has a novel function in enhancing TRAIL induced apoptosis by facilitating DISC formation.

Over-expression of DENN-SV and IG20 in HeLa cells conferred resistance and susceptibility, respectively, to the effects of γ-irradiation. HeLa IG20 cell susceptibility was due to enhanced apoptosis and reduced cell growth. This growth suppression was mediated by secreted soluble factors. Although HeLa DENN-SV cells grew more rapidly than control cells, replenishment with conditioned media (CM) from HeLa IG20 cells suppressed their growth. In addition, the CM from HeLa IG20 cells stopped the growth of ovarian PA-1 cancer cells in the G1-G0 cell cycle stage. Amongst an array of cytokines tested, IL-6 was found at the highest levels in HeLa IG20 culture supernatants, and IL-6 neutralization showed that it was in part responsible for the cell growth suppression. HeLa IG20 cells had elevated basal NFκB levels, a known regulator of IL-6 transcription. IG20 over-expression enhanced the combined apoptotic effects of TRAIL and γ-irradiation on HeLa cells.

HeLa cells stably transfected with DENN-SV YFP suppresses TRAIL apoptosis. Over-expression of DENN-SV can enhance resistance to TRAIL induced death (including other death ligands) at different concentrations of TRAIL. The kinetics of death induction is slower in these cells.

Treatment of cells with Si RNA against the middle portion of the DENN-SV, but not against the death domain (DD) of DENN-SV suppresses the levels of DENN-SV RNA. Cells treated with the Si RNA (against the middle portion whose sequence is given) undergo spontaneous apoptosis. The cells that fail to undergo spontaneous death after Si RNA induction are more susceptible to TNF-alpha induced apoptosis. The same enhanced susceptibility to treatment with other death receptor ligands is expected.

The normal mouse embryonic fibroblasts that are devoid of all splice variants of IG20 (from IG20 knockout mice; Rab3 GEP knockout mice), unlike human tumor cells do not undergo spontaneous apoptosis but are highly susceptible to TNF-alpha and FAS induced apoptosis. Anti-sense treatment could selectively kill tumor cells without affecting normal cells.

Various methods of treatment that can lead to over-expression of the IG20 gene or cDNA expression and prevention of splicing that results in larger amounts of IG20 accumulation in the cell are disclosed. A method to selectively prevent splicing of IG20 is performed with anti-sense oligos directed against the splice region or through manipulation of other unidentified IG20 splice factors. This can also be accomplished either through transfection of the whole, or portions of the protein/peptides. A similar effect can be accomplished through silencing of DENN-SV using Si RNA, anti-sense RNA, other oligonucleotides, DENN-SV protein or its fragments that can act as dominant negatives, and the like. Results described herein show the use of DENN-SV to facilitate cell survival and growth of primary cells such as beta cells in the islet of Langerhans (insulin producing cells), neuronal cells, stem cells, and the like.

DEFINITIONS

IG20, Insulinoma-Glucagonoma clone #20, MADD
MAP-Kinase Activating DeathDomain containing protein
DENN-SV, Differentially Expressed in Normal and Neoplastic cells—Short Variant
TRAIL, TNF Related Apoptosis Inducing Ligand
DR4/5—Death Receptor 4/5
DcR1/2, Decoy Receptors ½
DISC, Death Inducing Signaling Complex

DETAILED DESCRIPTION OF THE INVENTION

The IG20 gene is essential for survival of animals. It is over-expressed in human tumors and cancer cell lines, and can encode 4 different splice variants. The DENN-SV splice variant is constitutively expressed in all cells and tissues, and is highly-expressed in human tumors and cancer cell lines relative to normal tissues and other splice variants. Cells transfected with a cDNA encoding DENN-SV proliferate more aggressively, form larger colonies in soft agar and become resistant to TNF-α, TRAIL, etoposide and vinblastine induced cell death. In contrast, cells transfected with a cDNA encoding IG20 splice variant become more susceptible to cell death induced by the above treatments and grow slowly in culture. In addition, the increased susceptibility of IG20 transfected cells to TNF-α and TRAIL induced death is mediated by the activation of caspases-8 and -3 resulting from enhanced recruitment of caspase 8 and FADD to the Death Inducing Signaling Complex (DISC). The other two splice variants, MADD and IG20-SV2, exhibit little or no effect. More interestingly, cells that lack IG20, such as PA-1-ovarian carcinoma cell line, proliferate rapidly and resist TRAIL induced apoptosis. However, after IG20 is introduced, they replicate slowly and become susceptible to TRAIL induced apoptosis. These observations clearly show that DENN-SV and IG20 are biologically very important. Differential expression of IG20 and DENN-SV splice variants renders cells either more susceptible or resistant to induced cell death respectively, and the pro-apoptotic property of IG20 variant can be exploited to render tumor cells that are otherwise resistant to become susceptible to killing by TRAIL and/or chemotherapeutic agents.

Figure 30:
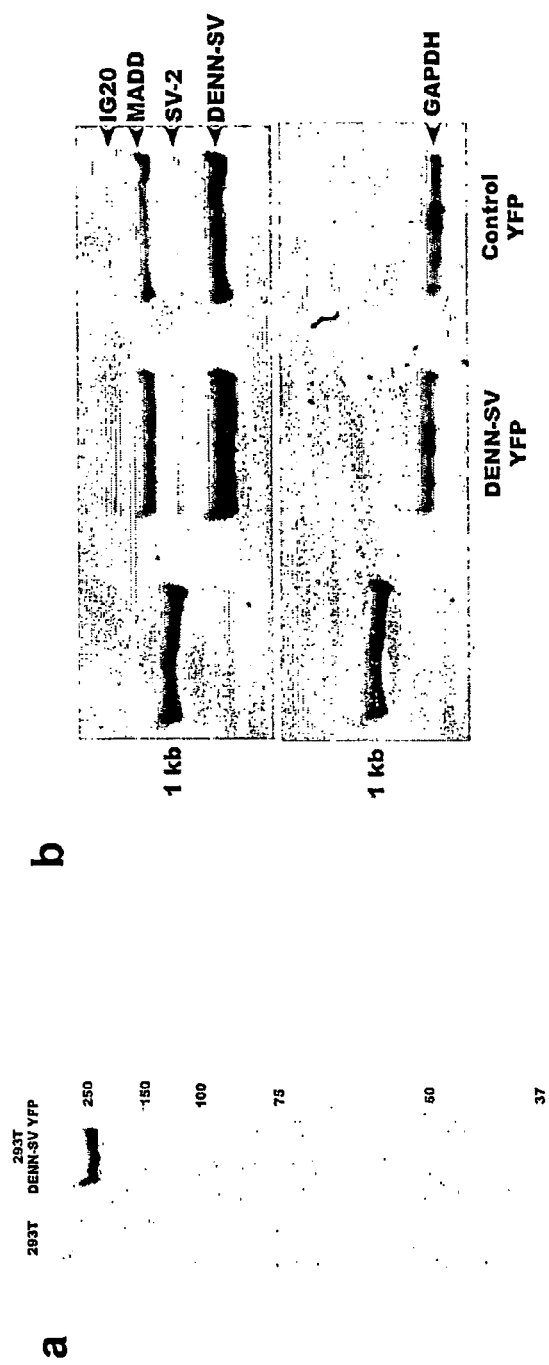
FIG. 30: a. Expression of the DSV-YFP was done by transfecting the construct in 293T cells. Lysates were then subjected to SDS-PAGE and immunoblotted with GFP antibody to detect the 250 Kda fusion protein. b. Stable HeLa cell lines of DSV-YFP were confirmed for specific overexpression of the integrated DSV-YFP construct (lane 2, top panel) by RT-PCR analysis. RNA was also probed for GAPDH (lane 1, 2, bottom panel) as loading control.

HeLa cells were stably transfected with DENN-SV YFP construct and expression of the construct was confirmed in the cell line as shown in FIG. 30.

Figure 31:
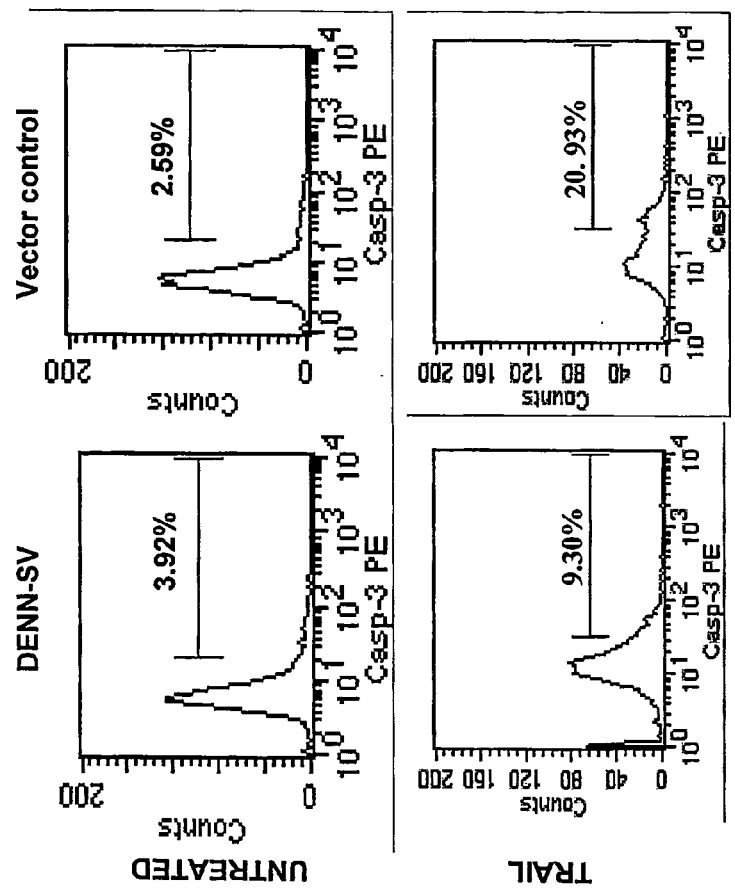
FIG. 31: Stable DSV-HeLa cells and vector control cells were treated with 25 ng/mL of TRAIL for 3H or left untreated. The cells were then collected, fixed and stained for acive caspase-3 and FACS analyzed for percentage of cells positive for caspase-3.

Stable transfection of HeLa cells with DENN-SV suppresses TRAIL apoptosis as shown in FIG. 31.

Figure 32:
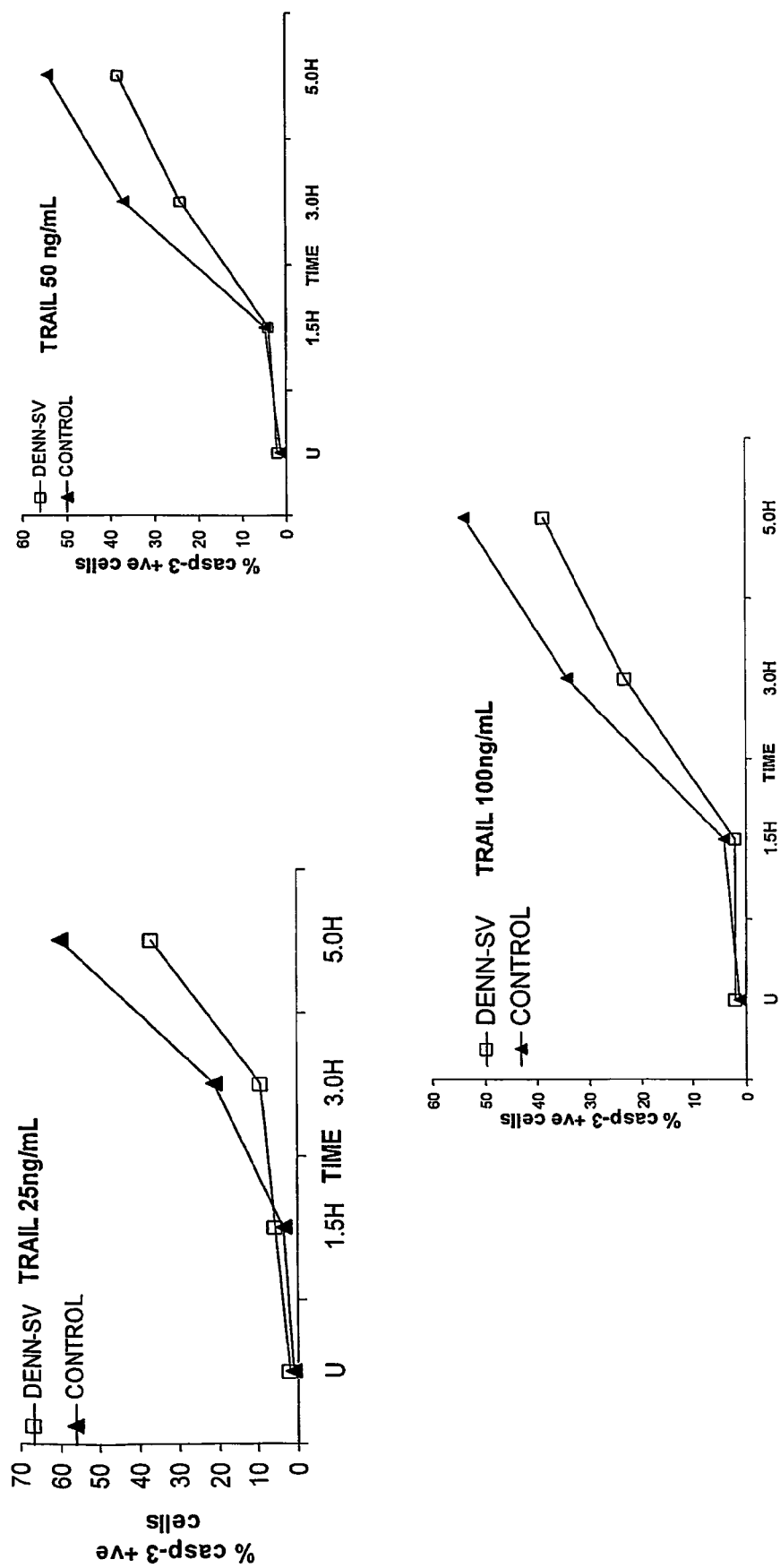
FIG. 32: Stable DSV-HeLa cells were left untreated or treated with 3 different concentrations of TRAIL, for either 1.5 h, 3.0 h or 5.0 h. Cells were then collected, fixed and stained with anti-active caspase-3 PE antibody and analyzed by FACS.

Caspase-3 Kinetics dose response and time course of TRAIL apoptosis is shown in FIG. 32. FIGS. 31-32 show that over-expression of DENN-SV can enhance resistance to TRAIL induced death (this is true for other death ligands as well) at different concentrations of TRAIL. These figures also show that the kinetics of death induction is slower in these cells.

Figure 33:
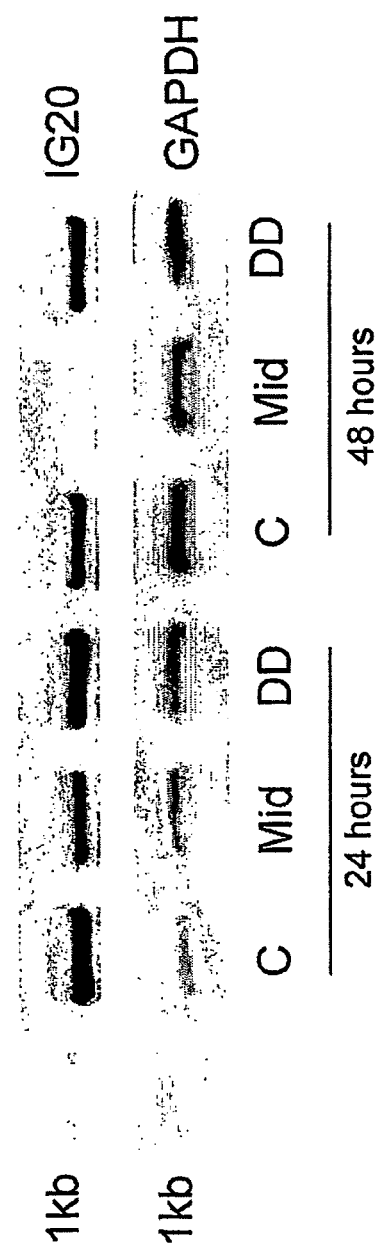
FIG. 33: Mid si RNA region. Total RNA was extracted from HeLa cells transduced with lentiviral vectors expressing control vector, Mid and DD siRNA regions after 24 and 48 hours post-transduction using Trizol (Life Technologies, Inc). 48 hours after transduction, the cells expressing the Mid siRNA region (5'-GTACCAGCTTCAGTCTTTC-3') (SEQ ID NO: 1) show knockdown of the IG20 gene as compared to the control vector and DD transduced cells. 0.8 µg of RNA was used in the Super-script one-step RT-PCR (Life Technologies, Inc) using F2-B2 primers, which amplify all isoforms of the IG20 gene. GAPDH was used as an internal control for the RT-PCR. The PCR products were separated on a 1% agarose gel.

FIG. 33 shows that treatment of cells with Si RNA against the middle portion of the DENN-SV, but not against the death domain (DD) of DENN-SV suppresses the levels of DENN-SV RNA (completely abrogates).

Figure 34:
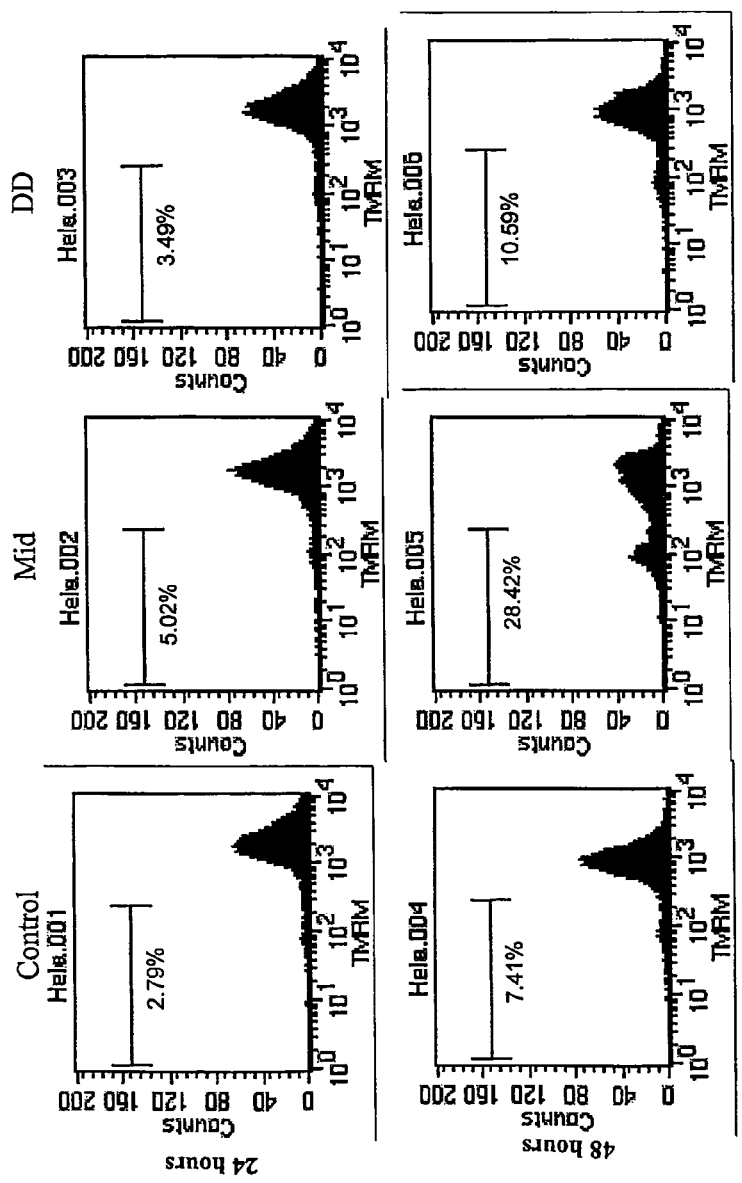
FIG. 34: Mid and DD si RNA. HeLa cells transduced with lentiviral vectors expressing vector control, Mid and DD siRNA regions were monitored for apoptosis after 24 and 48 hours post-transduction. Apoptosis was measured by TMRM staining. Viral transduction was normalized by GFP expression and GFP positive cells were gated for the TMRM analysis.

FIG. 34 shows that cells treated with the Si RNA (against the middle portion whose sequence is given) undergo spontaneous apoptosis.

Figure 35:
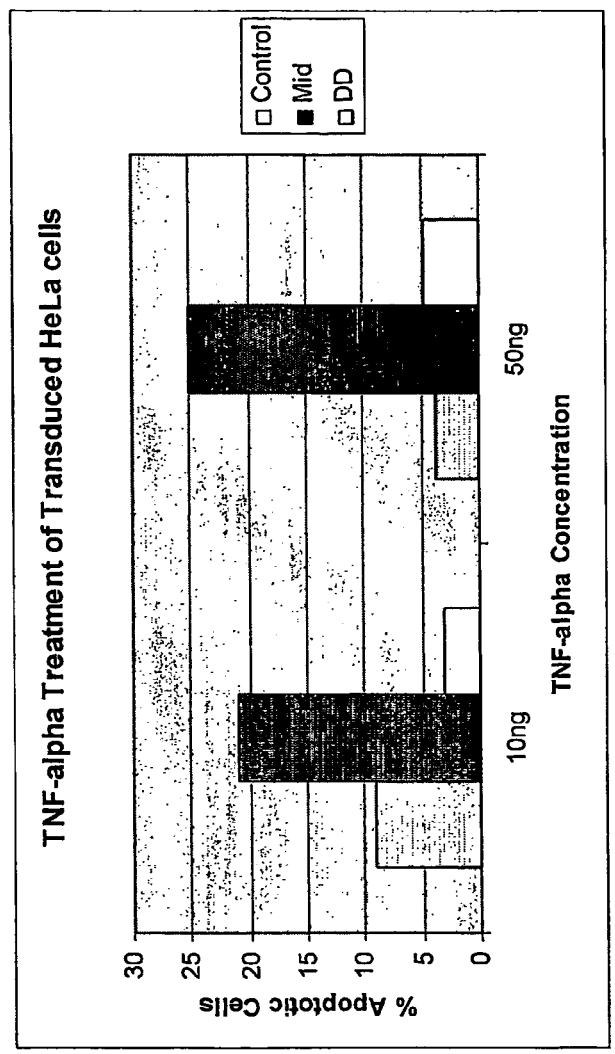
FIG. 35: Surviving HeLa cells (2.5×105) transduced with lentiviral vectors (for 48 hours) expressing vector control, Mid and DD siRNA regions were plated onto 6-well plates. 24 hours later viable cells were treated with the indicated concentrations of TNF-α for 3 hours and analyzed for apoptosis as measured by TMRM staining. Viral transduction was normalized by GFP expression and GFP positive cells were gated for the TMRM analysis.

The data in FIG. 35 show that those cells that fail to undergo spontaneous death after Si RNA induction are more susceptible to TNF-alpha induced apoptosis. The same enhanced susceptibility to treatment with other death receptor ligands is expected based on this study.

Figure 36:
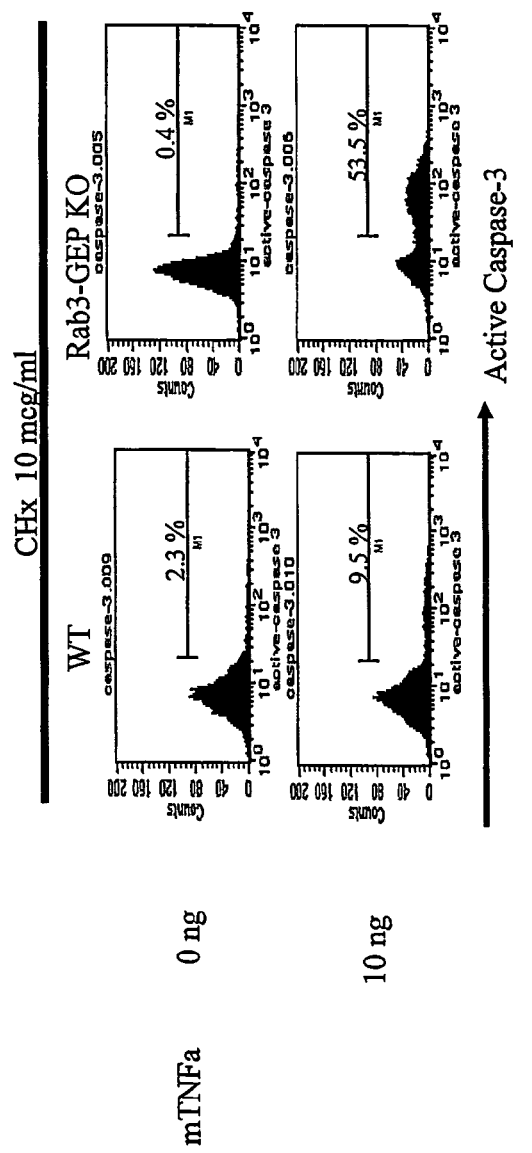
FIG. 36: Rab3-GEP KO MEFs are susceptible to TNFα-induced apoptosis. Rab3-GEP KO and wild type mouse embryonic fibroblasts (MEFs) were treated for 4 hrs with 10 ng/ml of murine TNF-alpha (SIGMA) and 10 mcg/ml of cycloheximide. For testing levels of active caspase-3, MEFs were harvested, fixed and permeabilized. MEFs were stained with anti-active-caspase-3 PE-conjugated antibody and analysed by FACS for PE-positive population.
Figure 37:
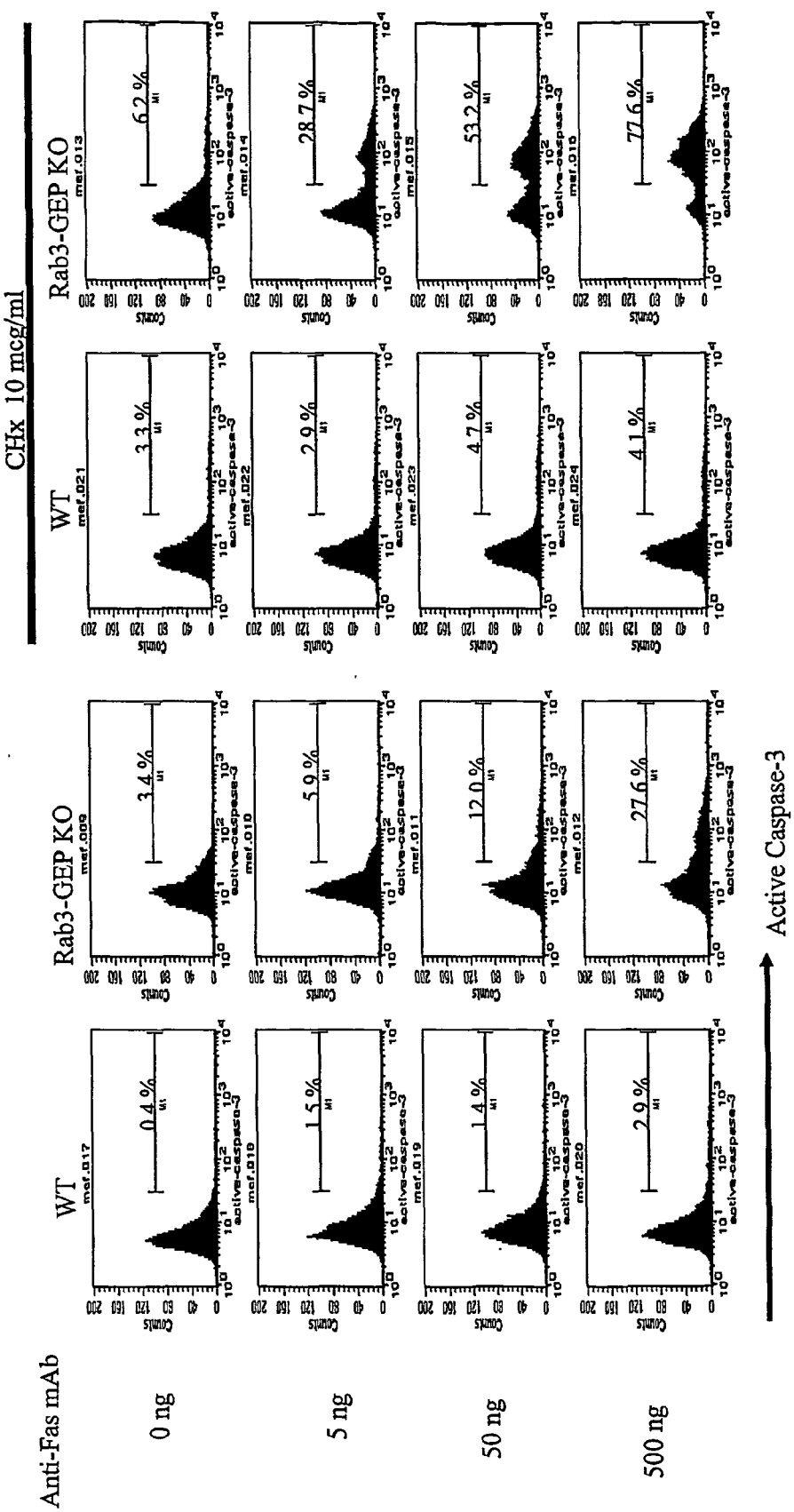
FIG. 37: Rab3-GEP KO MEFs are susceptible to Fas-induced apoptosis. Rab3-GEP KO and wild type mouse embryonic fibroblasts (MEFs) were treated for 8 hrs with anti-Fas mAb (clone Jo2, BD Pharmingen) alone or along with 10 mcg/ml of cycloheximide (CHx). For testing levels of active caspase-3, MEFs were harvested, fixed and permeabilized. MEFs were stained with anti-active-caspase-3 PE-conjugated antibody and analysed by FACS for PE-positive population.

(FIGS. 36-37) show that normal mouse embryonic fibroblasts that are devoid of all splice variants of IG20 (from IG20 knockout mice; Rab3 GEP knockout mice), unlike human tumor cells do not undergo spontaneous apoptosis (as seen in FIG. 34) but are highly susceptible to TNF-alpha (FIG. 36) and FAS (FIG. 37) induced apoptosis. These results point to the differences between normal and tumor cells. They indicate that anti-sense treatment could selectively kill tumor cells without affecting normal cells.

The data shown in FIGS. 30-37 complement the earlier data (FIGS. 1-29), which showed that IG20 can act as a competitive antagonist and over-ride DENN-SV function. The data in FIGS. 30-37 show that the same effect can be elicited by down-modulating DENN-SV. Various methods of treatment that can lead to over-expression of IG20 gene or cDNA expression and prevention of splicing that results in larger amounts of IG20 accumulation in the cell are disclosed. A method to selectively prevent splicing of IG20 is performed with anti-sense oligos directed against the splice region or through manipulation of other unidentified IG20 splice factors. This can also be accomplished either through transfection of the whole, or portions of the protein/peptides. The data in FIGS. 30-37 show that a similar effect can be accomplished through silencing of DENN-SV using Si RNA, anti-sense RNA, other oligonucleotides, DENN-SV protein or its fragments that can act as dominant negatives, and the like. Results disclosed herein show the use of DENN-SV to facilitate cell survival and growth of primary cells such as beta cells in the islet of Langerhans (insulin producing cells), neuronal cells, stem cells, and the like.

EXAMPLES

Example 1

Figure 1:
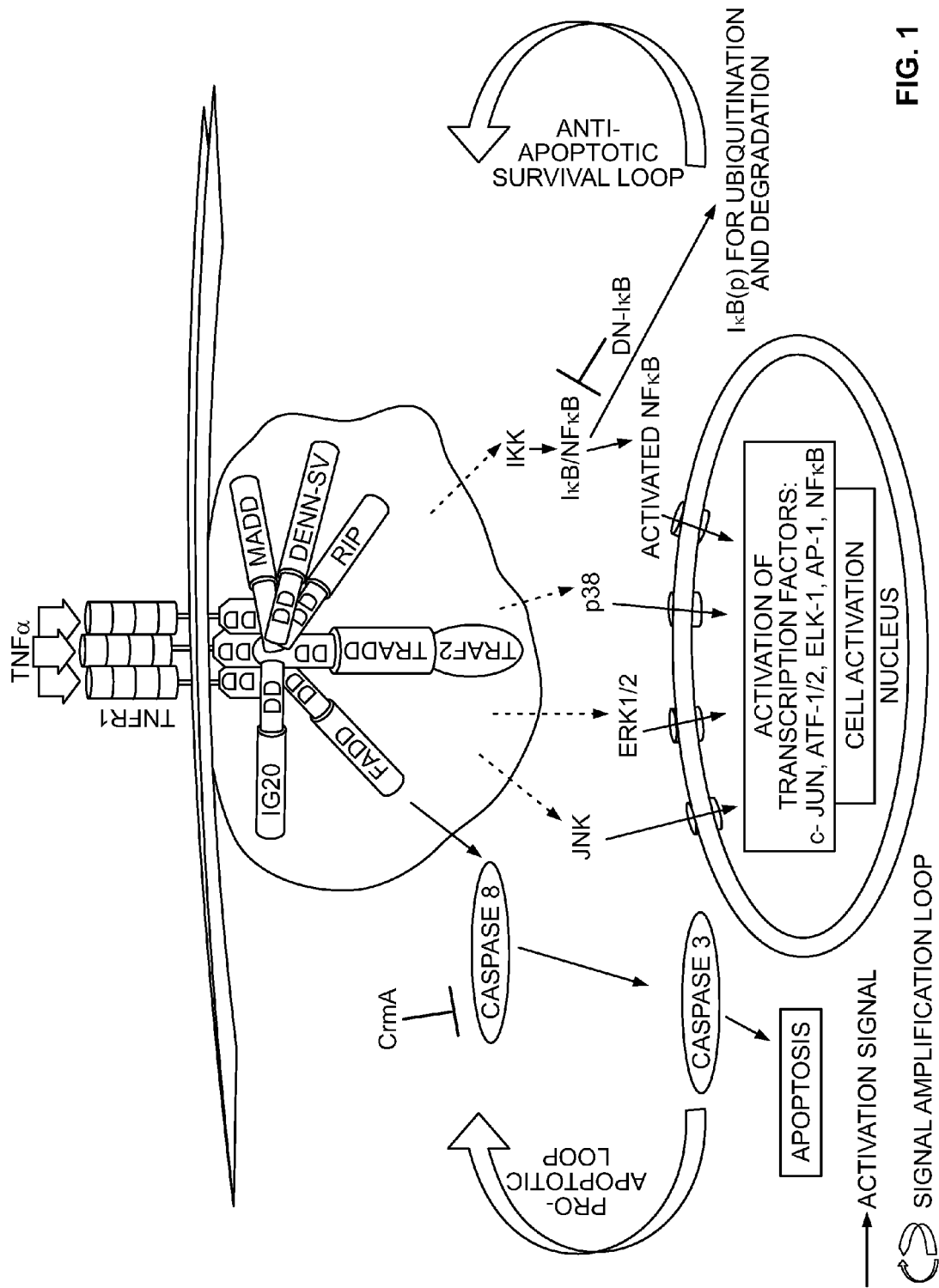
FIG. 1: Shows some of the known signaling pathways that are activated upon TNF-α binding to TNFR1. IG20 causes enhanced recruitment of FADD and caspase 8 leading to enhanced apoptosis. In contrast, DENN-SV does not promote FADD/caspase 8 recruitment but leads to enhanced activation of NFκB and cell survival pathway. All variants can activate various kinases indicating that this might not distinguish IG20 from DENN-SV.

Ig20 Suppresses Tumor Cell Survival and Enhances their Susceptibility to Apoptosis and Cancer Drug FIG. 1 shows a model of a signaling pathway.
Identification of IG20 Splice Variants
Analyses of cDNA sequences (FIG. 2) showed that all seven variants of IG20 identified to date arise from alternative splicing of exons 13L, 16, 21, 26, and 34. The full-length cDNA of IG20 (IG20-FL) (accession number AF440100) is 5995 base pairs (bps) long, consists of all 36 exons and represents the longest variant. Splicing of exon 34 alone generates KIAA0358 (accession number AB002356) that consists of 5942 bps. Splicing of exons 21 and 26, and splicing of exons 16, 21 and 26 generate 5878 bps long IG20 (accession number AF440101) and 6002 bps long MADD (accession number U77352) (SEQ ID. NO: 13)), respectively. MADD is also known as DENN (accession number U44953) that is 5844 bps long. Splicing of exons 13L, 21 and 26, and 13L, 16, 21 and 26 generate 5749 bps long IG20 SV2 (accession number AF440102) and 5689 bps long IG20-SV3 (accession number AF440103 (SEQ ID. NO: 14)) (earlier referred to as DENN-SV). Finally, splicing of all five exons (13L, 16, 21, 26 and 34) generates IG20-SV4 (accession number AF440434), which is the shortest variant and consists of 5619 bps. Sequencing of cDNAs from several tissues and cell lines confirmed that bands of the same size have identical sequences. Differences in nucleotide sequences among various variants are not limited to splicing of the above exons, and include nucleotide sequences upstream of the ATG start codon and downstream of the stop codon.

Only IG20, IG20-VB2, MADD and DENN-SV are Expressed in Human Tissues

Figure 3:
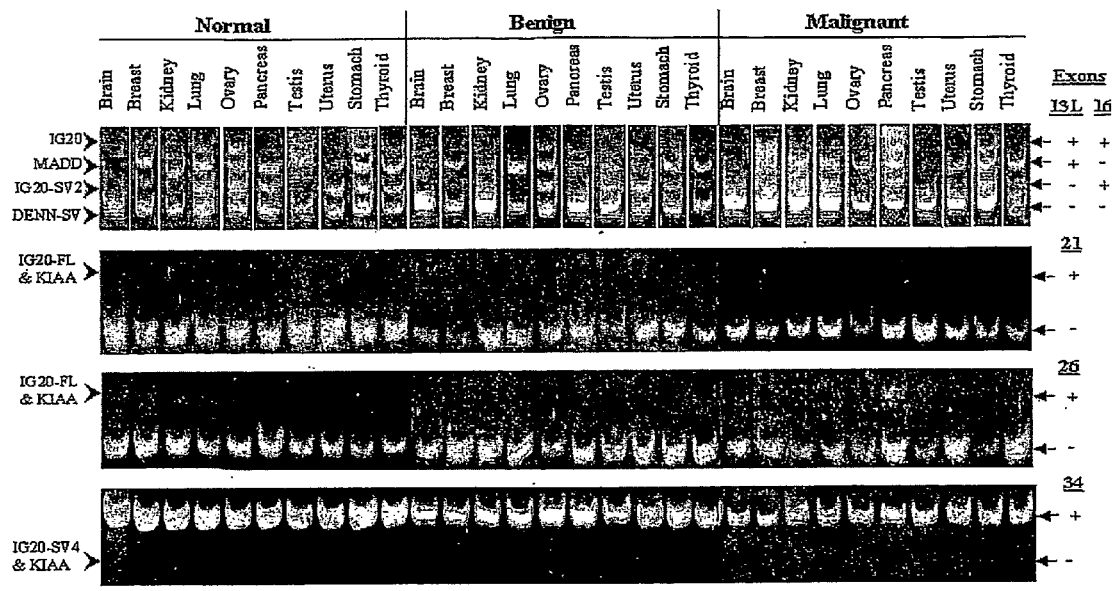
FIG. 3: RT-PCR of mRNA from human tissues using IG20 primers. Fifty seven samples representing normal, benign and malignant forms from ten different human tissue types were used to extract mRNA and perform RT-PCR. This was accomplished using exon specific primers, as described in the Materials and Methods. Several samples from the same tissue type were used; however, only one representative of these samples is presented in this figure. The splicing patterns of exons 13L, 16, 21, 26 and 34 for each of the tissues tested are shown.

Expression patterns of IG20 was examined in human tissues. mRNA from fifty-seven different human tissues and 14 different human cell lines was used in RT-PCR using multiple sets of IG20-specific primers. Four different primer pairs were designed to amplify regions of IG20 that contain alternatively spliced exons 13L, 16, 21, 26 and 34. FIG. 3 shows expression patterns of IG20 variants in normal, benign and malignant forms of ten different human tissue types. To validate RT-PCR results and to identify specific splice variants, mRNAs from several samples of the same tissue type were used in RT-PCR and consistent results were obtained but only one representative sample for each tissue type is shown. Results further demonstrated that of the 36 exons only a select few undergo alternative splicing. Together, the above data show that up to 4 different IG20 splice variants are expressed in different patterns and levels in all human tissues tested.

None of the tissues tested expressed three of the splice variants namely, KIAA0358, IG20-FL and IG20-SV4. KIAA0358 was identified as an EST and was isolated from a human brain library, whereas IG20-SV4 was isolated as a partial clone from a human insulinoma library. Similarly, expression of the full-length clone that contains all 36 exons has not been detected.

Figure 4:
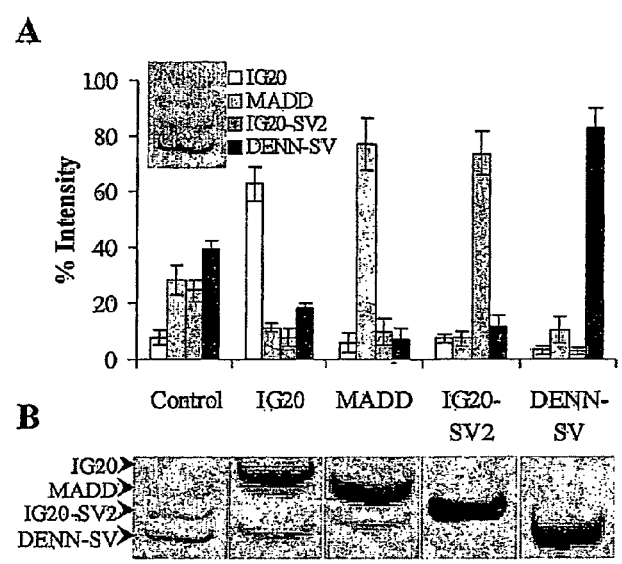
FIG. 4: Relative intensities of cDNAs corresponding to IG20 splice variants in transfected cells. mRNAs from 293T cells stably transfected with IG20, MADD, IG20-SV2, and DENN-SV variants were extracted and 100 ng of each sample was used for RT-PCR as described in the Materials and Methods. RT-PCR products were subjected to PAGE using a 5% gel and stained with ethidium bromide. (A) Quantitation of band intensities was performed using ImageQuant analysis. Intensities were calculated as the percent intensity of the band corresponding to a specific IG20 variant to the total intensities of all bands within the same sample. Shown are means and standard deviations from three independent groups of cells transfected separately. P values were <0.05 for all test groups. (B) Shows PAGE photos for one of the transfections used to generate data shown in (A).
Figure 5:
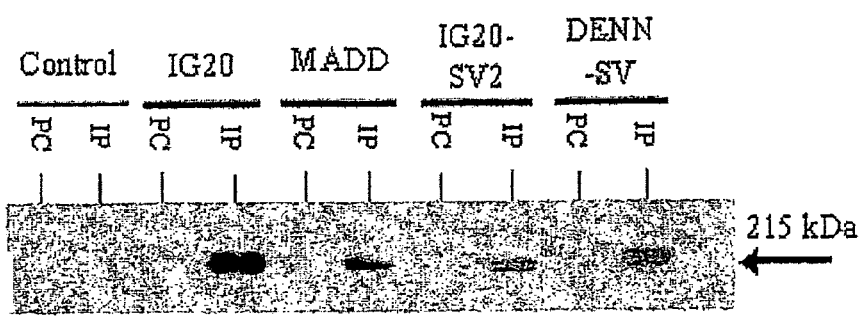
FIG. 5: Expression of 6-Histidine-tagged IG20 splice variants shows the expression of the four transfected IG20 cDNA constructs fused to a sequence encoding the 6-Histidine tag at the 5' end. The tagged proteins, seen at about 215 kDa, as expected, correspond to the transfected cDNAs of IG20 splice variants, indicating that the proteins were encoded by the transfected cDNAs.

All Four IG20, MADD, IG20-SV2, and DENN-SV Can Encode Proteins 293T cells with cDNAs encoding each of the four splice variants of IG20 are expressed in human tissues. FIG. 4 shows levels of IG20 cDNAs amplified from mRNA transcripts that correspond to the transfected IG20 splice variant. Proteins encoded by these cDNAs were immunoprecipitated using anti-IG20 polyclonal antibodies and subjected to Western Blotting using an anti-His monoclonal antibody. His-tagged IG20 protein variants encoded by the transfected cDNAs were seen at the expected molecular weight of about 215 kDa (FIG. 5). Due to small differences in their coding sequences, these proteins have similar apparent molecular weights. These results showed that the transfected cDNAs could encode the corresponding proteins.

Susceptibility of HeLa cells transfected with each of the above described four IG20 splice variants to TNF and cyclohexamide-induced apoptosis by trypan Blue exclusion, chromatin condensation, and mitochondrial depolarization. HeLa-IG20 and HeLa-DENN-SV cells showed an increase and a decrease in TNFα-induced cell death respectively, whereas HeLa-MADD cells showed no significant difference in apoptosis relative to the controls. Interestingly, HeLa-IG20-SV2 cells showed a phenotype similar to that of HeLa-MADD and HeLa-control cells (i.e., no significant effects on apoptosis).

Figure 6:
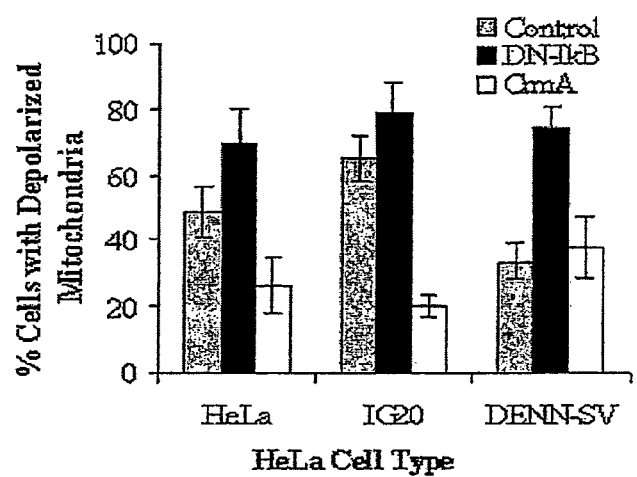
FIG. 6: Effects of Dominant Negative-IκIB and CrmA on TNF-α induced, IG20-mediated apoptosis. Blocking effects of DNIκBα and CrmA on the pro-apoptotic and anti-apoptotic effects of IG20 and DENN-SV are shown. Percentages represent mitochondrial depolarization (used as an indicator of apoptosis) due to TNF-α and cyclohexamide treatment; this was calculated by subtracting percentage of TMRE-negative cells transfected with either empty vector or with vectors containing either CrmA or DNIκKBα, from percentage of TMRE-negative cells transfected with the same construct but treated with TNF-α and cyclohexamide. TMRE data were obtained from GFP-positive gated cells only. Data shown in the figure represent three different wells for each sample. Experiment was repeated at least three times and consistent results were obtained. P values were <0.05 for all test groups.

Dominant-Negative I-KappaB-Alpha (DN-IκBα) Abrogates DENN-SV-Mediated Resistance to TNFα-Induced Apoptosis IG20 enhances TNFα-induced apoptosis by activation of caspases 8 and 3. To understand the mechanism by which DENN-SV confers resistance to TNFα-induced apoptosis, CrmA and DN-IκB were used that can block activation of caspases or NFκB, respectively. FIG. 6 shows that there was maximal inhibition of TNFα-induced apoptosis by CrmA in HeLa-IG20 cells relative to control cells, with little or no effect on HeLa-DENN-SV cells. In contrast, DN-IκBα significantly enhanced apoptosis in HeLa-DENN-SV cells and had minimal effects on HeLa-IG20 cells. Together, these results suggested that IG20 and DENN-SV play distinct roles in TNFα-induced signaling by activating either caspases that can be blocked by CrmA or NFκB that can be blocked by DN-IκBα, respectively.

Endogenous Expression of IG20 Splice Variants Correlates with Susceptibility to TNFα-Induced Apoptosis To see whether expression of endogenous IG20 and DENN-SV were associated with increased and reduced cell death respectively, cells that were susceptible (Annexin V-positive) were separated from those that were resistant (Annexin V negative) to TNFα-induced apoptosis, and the levels of expression of IG20 variants were compared. FIG. 7A showed that, relative to unseparated control HeLa cells, there was very little expression, if any, of IG20 (pro-apoptotic variant) and a much higher level of expression of DENN-SV (anti-apoptotic variant) in resistant cells. In contrast, cells undergoing apoptosis showed a very high level of expression of IG20 and undetectable levels of other variants. The percentages of cells with depolarized mitochondria were measured in these two subpopulations of cells, as another marker of apoptosis. As shown in FIG. 7B, maximum apoptosis (cells with depolarized mitochondria) (93%) was noted in Annexin V-positive cells, whereas minimum apoptosis (8%) was seen in Annexin V-negative cells, compared to unseparated control cells (35%).

IG20 and DENN-SV Exert Contrasting Effects on Cell Proliferation and Responses to Apoptosis-Inducing Agents HeLa-IG20 and HeLa-DENN-SV cells showed profound differences in their response to vinblastine treatment (FIGS. 8A and -B). HeLa-DENN-SV cells were not significantly affected when they were treated with a dose of 0.05 ∝M. In contrast, there were only a few HeLa-IG20 colonies detectable indicating their enhanced susceptibility. HeLa-control cells showed an intermediary response. Additionally, Vinblastine-induced apoptosis was noted in 70% and 21% of HeLa-IG20 and HeLa-DENN-SV cells respectively, compared with 46% of HeLa-controls, as measured by chromatin condensation.

Next, the response of these cells to treatment with different doses of etoposide was evaluated. On average, HeLa-IG20 cells formed 8 colonies after treatment with 5 μMetoposide. In contrast, HeLa-DENN-SV cells formed as many as 125 colonies, compared to 39 colonies formed by HeLa-control cells (FIGS. 9A and B). Upon treatment with 20 μM of etoposide, HeLa-IG20 cells formed very few or no colonies, whereas HeLa-DENN-SV cells formed approximately 40 colonies. In addition, as shown in FIG. 9A HeLa-DENN-SV cells were able to grow even after treatment with 30 μM of etoposide. These results were further substantiated by assessing apoptosis (FIG. 9C) and cell division (FIG. 9D) after etoposide treatment. Expectedly, HeLa-DENN-SV cells displayed a noticeable resistance to etoposide-induced apoptosis. However, interesting results were obtained with HeLa-IG20 cells. They did not show a marked increase in susceptibility to apoptosis (FIG. 9C), but showed a significant decrease (9%) in cell division as indicated by CFDA staining, compared to DENN-SV (36%) and control (24%) cells (FIG. 9D).

The growth rates of HeLa-IG20 and HeLa-DENN-SV cells indicated that HeLa-IG20 and HeLa-DENN-SV cells showed growth attenuation or rapid growth respectively, compared to HeLa-control cells (FIG. 10A). To evaluate their ability to grow in soft agar resulting in colony formation, cells were plated at different densities. On average, HeLa-DENN-SV cells and HeLa-IG20 cells formed 20 and 2 colonies respectively, while HeLa-control cells formed 4 colonies (FIGS. 10B and C). Additionally, HeLa-DENN-SV colonies were bigger, while HeLa-IG20 colonies were smaller, than HeLa-control colonies.

Effects of IG20 Over-Expression on Cells that Do Not Express Endogenous IG20

Figure 7:
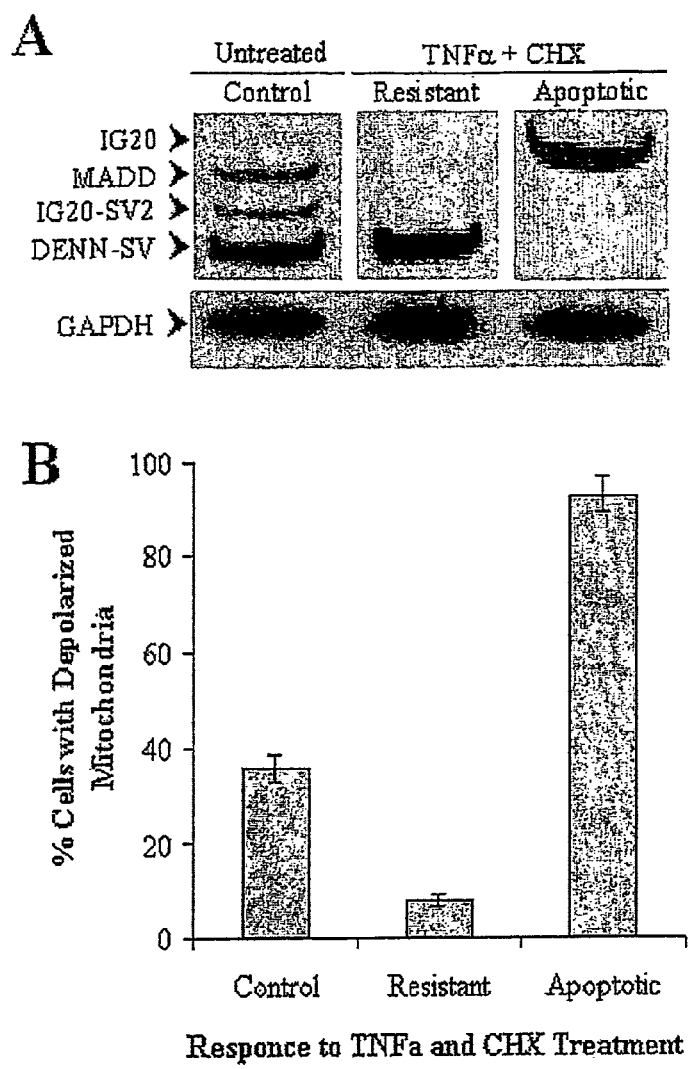
FIG. 7: Endogenous Expression of IG20 variants and Susceptibility To TNF-Induced Apoptosis. (A) Magnetic Separation of Apoptotic and TNFα-resistant Cells. Apoptotic cells were magnetized and physically separated from TNFα-resistant cells using the Annexin V-conjugated microbeads, as described in Materials and Methods. mRNAs were then isolated from apoptotic and TNFα-resistant cells separately and were used in RT-PCR using IG20-specific primers F-1 and B-1. The figure shows very little expression, if any, of IG20 (the pro-apoptotic variant) in cells resistant to TNFα-induced apoptosis, compared to control cells. In contrast, marked increase in expression of IG20 with no expression of DENN-SV (the anti-apoptotic variant) is seen in apoptotic cells. (B) TNFα-Induced Mitochondrial Depolarization in apoptotic and TNFα-resistant cells. Cells in (A) were then assessed for mitochondrial depolarization. As shown in the figure, maximal differences were seen in separated cells vs. un-separated control cells. Bars represent averages from three wells for each group. The experiment was repeated at least three times and consistent results were obtained. These results were statistically significant, as p values were <0.05 for both resistant and apoptotic groups relative to controls.
Figure 8:
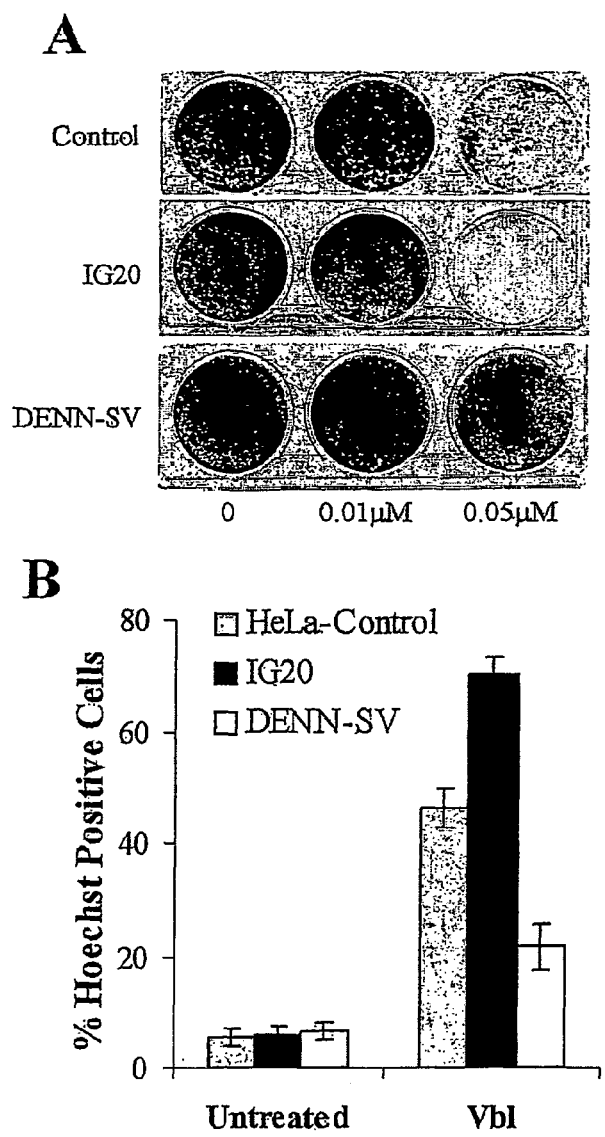
FIG. 8: Effect of IG20 and DENN-SV on Cell Survival and Apoptosis of TransfectedCells after Vinblastine Treatment. (A) Cell survival after Vinblastine treatment. The figure shows crystal violet staining of cell colonies two weeks after treatment with the indicated doses of vinblastine. (B) Vinblastine-Induced apoptosis. Cells treated with 0.05 µM vinblastine were stained with Hoechst 24 hours after the treatment in order to determine the percentage of cells with condensed chromatin. P values were <0.05 for all test groups.
Figure 9:
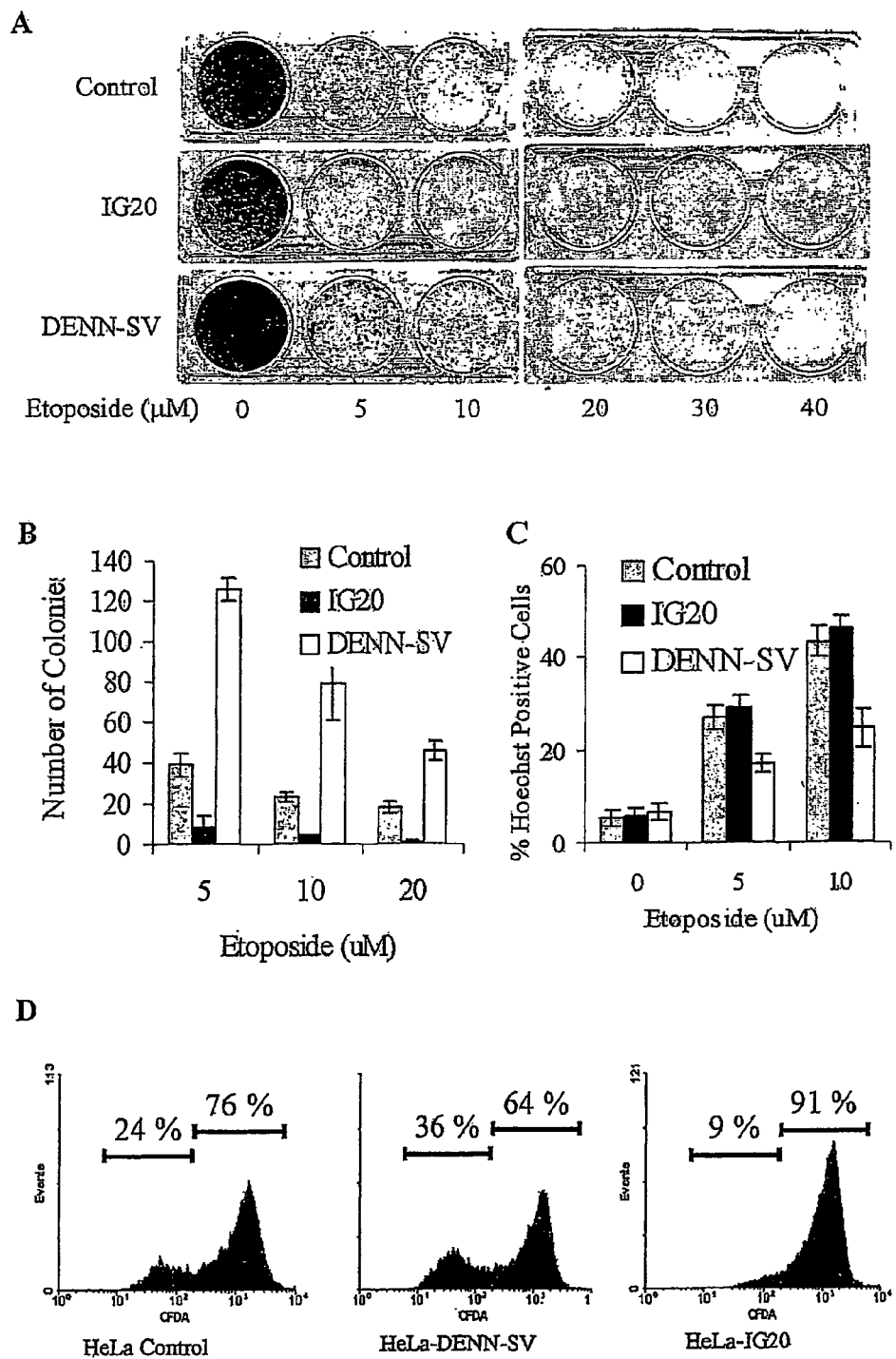
FIG. 9: Effects of IG20 and DENN-SV on survival and proliferation of cells treated with etoposide. (A) Cell survival after etoposide treatment. Cells were treated with the indicated doses of etoposide and allowed to grow in culture for 2 weeks and stained with crystal violet. (B) Enumeration of colonies after etoposide treatment. Three different experiments using the indicated doses of etoposide were used to determine the effects of the drug on HeLa-control, HeLa-IG20 and HeLa-DENN-SV cells. P values were <0.05 for all test groups. (C) Etoposide-Induced apoptosis. Cells treated with the indicated doses of etoposide were stained with Hoechst as described in Materials and Methods and evaluated for chromatin condensation under a microscope. P values were <0.05 for all test groups. (D) Cell Division after Etoposide Treatment. Cells were stained with CFDA and then subjected to 5 µM etoposide treatment for 5 days. Cells were then harvested and evaluated by FACS for CFDA staining intensity. Histograms show relative levels of CFDA dye retention. The peak on the left within each histogram represents cells that have undergone cell division, and therefore, partially lost CFDA staining, whereas the peak on the right represents undivided cells that retained maximum CFDA staining.
Figure 10:
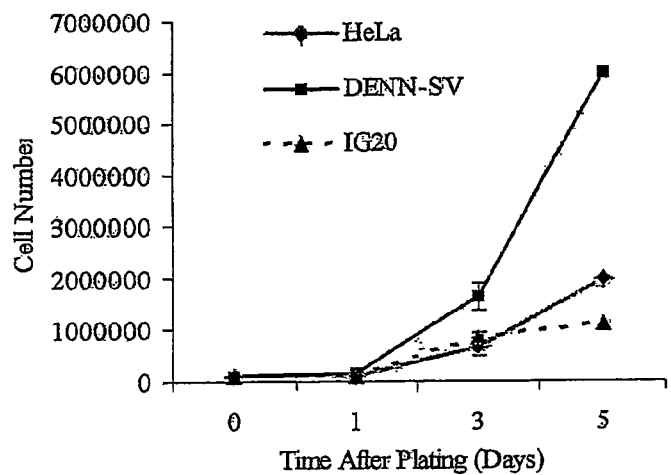
FIG. 10. Effects of IG20 and DENN-SV on HeLa cell growth and colony formation in soft agar. (A) Growth rates of HeLa-control, HeLa-IG20 and HeLa-DENN-SV cells. $1 \times 10^5$ cells/plate were plated in 100 mm² dishes in DMEM with 10% FCS. Cells were harvested and counted on the indicated days after plating. Data are presented as mean+33 standard deviation of triplicate plates. P values were <0.05 for all test groups. (B) Colony formation in soft agar. HeLa-control, HeLa-IG20, and HeLa-DENN-SV cells were plated in soft agar as described in Materials and Methods. Three weeks later, growth in soft agar was observed at a magnification of 10×. Photos show representative fields from each cell type. (C) Enumeration of colonies shown in (B). Ten randomly selected fields of equal size were used to count cell colonies. P values were <0.05 for all test groups.
Figure 10:
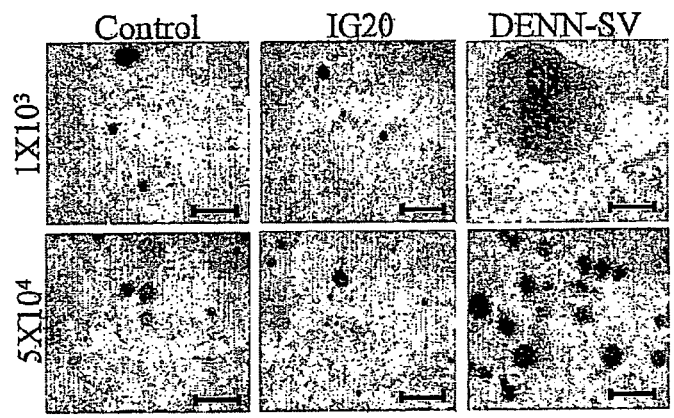
Figure 10:
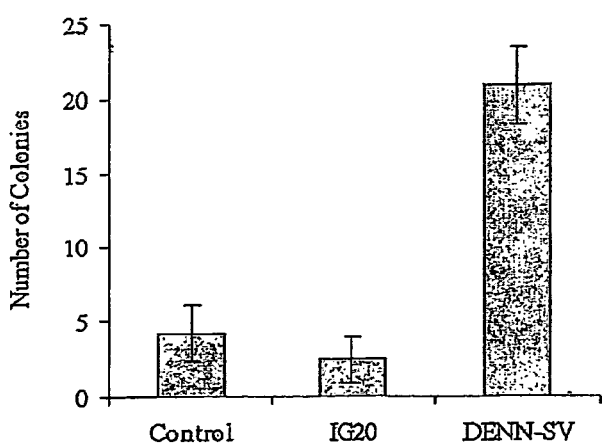
Figure 11:
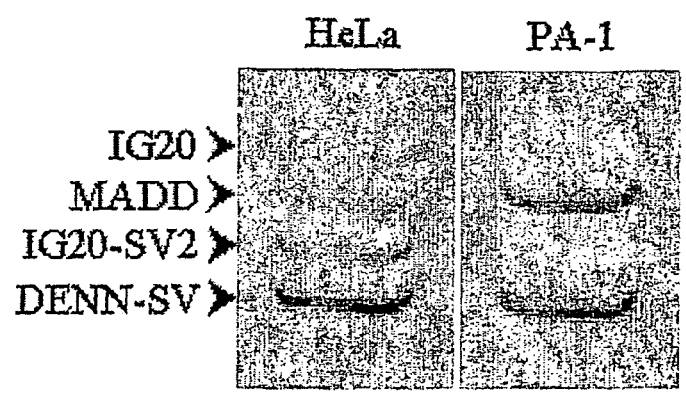
FIG. 11: Expression of IG20 in HeLa and PA-1 cells. Shown are RT-PCR products using mature poly A+mRNA extracted from HeLa and PA-1 cell lines. IG20 F-1 and B-1 primers that flank exons 13L and 16 were used as described in Materials and Methods. The figure demonstrates that cDNA bands that correspond to the four IG20 splice variants (i.e., IG20, MADD, IG20-SV2, and DENN-SV) are expressed in HeLa cells, whereas only MADD and DENN-SV are expressed in PA-1 cells.
Figure 12:
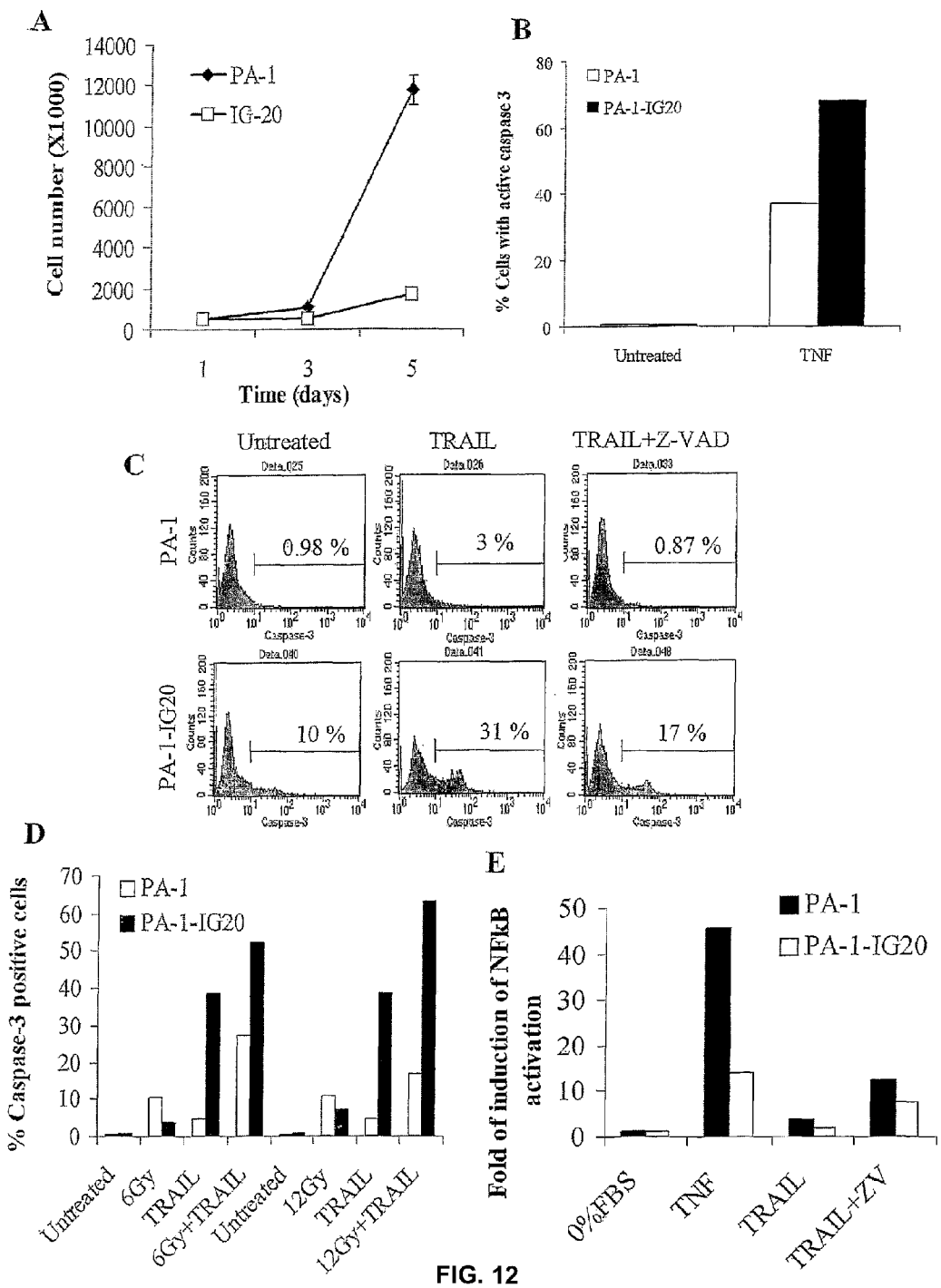
FIG. 12: Effects of IG20 on PA-1 Cell Phenotypes. (A) Growth Rates. PA-1 and PA-1-IG20 cells were plated as described in Materials and Methods. Cells were then harvested and counted on the indicated days. Data are presented as mean+standard deviation of three plates for each sample. P values were <0.05 for all test groups. (B) TNFα-Induced Apoptosis. Cells were either untreated or treated with TNFα and cyclohexamide (CHX) for three hours, as described in Materials and Methods and then tested for percentages of cells with active caspase 3. (C) TRAIL-Induced Apoptosis. Cells were either untreated or treated with TRAIL for three hours and then tested for percentages of cells with active caspase 3, in the presence or absence of Z-VAD, an inhibitor of caspase activation. (D) Response to α-radiation and TRAIL Treatment. PA-1-IG20 cells exposed to 6 and 12Gy of α-radiation were plated as described in Materials and Methods. Twenty-four hours later, cells were either untreated or treated with TRAIL for 3 hours. All cells were then harvested and tested for levels of active caspase 3. (E) TNFα- and TRAIL-Induced NFκB Activation. Cells transfected with the NFκB-luciferase reporter were serum-deprived and then subjected to mock, TNFα, TRAIL or zVAD treatments for 5 hours. Cells were then lysed and tested for levels of luciferase activity. Activity is presented as the levels of luciferase activity under treatment over the levels of activity under no treatment.

Results in FIG. 7 showed a clear correlation between the endogenous expression of IG20 and apoptosis. To study the effects of expression of IG20 variant on cells that do not naturally express it, PA-1, a human ovarian carcinoma cell line that expresses DENN-SV and MADD but not IG20 splice variant was used (FIG. 10).

IG20 caused PA-1 cells to grow at a rate 10 times slower than untransfected PA-1 cells (FIG. 12A). Additionally, IG20 renders PA-1 cells more susceptible to TNFα-induced apoptosis (FIG. 12B). More profound differences were seen with TRAIL (tumor necrosis factor-related apoptosis inducing ligand) treatment. PA-1 cells were almost completely resistant while PA-1-IG20 cells were highly susceptible to TRAIL-induced apoptosis (FIG. 12C). Interestingly, transfecting PA-1 cells with IG20 led to a ten-fold increase in spontaneous apoptosis overcells transfected with a control plasmid (10% vs. 0.98%). Similarly, IG20 rendered PA-1 cells more susceptible to treatment with radiation in combination with TRAIL (FIG. 12D).

Because IG20 not only enhanced cell death induced by different agents, but also suppressed cell proliferation, a question was whether cell survival signaling pathway was affected. The effects of IG20 on NFκB activation upon TNFα treatment. (FIG. 12-E) clearly showed that IG20 suppressed TNFα-induced activation of NFκB, compared to control cells.

Figure 2:
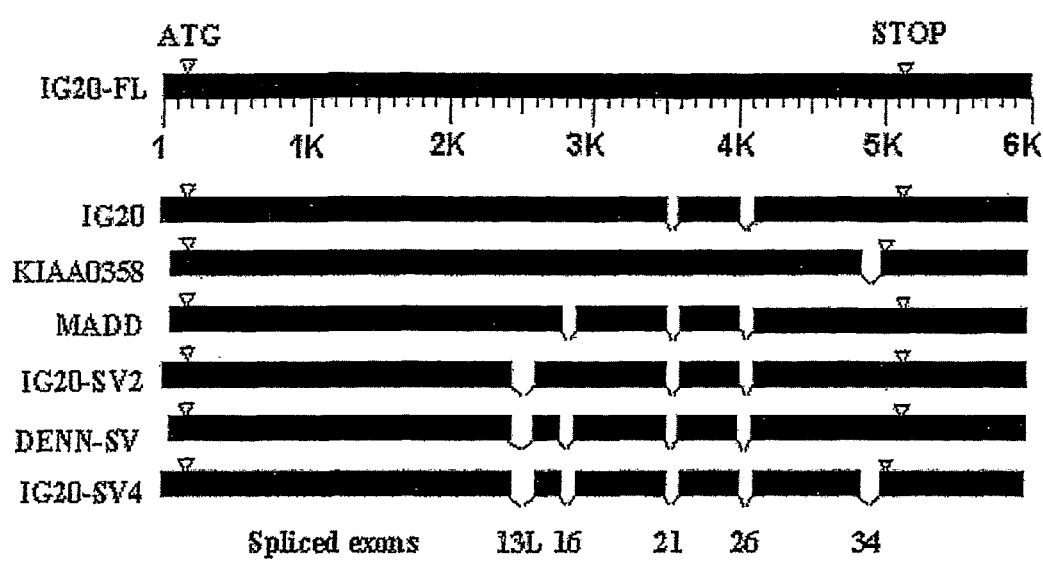
FIG. 2: Human IG20 splice variants generated by alternative mRNA splicing. The cDNA sequence homology among the seven IG20 splice variants is shown. Solid bars represent regions of complete homology between all variants. Empty areas indicate exons 13L, 16, 21, 26 and 34, which, when spliced in different combinations, produce the seven splice variants shown on the left. Splicing of exon 34 in KIAA0358 and IG20-SV4 induces an early stop codon in exon 35. Shown also are different 5' untranslated regions (UTRs) for different splice variants.

As shown in FIG. 2, only IG20, MADD, IG20-SV2 and DENN-SV, and not KIAA0358, IG20-SV4 and IG20-FL, are expressed in human tissues and could be of physiological relevance. The four variants expressed in human tissues arise from deletion of exons 21 and 26 (with the exception of a malignant pancreas) along with deletion of either exon 13L or 16, or both.

HeLa cells were permanently transfected with each of the four IG20 variants and showed the over expression of each of the four variants using a one-step internally controlled RT-PCR that simultaneously compares expression levels of all the four IG20 variants. Expression of the corresponding proteins were shown using anti-His antibodies.

Cells transfected with IG20 and DENN-SV were most susceptible and resistant to TNFα-induced apoptosis respectively, whereas cells transfected with MADD or IG20-SV2 did not show significant differences relative to cells transfected with a control plasmid. Because DENN-SV lacks both exons 13L and 16, MADD lacks exon 16 and IG20-SV2 lacks exon 13L, these results demonstrated that expression of both exons 13L and 16, as seen in IG20, is required for antiproliferative and pro-apoptotic properties, whereas deletion of both exons, as seen in DENN-SV, is required for proproliferative and anti-apoptotic properties.

Differences in the expression of different variants were not due to indirect inhibitory effects of protein synthesis by cyclohexamide, since there was no significant difference between cells that were either untreated or treated with cyclohexamide alone. Another important implication of these results is that they provide a possible explanation as to why maximal pro-apoptotic or anti-apoptotic effects are not observed in a heterogeneous HeLa cell population that is transfected with IG20 or DENN-SV respectively. This could also be due to mutual regulation of the function of IG20 and DENN-SV that are naturally co-expressed, albeit, at different levels in HeLa cells.

The effects of IG20 and DENN-SV on the apoptotic response to common cancer treatments showed HeLa-IG20 and HeLa DENN-SV cells were more susceptible and resistant respectively to vinblastine and TNFα treatment. However, HeLa-IG20 cells and HeLa-control cells showed a similar response to etoposide-induced apoptosis and yet had a fewer number of cells at the end of the observation period. This suggested that etoposide treatment might have suppressed the ability of HeLa-IG20 cells to proliferate. Cell proliferation data showed that HeLa-IG20 cells had reduced growth, compared to HeLa-control cells. Together, these results suggest that the apparent resistance of HeLa-DENN-SV cells to etoposide treatment is due to a combination of enhanced resistance to apoptosis and increased cell division, whereas the sensitivity of HeLa-IG20 is mainly due to a decreased rate of cell division.

HeLa-DENN-SV and HeLa IG20 showed greater and reduced proliferation respectively, relative to control cells. There was a difference in the anchorage-independent growth of both HeLa-DENN-SV and HeLa-IG20 cells compared to HeLa-control. DENN-SV cells formed higher numbers of larger colonies in soft agar indicating enhanced anchorage-independent growth. In contrast, HeLaIG20 cells showed reduced growth and formed smaller as well as fewer numbers of colonies in soft agar. These results provided further evidence of the contrasting effects of IG20 and DENN-SV on proliferation and cell survival.

The effects of expressing IG20 variant in cells of PA-1 human ovarian carcinoma cell line that do not naturally express it were examined. Relative to PA-1 cells, PA-1-IG20 cells showed significantly reduced proliferation and were much more susceptible to spontaneous, TNFα- and TRAIL induced apoptosis. These cells were even more susceptible to a combined treatment with TRAIL and γ-radiation. Of interest is the finding that TRAIL, a member of the TNF superfamily, can induce apoptosis in some tumor cells but not in others. This raises the possibility that IG20 could be used to render cells that are otherwise resistant to become susceptible (as seen with PA-1 cells) to TRAIL-induced cell death, and could have significant implications for cancer therapy. Percentages of cells with active caspases were somewhat less in PA-1 cells treated with 12 Gy+TRAIL relative to those treated with lesser doses (6 or 8 Gy+TRAIL).

In conclusion, results presented in this example provide a comprehensive analysis of alternative splicing of IG20 gene and its differential expression in human normal and tumor tissues. There is clear evidence to suggest that IG20 and DENN-SV have contrasting effects on apoptosis and cell proliferation.

Example 2

IG20 (MADD Splice Variant 5) a Proapoptotic Protein Interacts with DR4/DR5 and Enhanced TRAIL Induced Apoptosis by Increasing Recruitment of FADD and Caspase-8 to the DISC HeLa Cells Transfected Stably with IG20 Show Enhanced Susceptibility to TRAIL Induced Apoptosis—The degree of TRAIL induced apoptosis was determined using several different approaches, which included activation of caspases, mitochondrial depolarization and chromatin condensation. HeLa cells stably transfected with either IG20 or a control vector were treated with TRAIL for five hours. Earlier studies from the inventors' laboratory have shown that this duration of treatment is optimal for analysis of all three different cell death markers. As indicated in FIG. 13A, HeLa IG20 cells showed increased total caspase activation as determined by the binding of the broad spectrum caspase inhibitor, Z-VAD conjugated to FITC, increased mitochondrial depolarization as detected by the dye TMRE (FIG. 13B) and higher percentage of cells that were positive for Hoechst staining indicating chromatin condensation (FIG. 13C). A similar increase in apoptosis of IG20 cells upon treatment with TNF-α and cycloheximide was observed. There was, however, an approximate 3-3.5-fold increase in cells undergoing apoptosis after TRAIL treatment relative to only a two-fold increase after TNF-α treatment. IG20 can enhance TRAIL induced apoptosis to a higher magnitude relative to the enhancement seen after TNF-α and cycloheximide treatment.

Control and IG20 Stably Transfected Cells Display Similar Surface Expression of Trail Receptors—Differential susceptibility of normal primary cell lines versus transformed cell lines to TRAIL was initially attributed to the presence of at least one decoy receptor in normal cells, but its absence in tumor cell lines. The DcR1 and DcR2 decoy receptors attenuate TRAIL induced signaling by competing for the ligand binding to DR4 and DR5. Therefore, the relative levels of expression of different TRAIL receptors could profoundly affect the ability of TRAIL to induce apoptosis. To rule out the possibility that IG20 may affect the levels of expression of these receptors, surface expression was analyzed. As seen in FIG. 14A, the levels of expression of all four receptors were comparable in both control and HeLa IG20 cells, indicating that stable expression of IG20 had no significant effect on the surface expression of various TRAIL receptors.

Receptor Stability in IG20 HeLa Cells—a delay in the death receptor turn over could accentuate sensitivity of HeLa cells to TRAIL induced apoptosis. In order to test the possibility that HeLa IG20 cells might have a slower rate of receptor turnover than the controls, cells were treated with Brefeldin A, which blocks Golgi function and prevents receptor replenishment on the cell surface. Treatment of both HeLa IG20 and control cells with Brefeldin A showed no difference in the stability of DR5 on the cell surface (FIG. 14B) either at three or six hours, indicating that differences in the rate of receptor turnover was not responsible for the enhanced apoptosis of HeLa IG20 cells.

HeLa IG20 cells show increased activation of initiator and effector caspases—Addition of TRAIL results in receptor clustering, which facilitates FADD and caspase-8 recruitment leading to effector caspase-3 activation. In order to analyze whether IG20 mediated its effects by increasing activation of caspases, levels of caspase-8, were tested which is the main activator caspase involved in TRAIL mediated death pathway. Caspase-10, a molecule with sequence similarity to caspase-8 has been shown to participate with caspase-8 in the DR4 and DR5 signaling pathways and therefore their levels in TRAIL treated cells were determined. As seen in FIG. 15A, the levels of both caspases, measured in fluorescence intensity, increased in TRAIL treated HeLa IG20 cells compared to TRAIL treated control cells. Cleavage of ProCaspase-8 results in active caspase-8 and a 10 kDa fragment (p10) that can be readily detected in a western blot using a p10 specific antibody. An increase in the amount of cleaved caspase-8 is seen in HeLa IG20 cells relative to the control cells tested at different timepoints after TRAIL treatment (FIG. 15B). The blot was also stripped and reprobed with anti-β-actin to ensure equal protein loading.

Activated caspase-8 could cleave cytoplasmic Bid, which can subsequently translocate to the mitochondria leading to activation of the mitochondrial pathway and caspase-9. Therefore, for caspase-9 activation was tested and consistent with the results obtained from TMRE staining (FIG. 13B), upon TRAIL treatment, activation of caspase-9 was increased in HeLa IG20 cells relative to control cells (FIG. 15A).

Caspase-3, the main downstream effector caspase, is activated either directly by active caspase-8, or indirectly through Bid cleavage leading to the activation of mitochondrial pathway and caspase-9. The levels of active caspase-3 in HeLa IG20 as well as control cells were measured by staining treated cells with a specific anti-active caspase-3 PE conjugated antibody. As seen in FIG. 15C, IG20 HeLa cells showed considerably higher levels of caspase-3 activation relative to control cells. The relative increase in caspase-3 activation was more profound in TRAIL treated HeLa IG20 cells relative to control cells (five fold increase), when compared to cells treated with TNF-α (less than two fold increase). These results show that IG20 can promote activation of caspases-8 and -10 on one hand and caspase-9 on the other, perhaps both contributing to the activation of caspase-3 and enhanced apoptosis.

Figure 16:
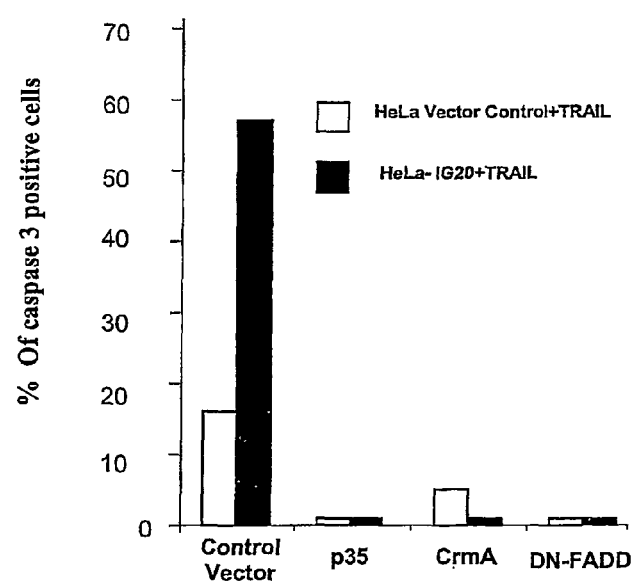
FIG. 16. IG 20 enhanced apoptosis can be inhibited by caspase inhibitors and DN FADD HeLaIG20 and control cells ($1\times10^5$ per well in a 6 well plate) were co-transfected with GFP-F vector along with either Crm A, p35 or DN-FADD in the ratio of 1:10. Twenty-four hours post transfection, TRAIL was added at a concentration of 100 ng/mL for 5 hours and both treated and untreated cells were stained with PE-conjugated anti-caspase3 antibodies and subjected to FACS analyses. The data were obtained from only GFP positive cells and represent 2 independent experiments carried out in duplicate.
Figure 17:
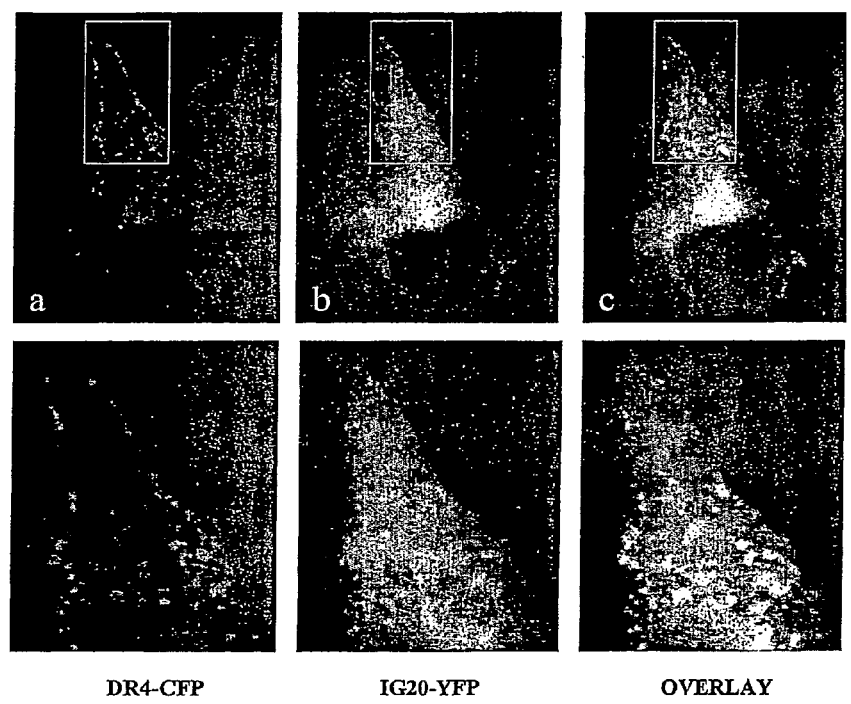
FIG. 17: IG20 co-localizes with DR4 in HeLa cells HeLa cells were co-transfected with IG20-YFP and DR4-CFP (5:1) in two-chamber culture slides. 10 μM Z-VAD was added after 12 hours of transfection to prevent apoptosis and cells were observed under the Delta Vision deconvolution microscope under a 100× magnification. The deconvolved z-stack image of a single HeLa cell expressing DR4-CFP, IG20-YFP and the merged image which indicates co-localization of the expressed proteins. The inset, shown in the lower panel, indicates the magnified region on the stained cell surface.
Figure 18:
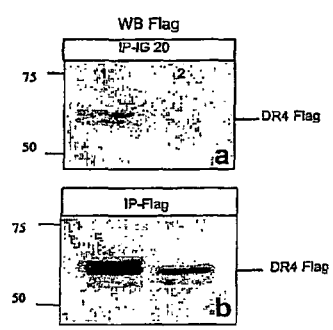
FIG. 18: IG 20 interacts with DR4 and DR5 receptor A) 293T cells were transfected with DR4-Flag and IG20-His (lane 1) or DR4-Flag alone (lane 2). IG20 antibody (panel a) or Flag antibody (panel b) was used to IP the lysates from the transfected cells and Flag antibody was used for the western blot (WB) on all samples. B) DR5-Myc was co-transfected with IG20-His and an IG20 antibody (lane 1) or a Myc antibody (lane 2) was used to IP the cell lysates and subjected to WB. Proteins were visualized using either a His (panel a) or a Myc (panel b) antibody. C). IG20-GFP (construct shown in FIG. 18E) was transfected along with DR4-Flag (panel a) or alone (panel b). A Flag (lane 1), or an IG20 (lane 2), antibody was used to IP the lysates. Proteins were visualized on WB using a GFP antibody. D). IG20-GFP was transfected alone (lane 1) or with DR5-CFP (lane 2) and IG20 antibody was used to IP the lysates (lane 1, 2). Cells were transfected with DR5-CFP alone and DR5 antibody was used to IP the transfected lysates (lane 3). Proteins were visualized using a GFP antibody in WB (GFP antibody also reacts with CFP).
Figure 18:
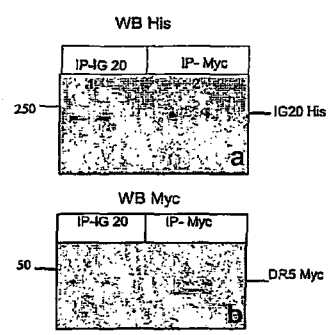
Figure 18:
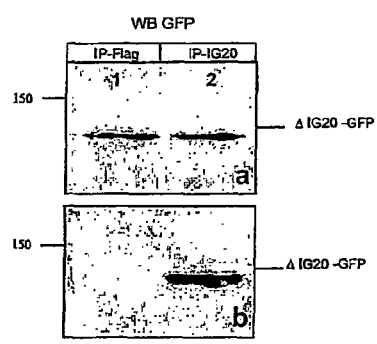
Figure 18:
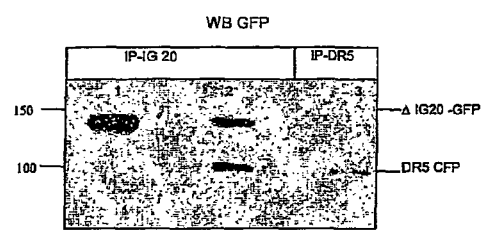
Figure 18:
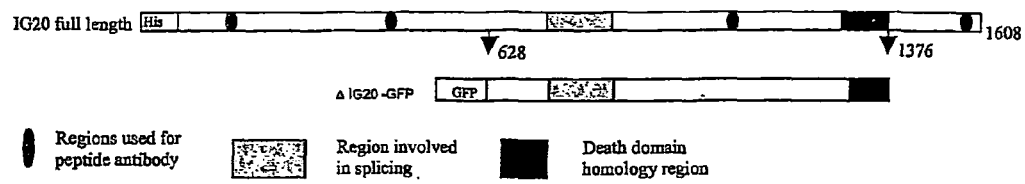
Figure 19:
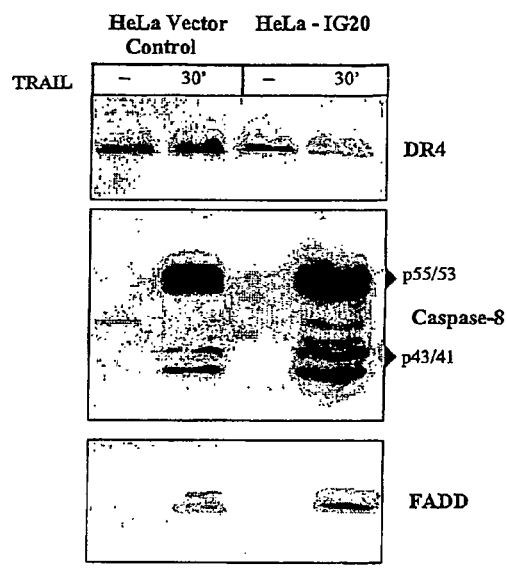
FIG. 19: Enhanced recruitment of caspase-8 into the DISC of HeLa IG20 cells. HeLa IG20 and control cells ($1\times10^7$) were collected and treated with 1 μg/mL of TRAIL for the indicated duration. Lysates from treated as well as untreated cells were normalized for protein content and the DISC was precipitated using a DR4 (A) or a DR5 (B) specific antibody. The immunoprecipitated samples were then immunoblotted using antibodies specific for caspase-8, FADD, DR4 or DR5. All blots were developed with ECL and exposed to the film for the same duration.
Figure 19:
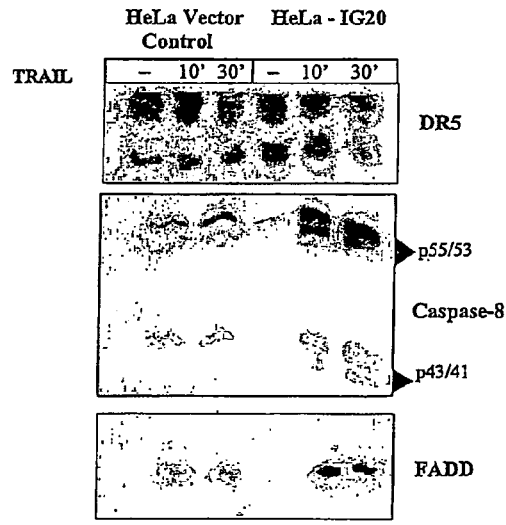

TRAIL induced apoptosis can be inhibited by caspase inhibitors and DN-FADD—There was increased activation of caspases in HeLa IG20 cells relative to control cells after TRAIL treatment. In order to further confirm the necessity of caspases for enhanced apoptosis in HeLa IG20 cells, and to begin to identify the potential site of action of IG20 in the signaling pathway, caspase inhibitors, p35, a baculovirus derived general caspase inhibitor and CrmA, a poxvirus protein that can inhibit caspase-8 and -1 preferentially were used. Both p35 and CrmA abrogated TRAIL induced apoptosis in both control as well as IG20 cells (FIG. 16). FADD is an essential upstream adaptor molecule that is required for the recruitment of casapase-8 in TRAIL induced apoptosis. Therefore, the levels of active caspase-3 were assessed as a marker of apoptosis in control and HeLa IG20 cells transfected with a DN-PADD and these cells were almost completely resistant to TRAIL induced apoptosis (FIG. 16). Since both the caspase inhibitors and the DN-FADD rendered HeLa IG20 cells highly resistant to TRAIL induced apoptosis, the function of IG20 in TRAIL induced apoptosis required functional caspase-8.

IG20 co-localizes with DR4 in HeLa cells—Caspase-8 and FADD are two signaling molecules that are proximal to DR4/DR5 and are required for TRAIL induced apoptosis. IG20 does not interact directly with FADD (23), but requires intact FADD and caspase-8 to mediate its effects. In addition, IG20 DD has a high homology to the DDs of DR4 and DR5. Co-localization studies were conducted using IG20-YFP and DR4-CFP constructs. These proteins were expressed in 293T cells and immunoblotted using a GFP antibody to check for spontaneous cleavage of the fluorescent tags. Both constructs expressed expected size fusion proteins with no detectable cleavage of either YFP or CFP. Over expression of death receptors in vivo results in spontaneous oligomerization resulting in apoptosis of cells. Similarly, the DR4-CFP construct caused apoptosis when over expressed in HeLa cells. To minimize spontaneous cell death due to receptor over expression, levels of expression were optimized by lowering its ratio with respect to IG20-YFP in co-transfection experiments. As seen in FIGS. 17A and B, both fusion proteins were simultaneously expressed in the cotransfected HeLa cells. The expression of DR4-CFP is restricted mostly to the membrane, but also is found in the cytoplasm as indicated by a series of Z-stack pictures captured in the CCD camera. FIG. 17C is an overlay image, which demonstrates that the two proteins are co-localized.

DR4 and DR5 interact with full length and the middle fragment of IG20—To more directly demonstrate that IG20 can interact with DR4 and DR5 and to further extend the co-localization data, 293T cells were co-transfected with the IG20-His and a DR4-Flag or a DR5-Myc construct. Immunoprecipitation of lysates from transiently transfected 293T cells was carried out using either a polyclonal IG20 peptide antibody or a Flag specific antibody. As seen in FIG. 18A, immunoprecipitate (IP) using an anti-IG20 peptide antibody from lysates of IG20-His and DR4-Flag co-transfected cells (panel a, lane 1), but not of cells transfected with DR4-Flagalone (panel a, lane 2), showed association of DR4-Flag protein with IG20. Similarly, Myc specific antibody co-precipitated IG20-His (FIG. 18B, panel a, lane 2) and the IG20 antibody immunoprecipitated DR5-Myc (FIG. 18B, panel b, lane 1) from lysates of cells co-transfected with IG20-His and DR5-Myc, suggesting that IG20 can interact with DR5. In order to further confirm these results, a GFP fusion construct of IG20, that contains all the splice sites observed to date at the N-terminal end and the death domain at the C-terminal end (FIG. 18E) was used. As seen in FIG. 18C, the 125 kDa IG20-GFP was immunoprecipitated using the Flag specific antibody only from lysates of cells co-transfected with IG20-GFP and DR4-Flag (FIG. 18C, panel a, lane 1), but not from IG20 transfected cells alone (FIG. 18C, panel b, lane 1). Immunoprecipitation of lysates from cells co-transfected with IG20-GFP and DR5-CFP with IG20 antibody showed the presence of both proteins confirming that IG20 interacts with DR5 (FIG. 18D, lane 2). Together these results showed that IG20 interacts with both DR4 and DR5 and the IG20 domain that interacts with the DRs lies within the 748 amino acid residues that constitute IG20.

Recruitment of Caspase-8 and FADD to the DR4 and DR5 DISC is increased in HeLaIG20 cells—TRAIL induced signaling through DR4 and DR5 results in the formation of DISC that contains FADD and Caspase-8, which are the main proximal initiators of apoptosis. Moreover, IG20 interacts with the DR4 and DR5. Therefore, one possible mechanism by which IG20 can render cells more susceptible to apoptosis is through enhanced TRAIL DISC formation. The TRAIL DISC was immunoprecipitated from lysates (equalized for protein) of control or HeLa IG20 cells using anti-DR4 and anti-DR5 antibodies after TRAIL treatment for the indicated periods of time. As seen in FIG. 19A, there is an increased recruitment of procaspase-8 into the DISC from HeLa IG20 cells relative to control cells. Furthermore, increased cleavage of procaspase-8 into its active p43/41 fragments was also evident. This effect was time dependent and correlated well with the previous results, which showed an increase in the processed p10 form of caspase-8 in HeLa-IG20 cells when compared to control cells (FIG. 15B). A similar increase was observed in the DR5 DISC from HeLa IG20 cells (FIG. 19B). Increased FADD recruitment to the DISC associated was observed with both DR4 and DR5 in HeLa IG20 cells relative to control cells. Although similar amounts of DR5 were immunoprecipitated from both cell types, there was considerable increase in the DISC components from HeLa-IG20 cells (FIG. 19B). In fact, the level of immunoprecipitated DR4 is lower in HeLa IG20 samples compared to control cells and yet it showed higher levels of caspase-8 recruitment (FIG. 19A).

IG20 can render cells more susceptible to TRAIL induced apoptosis primarily by increasing the recruitment of FADD and caspase-8 to the DISC that results in enhanced activation of caspase-8 and caspase-3. These observations are consistent with the results obtained using caspase inhibitors and DN-FADD and further support the notion that IG20 is modulating the TRAIL induced apoptosis by increasing DISC formation.

Figure 13:
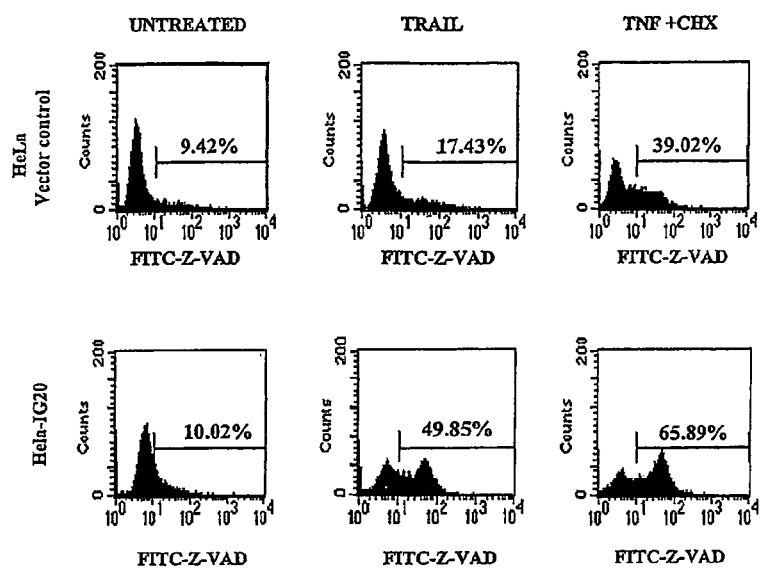
FIG. 13: IG20 transfected HeLa cells show increased apoptosis upon TRAIL treatment. HeLa-IG20 and control cells were treated for 5 hours with TRAIL at 100 ng/mL or with 10 ng/mL of TNF-α and 10 μg/mL of Cycloheximide and analyzed for apoptosis. A) Activation of caspases—cells were incubated for 10 minutes with FITC labeled general caspase inhibitor VAD FMK (Val-Ala-Asp-flouromethyl ketone) and analyzed by FACS. Numbers in the histogram indicate percentage of FITC positive cells. B) Mitochondrial Depolarization—Loss of the dye TMRE is indicative of mitochondrial depolarization and the numbers shown in the FACS histograms represent percentage of TMRE negative cells. All the above experiments were done in triplicates and results shown are representative histograms. C) Hoechst staining—Cells were stained with Hoechst (1 μg/mL) for 10 minutes. Brightly stained nuclei indicate condensed chromatin. D) Percentage of cells with condensed chromatin was calculated by counting 3 fields containing at least 200 cells each and error bars indicate mean±S.D.
Figure 13:
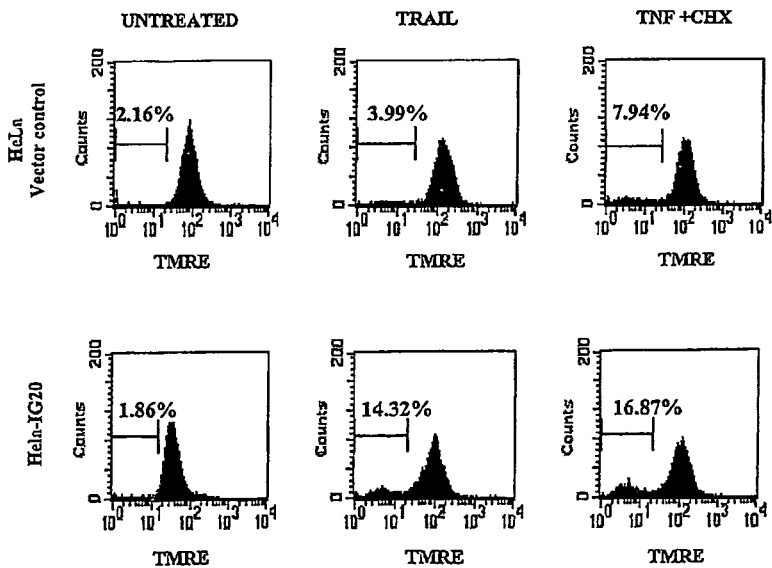
Figure 13:
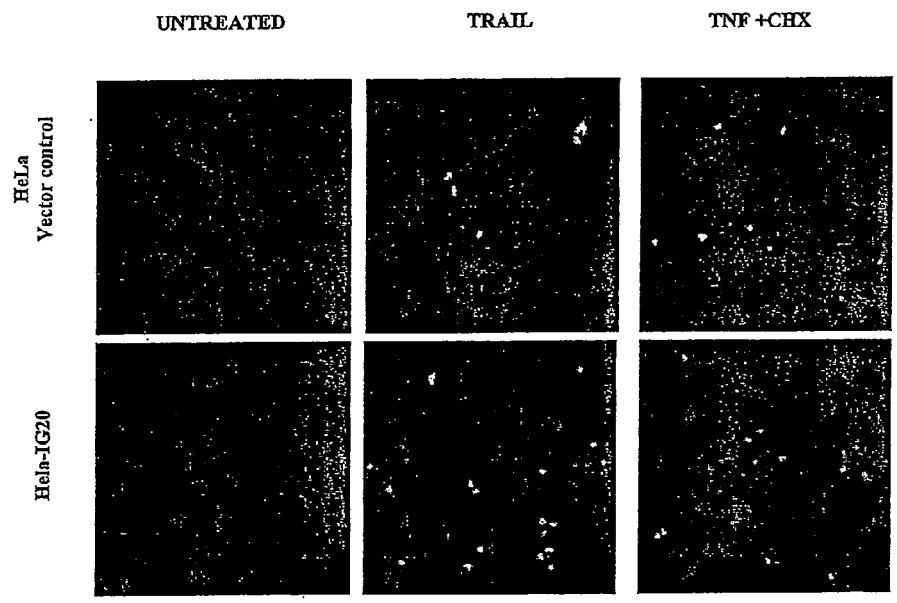
Figure 13:
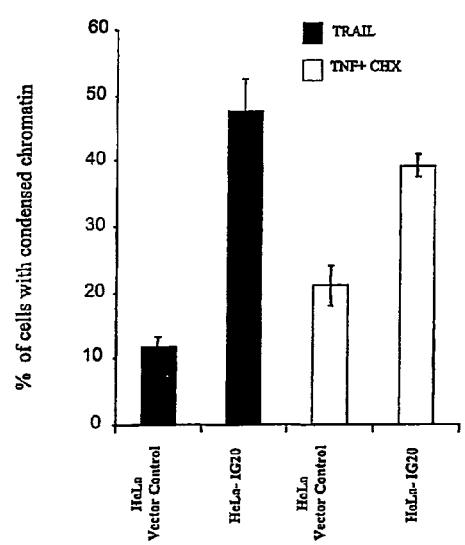
Figure 14:
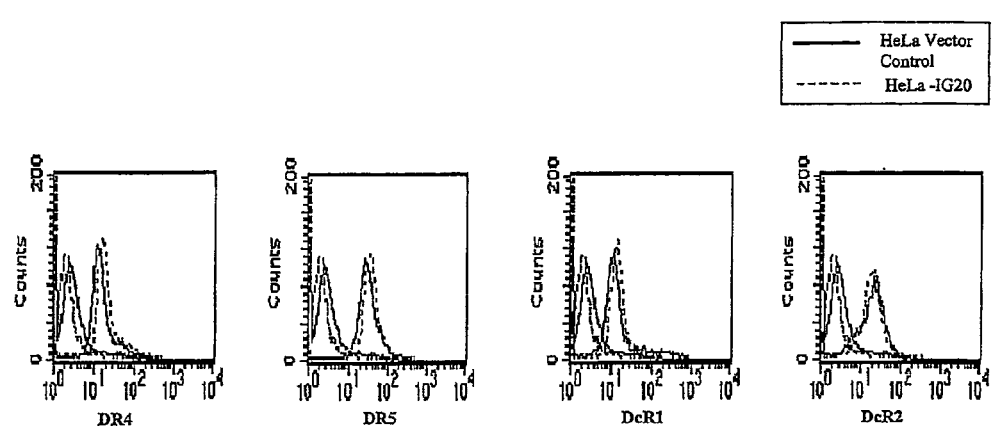
FIG. 14: Relative expression and stability of TRAIL receptors in HeLa IG20 cells A) DR and DcR expressions—HeLa IG20 and control cells were stained with antibodies conjugated to FITC that specifically react with DR4, DR5, DcR1 and DcR2 (peaks shifted to the right), or isotype matched control antibodies, and analyzed by FACS. B) Brefeldin A treatment—Equal number of control and IG20 HeLa cells were left untreated or treated with 1 μg/mL of Brefeldin A for either 3H or 6H. Cells were stained for DR5 surface expression. Representative histograms show comparable levels of DR5 surface expression in Brefeldin A untreated and treated cells.
Figure 14:
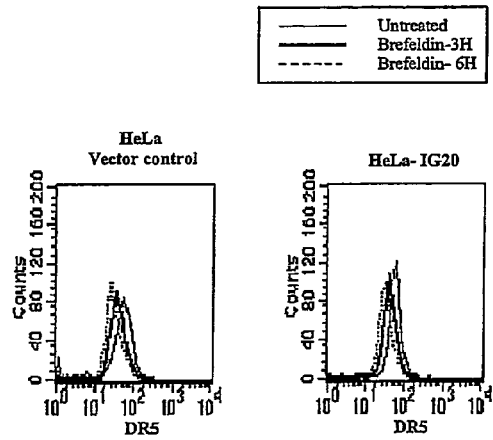
Figure 15:
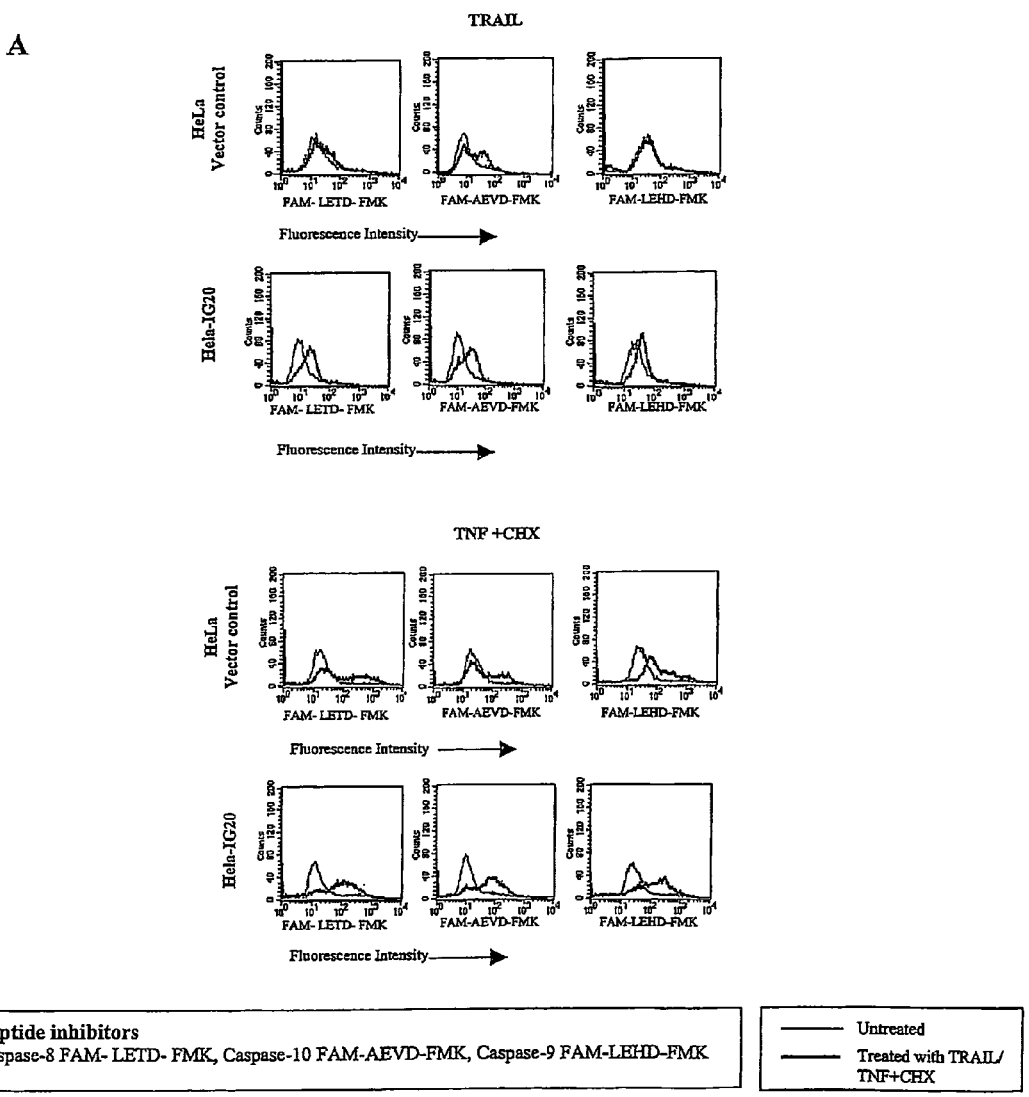
FIG. 15: IG20 Cells show increased specific activation of caspases upon TRAIL treatment A) Initiator caspases—Hela IG20 cells and control cells treated with TRAIL for 1H, were stained, with flourochrome-conjugated peptide inhibitors of specific active caspases as indicated, fixed and analyzed by FACS. B) Caspase-8 cleavage—IG20 HeLa cells and control cells were treated with TRAIL for either 1H or 3H, lysed and immunoblotted for the 10 kDa cleaved product of active caspase-8 using the 6B6 monoclonal antibody. C) Caspase-3 activation—Hela IG20 cells and control cells untreated or treated with TRAIL or TNF-α and cycloheximide for 5 hours, were collected, fixed and stained with an active caspase-3 Phycoerythrin (PE) conjugated monoclonal antibody and subjected to FACS analyses. Above data are representative of 3 experiments. LETD, AEVD and LEHD disclosed as SEQ ID NOS 10-12, respectively.
Figure 15:
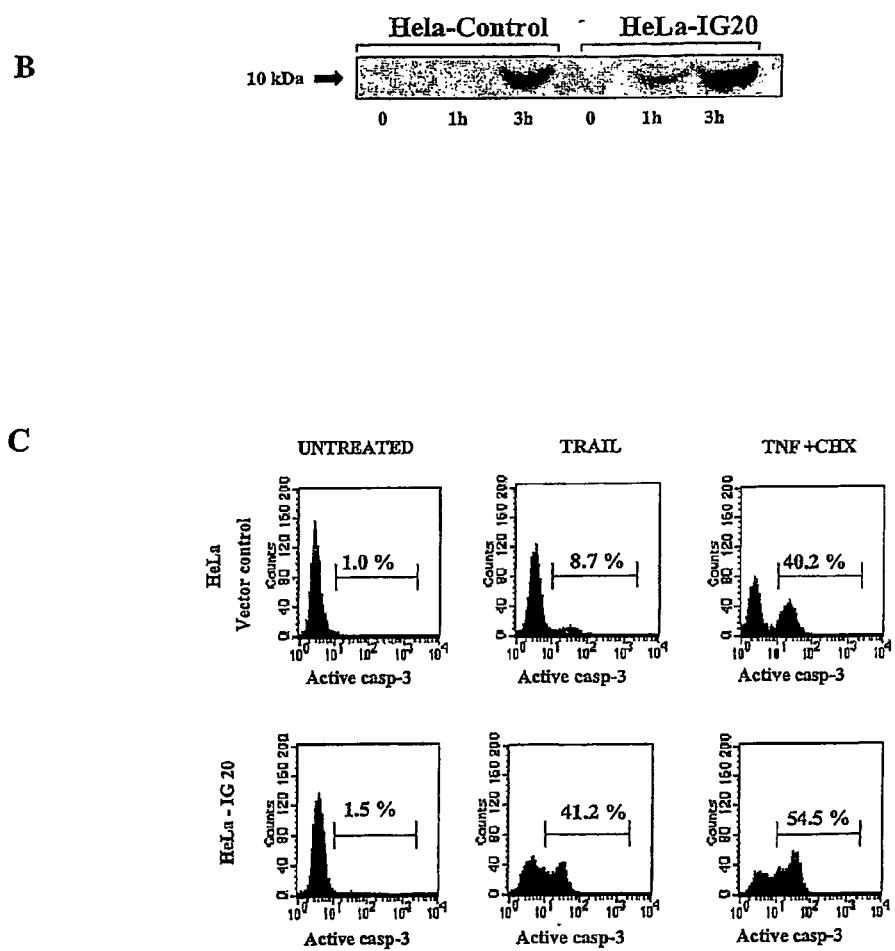

Apoptosis is characterized by universal activation of caspases. IG20 increased TRAIL induced caspase activation substantially relative to the levels seen in control cells. This was further confirmed by increased mitochondrial depolarization and increased chromatin condensation, which are hallmarks of apoptosis (FIG. 13). Cell surface expression of the DRs and DcRs were at comparable levels in HeLa IG20 and control cells. Similarly, there was no significant difference in the turnover of the surface receptors (FIG. 14). Therefore, the enhanced susceptibility of HeLa IG20 could not be accounted for by the differential surface expression or turnover of DRs or DcRs.

A considerable increase in not only caspase-8 and -10, but also in caspase-9, which is primarily activated by the mitochondrial pathway, was seen in HeLa IG20 cells (FIG. 15A). Flourochrome-conjugated peptide inhibitors were used to detect activation of specific caspases. The caspase-8 activation was corroborated, by detecting its cleaved p10 fragment, using a specific antibody (FIG. 15B). Downstream effector caspases can be activated either by caspase-8 directly (Type I response) or indirectly through Bid cleavage, resulting in the activation of caspase-9 through the mitochondrial pathway (Type II response), or both. Activation of the mitochondrial pathway, although first described in CD95 mediated signaling, is now implicated in TRAIL induced apoptosis where the susceptibility of certain cancer cells to apoptosis is dependent upon the presence of smac/DIABLO and Bax. Similarly, caspase-10 can participate along with caspase-8 in DR4 and DR5 signaling pathway. One of the known consequences of activation of initiator caspases, like caspases-8, -10 and -9, is that they all can activate the downstream effector caspase-3. An increase in caspase-3 was evident in HeLa IG20 cells.

Due to its broad effect, p35 can protect against death receptor as well as stress-induced mitochondria mediated apoptosis. Expression of p35 in HeLa cells with and without IG20 totally blocked TRAIL induced apoptosis, most likely by inhibiting relevant caspases. On the other hand, CrmA can protect cells from undergoing TNF-α and CD95 ligand induced apoptosis by primarily inhibiting caspase-8. Although HeLa IG20 cells showed enhanced activation of caspases-8, -9 and -10, CrmA inhibited TRAIL induced apoptosis almost completely (FIG. 16) and strongly supported the notion that IG20 can enhance TRAIL induced apoptosis primarily through enhanced activation of caspase-8.

IG20 pro-apoptotic splice variants can enhance TNF-α induced apoptosis through increased activation of caspase-8. IG20 has a similar effect on TRAIL induced caspase-8 activation. Collectively, these studies show that IG20, like FADD and caspase-8, is involved in the signaling pathway of more than one member of the TNF super family.

FADD is necessary for caspase-8 recruitment to the TRAIL DISC. Therefore, a DN-FADD was used to prevent FADD, and subsequent caspase-8 recruitment and showed that it could suppress TRAIL induced apoptosis in HeLa-IG20 cells. Similarly, FADD cannot directly interact with IG20, and yet a total abrogation of apoptosis in DN-FADD transfected cells was observed (FIG. 16). These observations raised the possibility that IG20 could be acting upstream of FADD perhaps through direct interactions with the DRs. Results from co-transfection of fluorescently tagged DR4 and IG20 showed co-localization of these two proteins in HeLa cells. Moreover, co-immunoprecipitation of death receptors and IG20 showed that they interact with each other.

CD95L and TRAIL induced signaling results in DISC formation characterized by the recruitment of FADD and caspase-8. Subsequent to TRAIL treatment, there was not only an increased recruitment of FADD and caspase-8 to the DISC in HeLa IG20 cells but also an increase in cleaved caspase-8. Furthermore, a significant increase in FADD recruitment to the DISC was found earlier after TRAIL treatment in HeLa IG20 cells, relative to the levels seen in the control cells. The levels or presence of caspase-10, were not tested since it has been shown that even though caspase-10 is recruited to DR4 and DR5, it does not functionally substitute for caspase-8. Moreover, near complete inhibition of apoptosis in the presence of CrmA also indicated that caspase-8 was sufficient for TRAIL induced apoptosis of both HeLaIG20 and control cells.

IG20 is a pro-apoptotic protein that can interact with DR4 and DR5 and significantly enhance TRAIL induced apoptosis by facilitating DISC formation with increased recruitment of FADD and caspase-8.

Example 3

IG20, a MADD Splice Variant, Increases Cell Susceptibility to γ-irradiation and Induces Soluble Mediators that Suppress Tumor Cell Growth HeLa cells were stably transfected with either a vector control, DENN-SV and IG20. Equal numbers of cells were treated to 6, 8, 10 and 12 Grays of γ-irradiation, plated and then allowed to grow for 2 weeks, after which they were stained with crystal violet. Transfected HeLa cells began responding differently at 8 Grays of irradiation and this difference increased with the doses. A representative experiment (FIG. 20) demonstrates the effect of 12 Grays of irradiation on each of the transfected cell lines. HeLa DENN-SV cells were highly resistant, while HeLa IG20 cells were more susceptible, to the effects of irradiation as compared to control cells.

To determine whether the effects of γ-irradiation on HeLa IG20 growth was primarily due to enhanced susceptibility or due to reduced cell proliferation. IG20 and control cells were exposed to different amounts of γ-irradiation and then the percentage of cells undergoing apoptosis was assayed by measuring active caspase 3. As shown in FIG. 20C, there was a relatively small difference between the degrees of apoptosis seen, after γ-irradiation, in HeLa IG20 cells, as compared to controls (approximately 10%). This indicated that the reduced number of HeLa IG20 colonies (FIG. 20B), relative to controls, cannot be accounted for by apoptosis alone. Therefore, the effects of IG20 and DENN-SV on the growth properties of HeLa cells were evaluated.

Equal numbers of HeLa control, IG20 and DENN-SV cells were plated and then counted every other day for a total of 9 days. As seen in FIG. 21A, there was a significant difference in the numbers of cells over the nine day period. The HeLa DENN-SV cell numbers were dramatically increased, while the number of HeLa IG20 cells was lower relative to controls.

To confirm that the differences in cell numbers seen in FIG. 21A, were due to differences in their growth rate and not due to differences in cell death, to determine the relative rate of cell division, the CFSE dye was used to stain the intracellular protein content of these cells. As the cells divide, the CFSE intensity decreases by half, which can then be assayed for by flow cytometry. As can be seen in FIG. 21B, there is a reduced dilution of CFSE in the HeLa IG20 cells as compared to the control and HeLa DENN-SV cells. This indicated a lag in the division time of the HeLaIG20 cells compared to the other two cells and demonstrated that the differences in the numbers of cells seen in the growth curve is due, to a significant extent, to differences in the rate of cell division. These results show that IG20 renders cells more susceptible to the apoptotic effects of γ-irradiation and slows the rate of cell division.

Interestingly, the growth curve seen in FIG. 21A demonstrates a biphasic mode. Early on, all three cells demonstrated similar growth but subsequently they showed divergence. This suggested that the effects on cell proliferation might depend on the accumulation of a critical factor(s) in the culture that either promotes (as in DENN-SV cells) or inhibits (as in IG20 cells) cell growth. To test this, trans well chamber experiments were carried out, which indicated that conditioned medium from IG20 transfected cells could suppress the growth of control as well as IG20 or DENN-SV transfected cells. However, conditioned media from the other two cells had no discernible effect on cell growth. This indicated that a soluble factor(s) secreted by HeLa IG20 cells may be responsible for slowing cell growth and that it could work in trans.

To confirm the above results, control, HeLa IG20 and HeLa DENN-SV cells were grown for 7 days to assess their growth. In parallel experiments, the culture medium of HeLa DENN-SV cells was replaced daily starting day 4 with corresponding conditioned medium (CM) from HeLa IG20 cell culture or CM from DENN-SV was used to replenish HeLa IG20 cells. The cells were allowed to grow for 3 more days (for a total of 7 days). Results showed that untreated HeLa IG20 and HeLa DENN-SV cells had half and twice the number of cells seen in controls respectively (FIG. 22A). HeLa DENN-SV cells treated with CM from HeLa IG20 cultures grew as slow as the HeLa IG20 cells. Replenishing HeLa IG20 cells with CM from HeLa DENN-SV cultures rescued cell numbers. The reduction in the number of cells was either due to cell death or differences in cell proliferation. To determine relative differences in the rate of cell replication, the cells were stained with CFSE and tested for dye dilution after treatment with different CM media. FIG. 22B shows the cell division rates normally seen in control, DENN-SV and IG20 cells. FIG. 22C shows the effects of reciprocal exchange of CM between HeLa DENN-SV cells and HeLa IG20 cells. The addition of HeLa IG20 CM to HeLa DENN-SV cells reduced their rate of cell division (FIG. 22C) while replacement of HeLa IG20 medium with CM from HeLa DENN-SV alleviated the reduction in cell division.

HeLa IG20 cells produce soluble factor(s) that could suppress its own growth as well as that of other HeLa cells. To see whether this effect could be seen when cells unrelated to HeLa cells were exposed to the CM from HeLa IG20 cells, the CM from confluent HeLa IG20 cells, but not from control or DENN-SV cells profoundly suppressed the cell growth of PA-1 ovarian cancer cells (FIG. 23A). This effect was again due to a reduction in cell growth and not enhanced apoptosis since these cells did not dilute their CFSE stain to the same extent as cells that were treated with CM from control or HeLa DENN-SV cells (FIG. 23B I, II, III).

Figure 24:
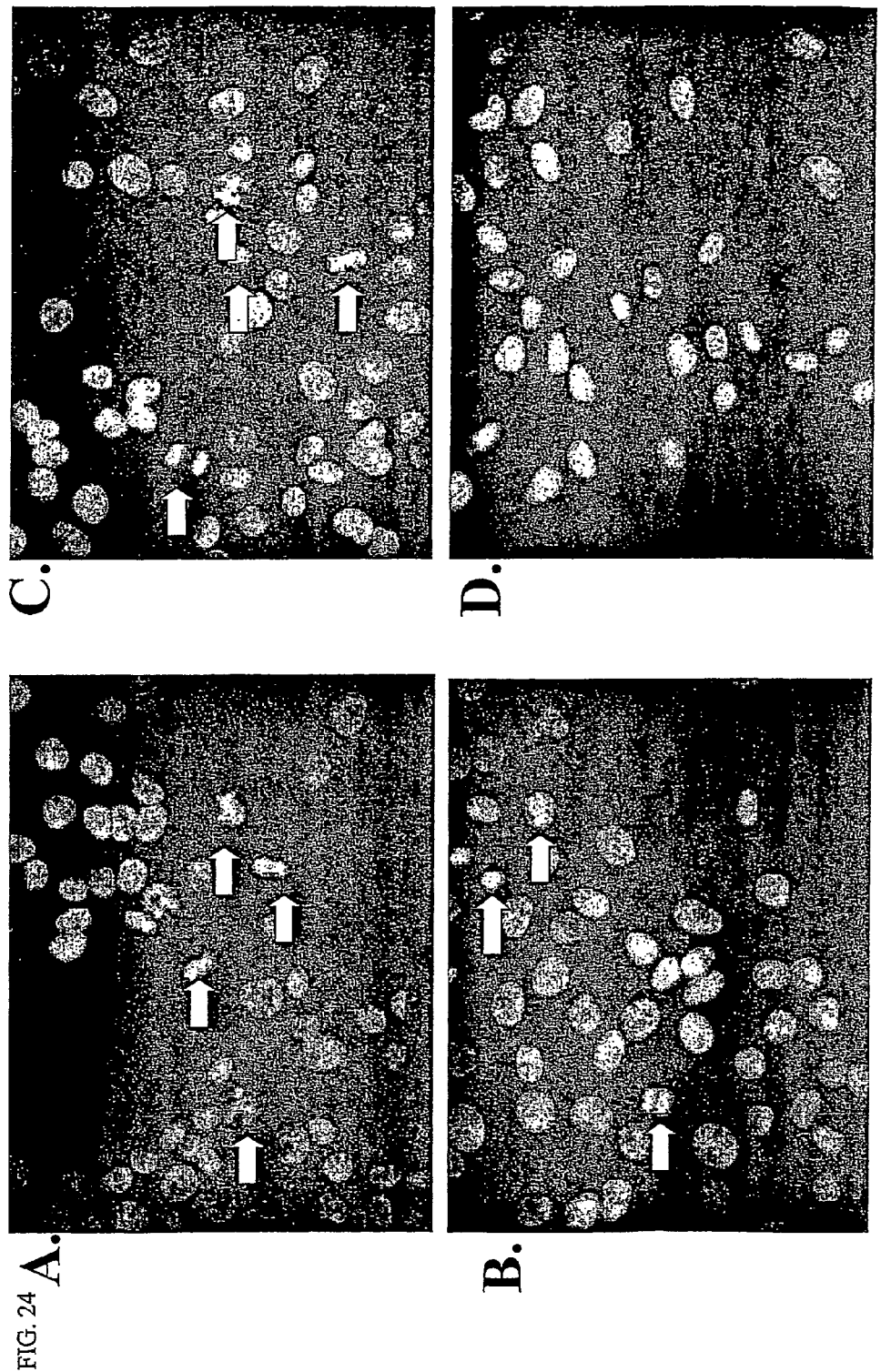
FIG. 24: The effects of CM from HeLa IG20 cells on mitosis of PA-1 cells. Representative pictures from DAPI stained PA-1 cells (A) grown in regular culture medium or in the presence of CM from (13) HeLa control, (C) HeLa DENN-SV and (D) HeLa IG20 cells for 24 hours. White arrows indicate cells undergoing mitosis.

FIG. 24 shows that mitotic bodies, as revealed by nuclear DAPI staining, are lacking in PA-1 cells treated with CM from HeLa IG20 cells. A total lack of PA-1 cell division was also corroborated using mpm2, a mitosis specific antibody. The PA-1 cells left un-treated or treated with CM from control HeLa, HeLa DENN-SV or HeLa IG20 cells for 24 hours were found to have 2.2%, 2.9%, 2.9% and 0% cells staining positive for mpm2, respectively. Cell cycle analysis (FIG. 25) showed that the PA-1 cells treated with CM from HeLa IG20 cells were growth arrested in the G1-G0 stage of the cell cycle.

To determine the identity of the soluble factor(s) produced by HeLa IG20 cells, culture supernatants from control and HeLa IG20 cells were subject to a multiplex assay to detect the presence of a variety of cytokines. There was a mild upregulation of many of the cytokines in the supernatant of HeLa IG20 cells as compared to the control cells, but IL-6 was significantly up regulated (~20 fold). The levels of IL-6 in CM from all three cell cultures and found a marked increase in only CM from HeLa IG20 cells and not from the other two. Although, FIG. 26A shows the amounts of IL-6 produced from cells grown in serum free media, the results are the same from cells grown in serum containing media. Because one of the more important transcription factors involved in the regulation of IL-6 is NF-κB, the basal levels of NF-κB were tested. Entirely consistent with the increased levels of IL-6 production, HeLa IG20 cells showed a significantly higher basal level of NF-κB activity relative to the other two cells (FIG. 26B).

Figure 27:
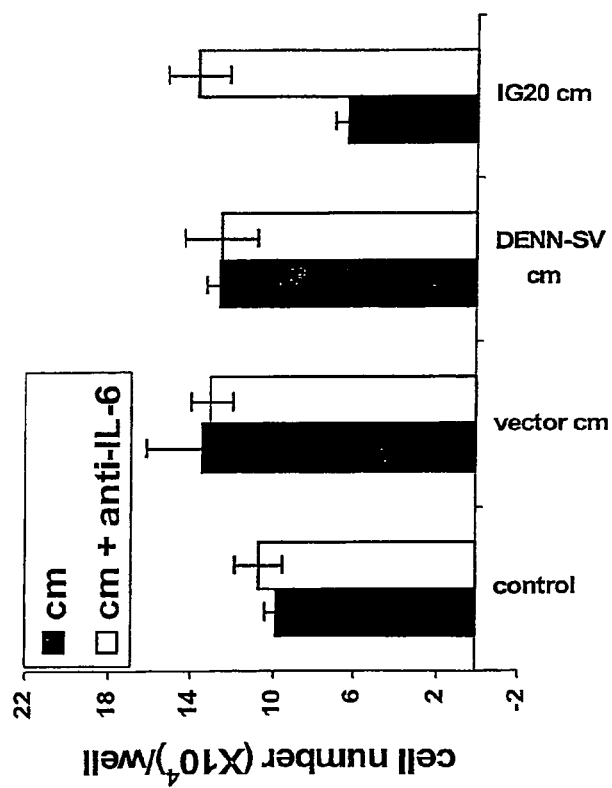
FIG. 27: Reversal of the effects of CM from Hela IG20 cells on cell growth using an IL-6 neutralizing antibody. PA-1 cells ($5×10^5$ cells/plate) were plated in 12 well plates. The next day, media were replaced with CM from control, HeLa IG20 and HeLa DENN-SV cells alone or along with neutralizing IL-6 antibody (50 µg/mL). 48 hours later, cells were harvested and counted.

To determine the potential contribution of IL-6 to the growth inhibiting property of the CM from HeLa IG20 cell culture, PA-1 cell growth was assayed in the presence of CM from HeLa IG20, HeLa DENN-SV and control cells treated with and without an IL-6 blocking antibody. FIG. 27 demonstrates that the PA-1 cell growth inhibition mediated by the CM from HeLa IG20 cells can be reversed by the addition of an IL-6 neutralizing antibody. However, the anti-IL-6 antibody had no effect on the growth patterns of the PA-1 cells grown in the presence or absence of CM from other cells. This demonstrated that the IL-6 was, at least in part, responsible for the cell growth inhibitory effects of the CM from HeLa IG20 cells.

Figure 28:
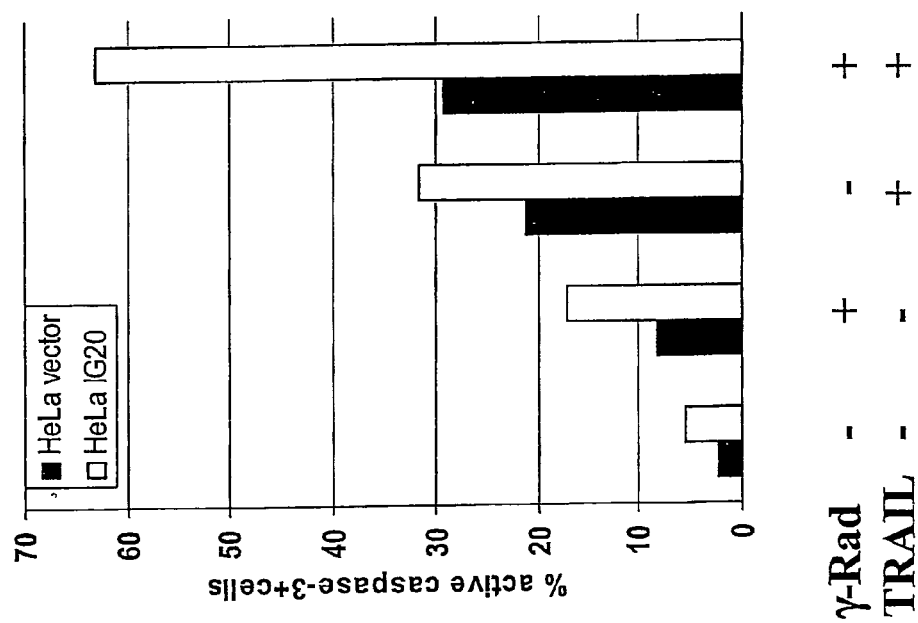
FIG. 28: Effect of γ-irradiation and TRAIL treatment on active caspase 3 levels in control and HeLa IG20 cells. HeLa vector and HeLa IG20 cells were assayed for the percentages of cells harbouring the active form of effector caspases 3 as an indicator of apoptosis. Irradiated (12 Gray) cells were plated for 24 hours and were left untreated or treated with TRAIL for 3 hours. Then cells were harvested and tested for the presence of active caspases 3.

The effects of IG20 over-expression on the susceptibility of HeLa cells to TRAIL and γ-radiation induced cell death were determined. HeLa cells either transfected with a control vector or a vector containing IG20 were exposed to γ-radiation and allowed to grow. Twenty-four hours later, these cells were treated with TRAIL for 3 hours and subjected to flow cytometry in order to determine the levels of caspase-3 as an indicator of apoptosis. These results showed that IG20 HeLa cells were more susceptible to treatment with either γ-radiation or TRAIL alone relative to controls (FIG. 28). However, this difference was more profound when the cells were exposed to a combined treatment with γ-radiation and TRAIL (FIG. 28).

Figure 20:
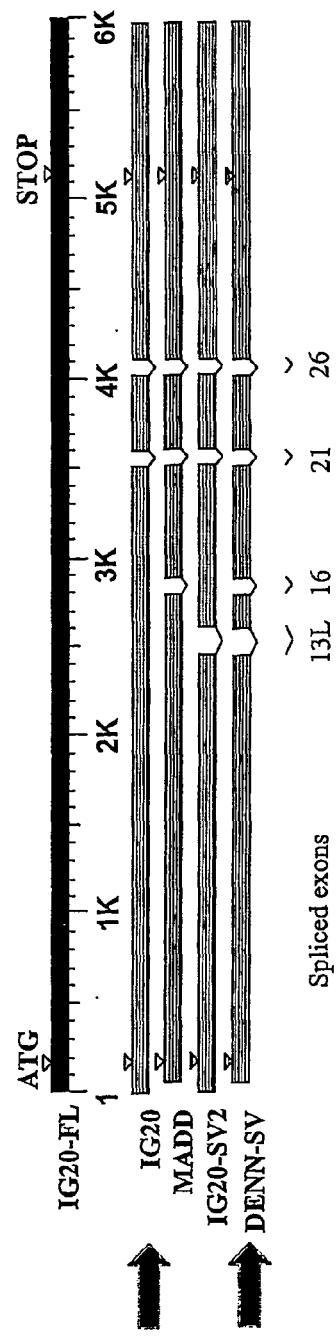
FIG. 20: Effect of IG20 and DENN-SV on outgrowth of HeLa cells following γ-irradiation. (A) Schematic representation of the splice variants of the full length IG20 gene. Only 4 splice variants (IG20, MADD. DENN-SV and IG20SV2) are readily seen in many normal and cancer tissues and only IG20 and DENN-SV (large black arrows) modulate the death inducing signals of TNFα, TRAIL and chemotherapy drugs. (3) HeLa cells stably transfected with a control vector or DENN-SV or IG20 expressing vectors were subjected to 12 Gy of γ-irradiation. Cells were allowed to grow for two weeks, fixed and visualized for outgrowth. These results are representative of 3 experiments. The assay was also repeated using 2 different stably transfected HeLa populations (C) Control and HeLa IG20 cells were subjected to 6, 8, 12 Gy of γ-irradiation or were left untreated (CTL). Cells were then plated at $10^6$ cells/p100 plate. Twenty-four hours later cells were assayed for the levels of active caspase 3. This result was representative of 2 experiments.
Figure 20:
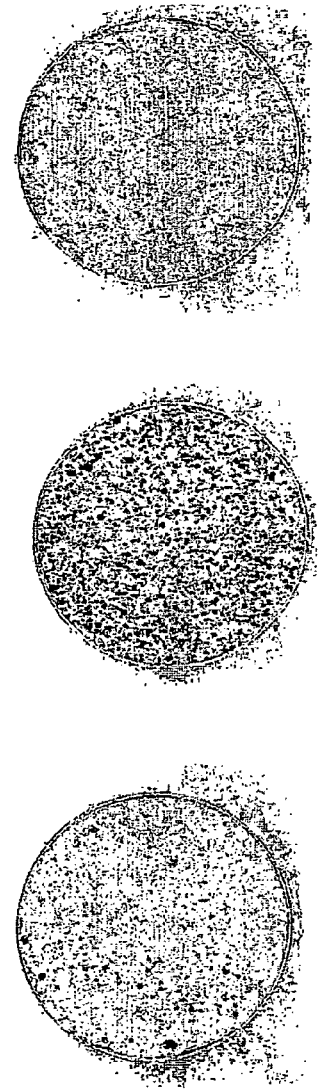
Figure 20:
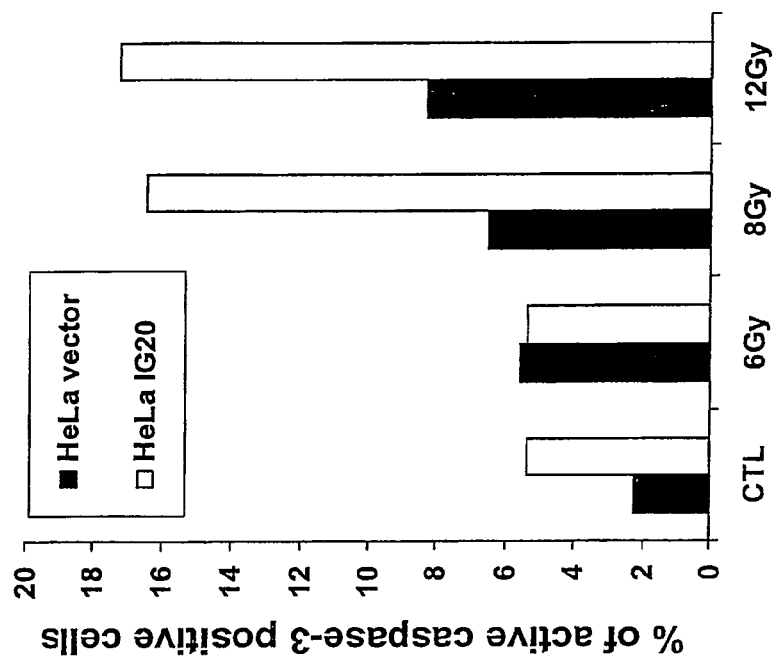

Of the four different splice variants encoded by the IG20 gene, only IG20 and DENN-SV show effects on cell proliferation and induced death (FIG. 20). DENN-SV is highly expressed in tumor tissues relative normal tissues, and its over-expression in various cell lines renders them resistant to TNFα, TRAIL, etoposide and vinblastine induced apoptosis and enhances their proliferation. In contrast, IG20 renders cells susceptible to the above treatments and suppresses cell proliferation.

Along with chemotherapy, radiation therapy remains one of the most important modalities of treatment for cancer. Therefore, to see if over-expression of the DENN-SV and IG20 in HeLa cells could affect their ability to survive and grow after γ-irradiation, 12 Grays of γ-irradiation adversely affected both HeLa control and HeLa IG20 outgrowth. However, DENN-SV transfected HeLa cells readily recovered from the treatment and showed considerable growth. There was a difference in the recovery of HeLa IG20 relative to control HeLa cells, with the HeLa IG20 cells showing the least recovery from the effects of irradiation.

Figure 21:
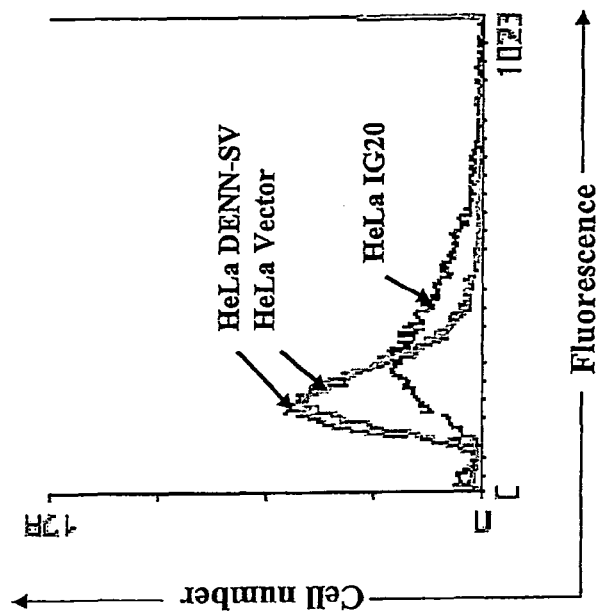
FIG. 21: Effects of IG20 splice variants on HeLa cell growth (A) Control, HeLa IG20 and HeLa DENN-SV cells ($10^5$ cells/plate) were plated in 12 well dishes (1.5 mL/well) in DMEM with 10% FCS. Cells were counted and results expressed as the mean±SD of triplicate determinations. These results are representative of at least 3 experiments. (B) Cells plated as in (A) were loaded with CFSE on day 4 and harvested on day 7. The relative CFSE dilution was determined using flow cytometry.
Figure 21:
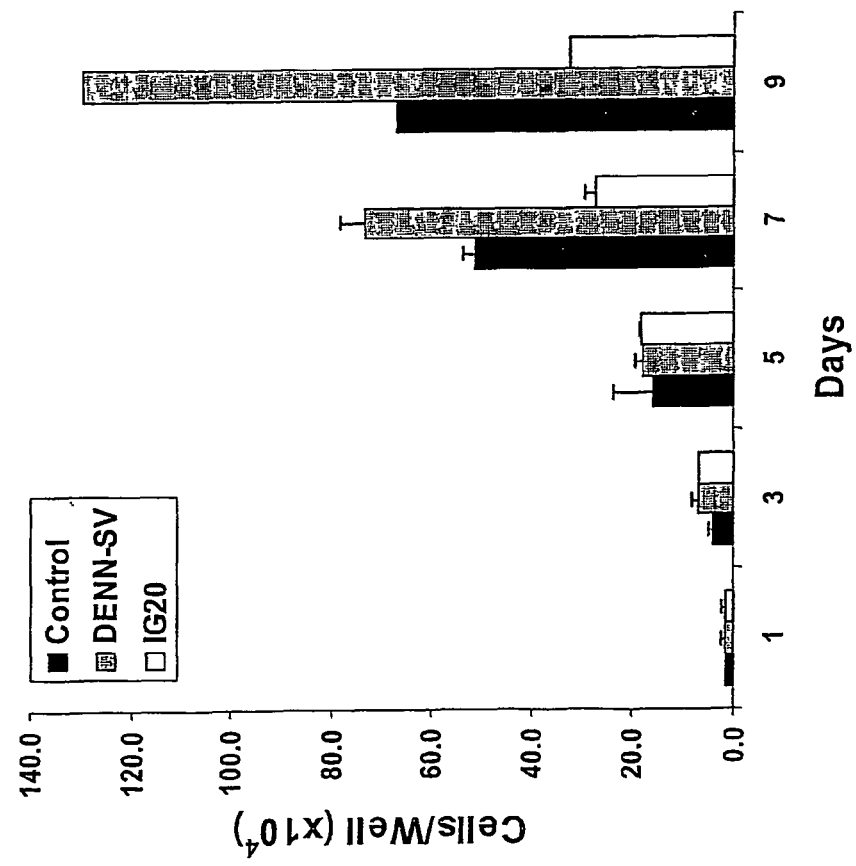
Figure 22:
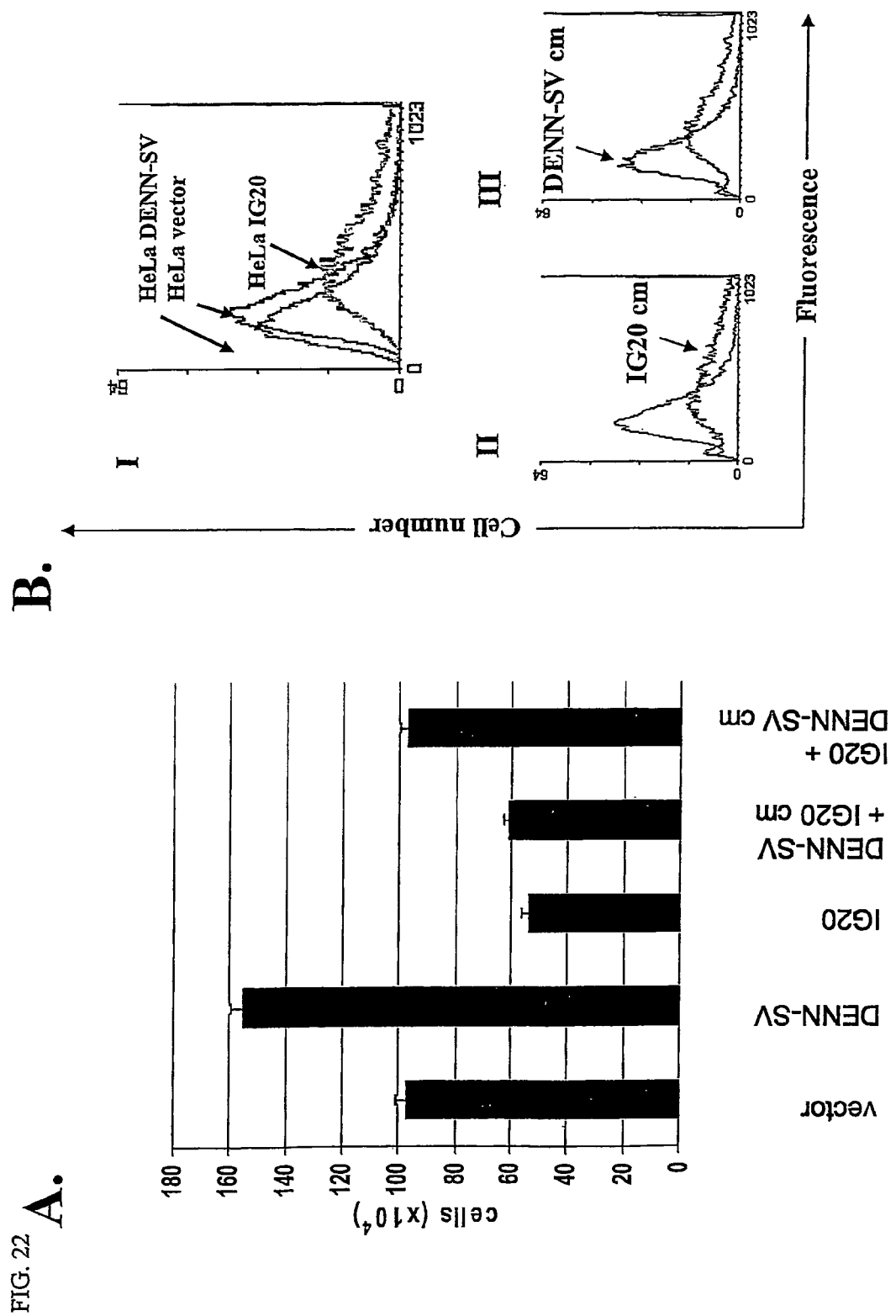
FIG. 22: Effects of conditioned media (CM) from HeLa cells stably transfected with IG20 spliced variants.(A) HeLa IG20, HeLa DENN-SV and control cells ($10^5$ cells/p100 plate) were plated and allowed to grow for 7 days. HeLa DENN-SV and HeLa IG20 cells had their media replaced daily from day 4 to day 7 with conditioned media derived from HeLa IG20 and HeLa DENN-SV cells, respectively. At day 7 all cells were harvested and counted. These results were confirmed by repeating the experiment at least 3 times. (B) Day 4 HeLa DENN-SV, HeLa IG20 and control cells were stained with CFSE and harvested on day 7 and analyzed for CFSE content (B.I). Day 4 (II) HeLa DENN-SV and HeLa IG20 (III) cells were loaded with CFSE (2 plates per cell type). One plate from HeLa DENN-SV cells was replenished with CM from HeLa IG20 cells (II) and one plate from HeLa IG20 cells was replenished with CM from HeLa DENN-SV cells (III).
Figure 23:
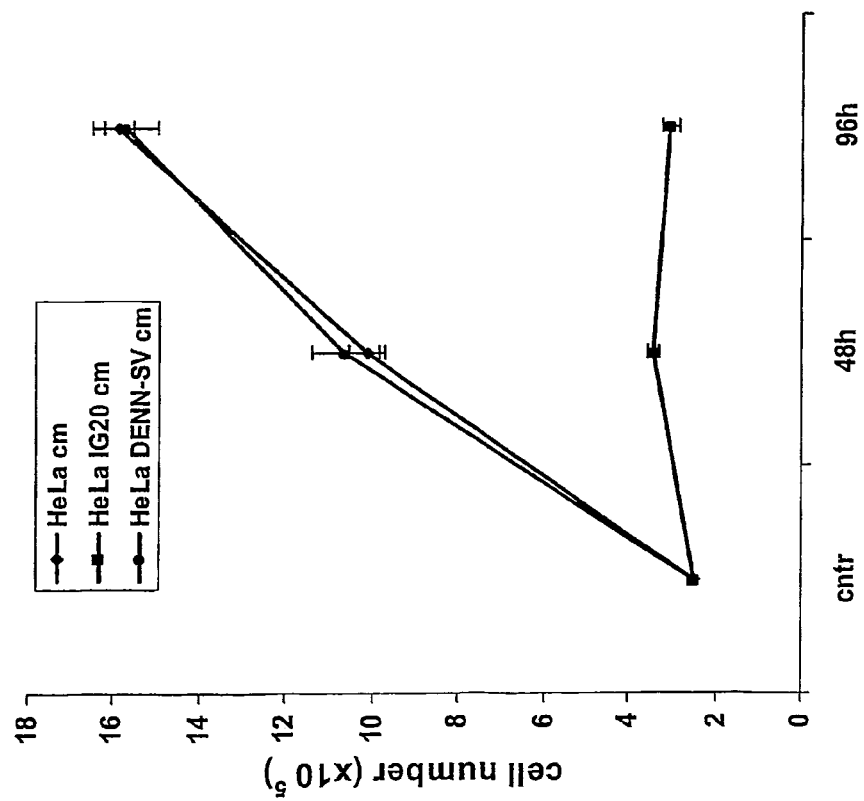
FIG. 23: The effect of CM from Hela IG20 cells on the growth of PA-1 cells. (A) $5×10^5$ PA-1 cells were plated in 12 well plates. Next day, medium was replaced with CM from HeLa IG20, HeLa DENN-SV and HeLa cells. PA-1 cells were incubated for 48 and 96 hours and cell numbers enumerated. These results are representative of at least 3 experiments. (B) $5×10^5$ PA-1 cells were plated in p100 plates and the next day cells were stained with CFSE and cultured in CM from (I) control HeLa, (II) HeLa DENN-SV and (m) HeLa IG20 cells for 24 hours. CFSE histograms (I, II, III) were overlaid with control PA-1 cells grown without media replacement (left histogram).
Figure 23:
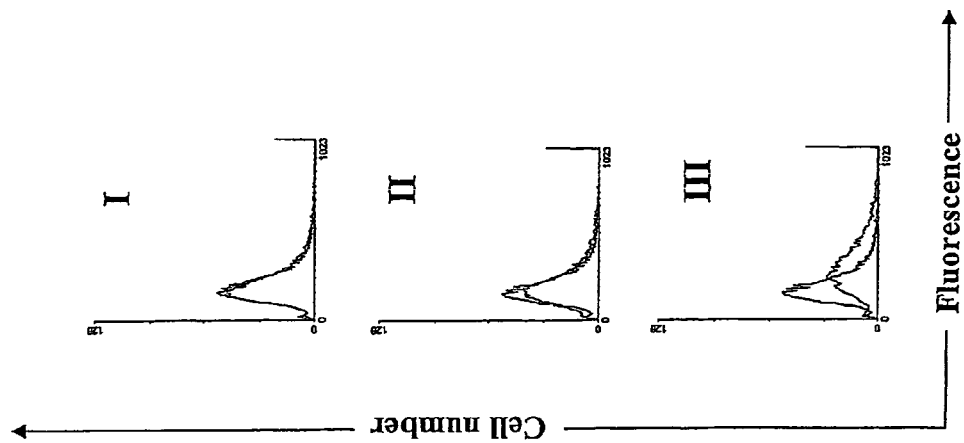

Although HeLa IG20 cells were more susceptible to Irradiation induced apoptosis, it alone was not sufficient to explain the reduction in their outgrowth following γ-irradiation. Upon closer examination of the growth characteristics, it appeared that the HeLa DENN-SV and HeLa IG20 cells grew faster and slower respectively than HeLa control cells (FIG. 21). The HeLa IG20 cell growth curve demonstrated a biphasic pattern where the growth was very similar to that of HeLa controls and HeLa IG20 cells up to day 5, and then abruptly changed with HeLa IG20 cells growing considerably slower. This suggested that a minimum concentration of a critical factor or signal might be required for the growth suppressive effect. Trans well experiments and reciprocal exchange of CM from IG20 and DENN-SV transfected cells showed that a critical factor(s) was present in the culture supernatant of HeLa IG20 cells, and that it could affect the growth of control and HeLa DENN-SV cells. Moreover, it also suggested that the growth inhibitory property of the CM from HeLa IG20 cells could dominate the growth potentiating properties of DENN-SV (FIG. 22C).

Figure 25:
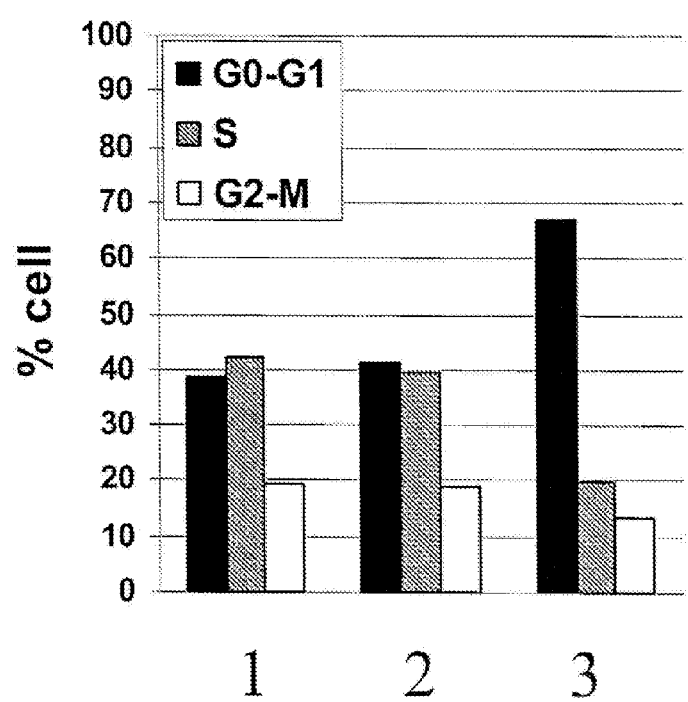
FIG. 25: The effect of CM from HeLa IG20 cells on the cell cycle progression of PA-1 cells. PA-1 cells were plated in 3 p100 plates ($5×10^5$ cells/plate). Control cells were harvested 24 hours later and analyzed for cell cycle progression (1). At this point media from remaining plates were replaced with CM from either HeLa control (2) or HeLa IG20 (3) 48 hours later cells were subjected to cell cycle analysis.
Figure 26:
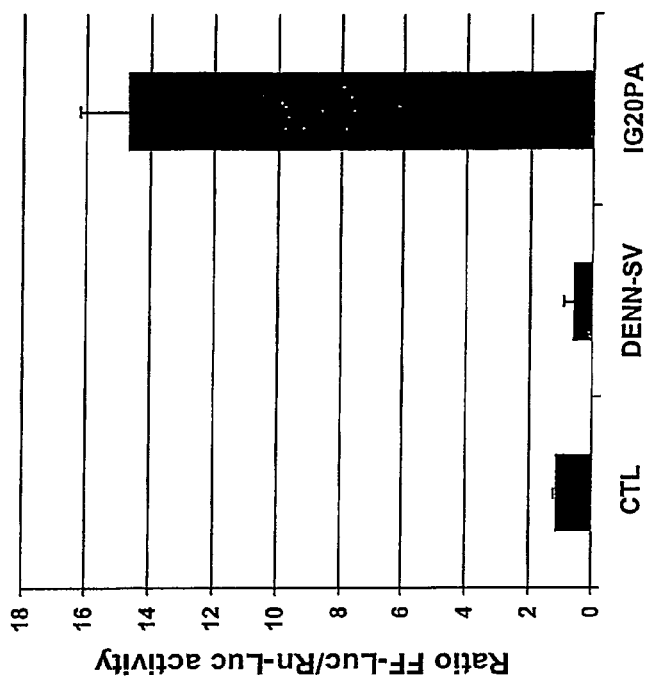
FIG. 26: IL-6 secretion and NF-κB basal activity is upregulated in HeLa IG20 and not HeLa DENN-SV cells (A) $10^5$ HeLa vector, HeLa DENN-SV and HeLa IG20 cells were plated in p100 plates inserum-free media 4 days later, supernatants were assayed for the presence of IL-6. These are representative results from 3 experiments. (B) HeLa vector, HeLa DENN-SV and HeLa IG20 cells were co-transfected with a reporter NF-κB luciferase plasmid and a renilla luciferase plasmid driven by a CMV promoter. Forty-eight hours later, cells were harvested, lysed and assayed for firefly luciferase activity that was then normalized to the renilla luciferase activity. These results are representative of 3 experiments.
Figure 26:
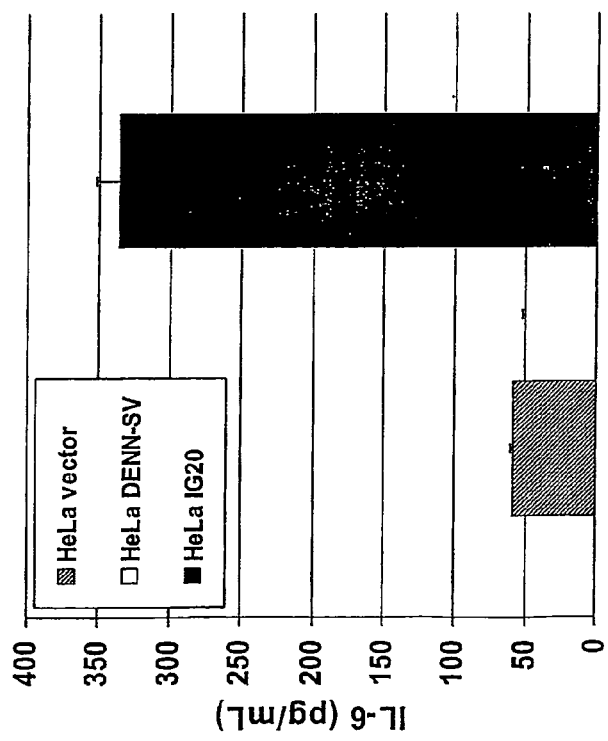

The CM from HeLa IG20 cells had a profound effect on the ovarian cancer cell PA-1, and completely stopped its growth as determined by cell proliferation (FIG. 23A), dilution of CFSE (FIG. 24B), staining for mitotic bodies (FIG. 25) and cell cycle analysis (FIG. 25). This clearly demonstrated that the soluble factor present in HeLaIG20 culture supernatant could not only suppress HeLa cell growth but also the growth of PA-1 ovarian cancer cells. Moreover, accumulation of PA-1 cells in the G0-G1 phase of the cell cycle suggests that the CM either induced PA-1 cells to undergo senescence (G0) or cell cycle arrest at the G1 checkpoint.

When supernatants from HeLa IG20 cells and control cells were compared for the amounts of several cytokines, some increase in the amounts of most of the cytokines tested were observed, however, there was a profound increase in the amount of IL-6. This was further confirmed by ELISA results that showed elevated levels of IL-6 in the CM from HeLa IG20 cells but not from the others. The importance of IL-6 in suppressing the growth of PA-1 cells was further established when a considerable reversal of the effect was noted in the presence of a neutralizing IL-6 antibody (FIG. 27). The antibody did not completely reverse the growth suppressive effects of the Hela IG20 CM and suggested that IL-6 might be one of the factors that can cause growth suppression.

Indeed, it is not uncommon to see the production of IL-6 by tumor tissues and cancer cell lines, including cervical and ovarian cancers. However, the effect of IL-6 on cancer tissues and cell lines is highly dependent on the tissue type and the cells involved, and sometimes the effects may vary even within the same tissue. For example, IL-6 may enhance or deter cell growth depending upon the ovarian cancer cell line being tested. As disclosed herein, IL-6 inhibited the growth of PA-1 ovarian cancer cells in a manner consistent with blocking cell cycle progression at the G1-G0 stage. Earlier studies have shown that upon IL-6 treatment, early stage melanoma cell lines, human prostate cell line LNCAP and leukemic myeloblastic cells are also growth arrested at the G1-G0 stage of the cell cycle. The mechanism by which IL-6 induces growth arrest and/or differentiation is unclear but may involve the induction of CDK inhibitors.

IL-6 production can also play a pivotal role in cancer progression. In an earlier study it was observed that IL-6 produced by skin fibroblasts could inhibit the growth of early melanomas but not advanced stage melanomas. This was not due to differences in the levels of expression of either the IL-6 receptor or the IL-6 transducer (gp130). Interestingly, the melanoma cells themselves secreted IL-6. Further studies then showed that IL-6 undergoes transition from being a paracrine growth inhibitor to an autocrine stimulator during human melanoma progression.

IG20 can enhance radiation-induced apoptosis (FIG. 20C). This coupled with a previous observations that IG20 can enhance TRAIL and TNFα induced apoptosis suggest a convergence of the extrinsic (i.e. TNFα and TRAIL) and the intrinsic apoptotic pathways (i.e. γ-irradiation). Induction of the extrinsic pathway through TNFα and TRAIL binding to their cognate receptors activates caspase 8 and subsequently the effector caspase 3. When the cells are stressed, the intrinsic pathway is initiated through the mitochondria resulting in the activation of caspase 9 and then caspase 3. Results show that although over-expression of IG20 results in constitutive upregulation of NF-κB, upon intrinsic or extrinsic death stimulus the ability of IG20 to enhance caspase activity predominates.

The combined effects of TRAIL and etoposide or CDDP (chemotherapeutic DNA damaging agent) could cooperatively induce apoptosis of glioma cells in vitro and reduce tumor loads in nude mice in vivo.

Significant implications for cancer therapy are associated with the invention because DENN-SV is highly expressed in tumors with little or no expression of IG20. Further, overexpression of IG20 can render PA-1 cells more susceptible to TRAIL induced apoptosis5. HeLa cells normally express both the antiapoptotic (DENN-SV) and the pro-apoptotic (IG20) variants. The efficacy of α-irradiation induced cell death is enhanced by IG20 over-expression. Exposure to both TRAIL and α-irradiation can work cooperatively and enhance apoptosis even more significantly (FIG. 28).

Figure 29:
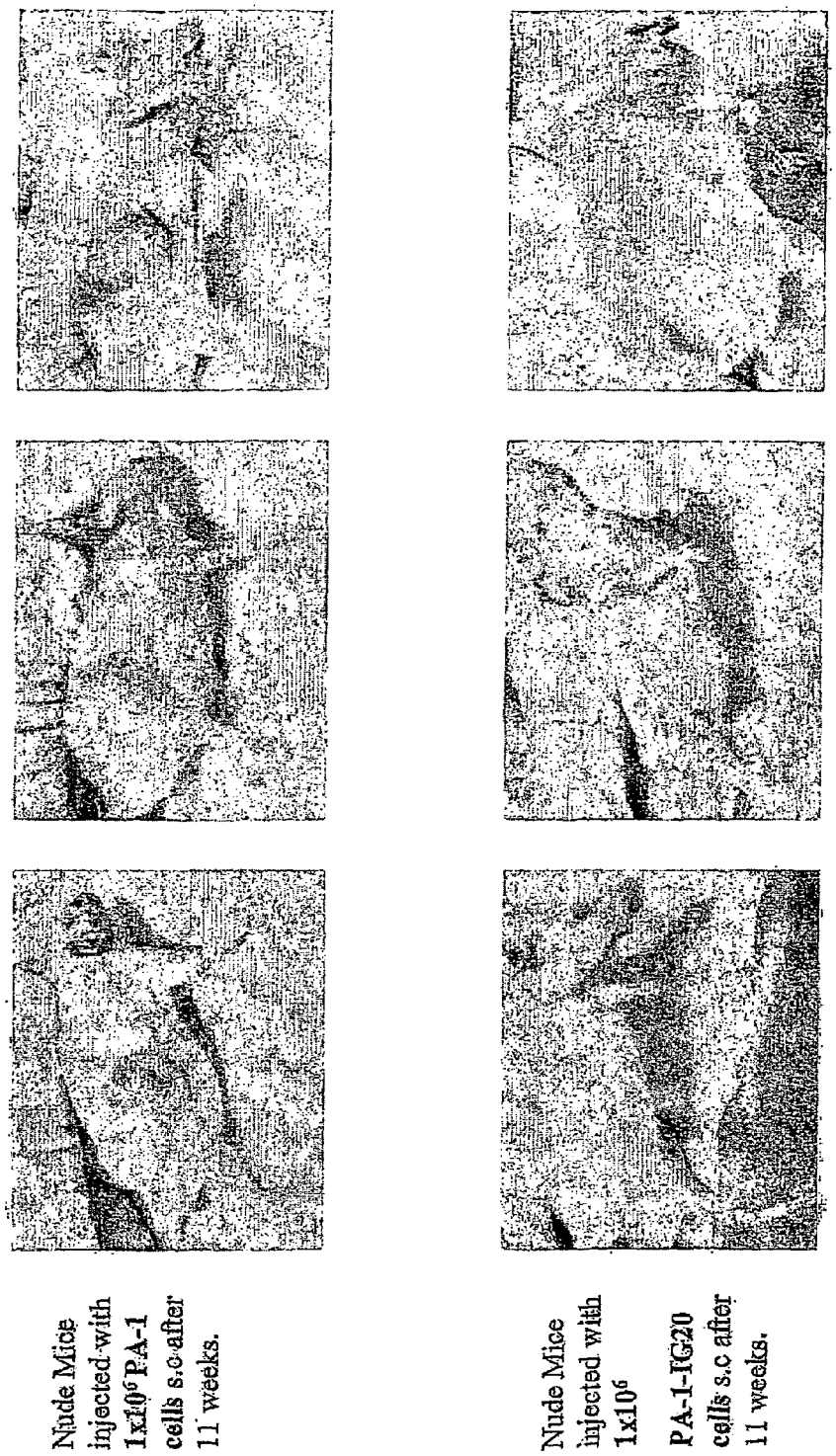
FIG. 29: Shows results of the mouse experiment.

Nude mice injected with $1 \times 10^6$ PA-1 cells sub-cutaneously, develop tumor growth as shown in FIG. 29 (top panels), whereas nude mice injected with $1 \times 10^6$ PA-1-IG20 cells do not develop tumor growth after 11 weeks (FIG. 29, bottom panels).

IG20 can render cells more susceptible to apoptosis and suppress cell growth. This raises the possibility of using IG20 to render cells that are otherwise resistant to become more susceptible to various modalities of cancer therapy.

Materials and Methods

RT-PCR Using RNA from Human Tissues

Human tissue samples were provided by the Cooperative Human Tissue Network (CHTN), which is funded by the National Cancer Institute. Highly pure intact full-length poly-A+mRNAs were directly isolated from various tissues using μMACS mRNA Isolation Kit (Miltenyi Biotec Inc., Auburn, Calif.) according to the manufacturer's protocol. Briefly, tissues were minced, lysed, mixed with the MicroBeads conjugated to Oligo (dT) and then loaded onto the μMACS magnetic columns. The columns were washed and the bound mRNAs eluted with hot (65° C.) RNase-free water. Fifty ng mRNA from each sample was used in SuperScript-One-used; otherwise, protocols were identical. A first incubation at 50° C. for 30 minutes was followed by incubation at 94° C. for 2 minutes. Subsequent 30 cycles of PCR were carried out at 94° C. for 30 seconds, 55° C. for 30 seconds, and 72° C. for variable time periods (as described herein), followed by a final incubation at 72° C. for 7 minutes. For amplifying exons 13L and 16, F-1 and B-1 primer pair (5' CGG GAC TCT GAC TCC GAA CCT AC 3' (SEQ ID NO: 2) and 5' GCG GTT CAG CTT GCT CAG GAC 3' (SEQ ID NO: 3), respectively) was used, with 1 minute extension time. For amplifying exon 21, F3453 and B3648 primer pair (5' AAG TGC CAC AGG AAA GGG TC 3' (SEQ ID NO: 4) and 5' TGC GCT GAT CTG GGA CTT TT 3' (SEQ ID NO: 5), respectively) was used, with 30 seconds extension time. For amplifying exon 26, F3944 and B4123 primer pair (5' AGC CAT GCA TAA AGG AGA AG 3' (SEQ ID NO: 6) and 5' GGT CCC ATA AAG TAG AAC GC 3' (SEQ ID NO: 7), respectively) was used, with 30 seconds extension time. For amplifying exon 34, F4824 and B5092 primer pair (5' CTG CAG GTG ACC CTG GAA GGG ATC 3' (SEQ ID NO: 8) and 5' TGT ACC CGG GTC AGC TAG AGACAG GCC 3' (SEQ ID NO: 9), respectively) was used, with 30 seconds extension time. All primers were used at 10 μM each. The resultant cDNAs were separated on 5% polyacrylamide gels (PAGE) and compared to molecular size markers to determine the product size.

Sequencing of RT-PCR Products

To sequence the PCR products, 10 μl of cDNA from representative RT-PCR products were run on PAGE until the desired fragments were clearly separated. Then, bands corresponding to the expected size of a given variant were excised, purified and cloned into pGEM-Teasy vector (Promega, Madison, Wis.), and used to transform E. coli DH5α. Clones containing the desired fragments were identified by restriction analysis and sequenced using the corresponding primers described herein.

Cloning of IG20 Splice Variants into Mammalian Expression Vectors

IG20, MADD and DENN-SV were each separately cloned into the multiple cloning sites (MCS) of pBKRSV (Stratagene, La Jolla, Calif.), and pCDNA 3.1 His vector (Invitrogen, Carlsbad, Calif.) as described by Al-Zoubi et al., (2001). The remaining four IG20 splice variants (i.e., IG20-FL, KIAA0358, IG20-SV2, and IG20-SV4) were first cloned into pBKRSV and then into pCDNA 3.1 His vector. IG20 cloned into 21pBKRSV as a backbone was used, as described herein. KIAA0358 (clone number hh00017 inserted at the SalI-NotI site of the pBluescript IISK+(PBSSK) vector) was kindly provided by Kazusa DNA Research Institute (Chiba, Japan). Similarly, IG20-SV4 was cloned into pBSSKII at the SalI-NotI site. Both KIAA0358 and IG20-SV4 were excised out of pBSSKII and cloned into pBKRSV at the SalI and NotI sites. To clone IG20-FL into pBKRSV, both pBSSK-KIAA0358 and pBKRSV-IG20 were digested with AatII and KpnI that flank the region containing exons 21 and 26 (FIG. 2). The AatII-KpnI fragment of KIAA0358 that contains unspliced exons 21 and 26 was used to replace the corresponding fragment in pBKRSV-IG20 that lacks these exons. To clone IG20-SV2 into pBKRSV, both DENN-SV and pBKRSV-IG20 were digested with AatII, which cuts at two sites on IG20 (and DENN-SV) that flank exons 13L and 16. Digestion of pBKRSVIG20 with AatII produced two fragments of about 1 and 8.3 kb, and digestion of DENNSV produced two fragments of about 1 and 5 kb. The 1 kb fragments from both were further digested with Esp31 that cuts between exons 13L and 16. The AatII-Esp31 fragment from DE-NN-SV that spans exon 13L (where exon 13L is spliced into 13S) was used to replace the corresponding fragment in pBKRSV-IG20 (where exon 13L is unspliced). Restriction analyses and sequencing confirmed the appropriate cloning of each of the above cDNAs into pBKRSV. To construct tagged cDNAs, we used pCDNA 3.1 His-IG20 as a backbone. IG20-FL, IG20-SV2, IG20-SV4, and KIAA0358 were cloned into pCDNA 3.1 His-IG20 at ClaI site at 279 nucleotides downstream of IG20 ATG start codon and NotI site at the c-terminal of IG20. The correct clones were identified by restriction analyses using NotI and ClaI, and then with AatII, and by sequencing.

Transfection of Mammalian Cells with cDNAs Encoding Different IG20 Splice Variants Control pCDNA 3.1 His vector, or vector containing various cDNAs, were used for transfecting HeLa, 293T and PA-1 cell lines. Cells were transfected using Super-FectTransfection Reagent (Qiagen) according to previously published protocols (Al-Zoubi et al., 2001). To select for permanently transfected cells, growth medium was replaced at 24 hours post-transfection, and then once every three days for 21 days, with fresh medium containing 400 μg/ml G418. Expression of transfected cDNAs was then confirmed by immunoblotting as described herein.

Immunoprecipitation of IG20 Splice Variants

Permanently transfected human embryonic kidney (293T) cells were plated in 150 cm² dishes at $8 \times 10^6$ cells/dish and grown overnight. Next day, cells were harvested by trypsinization and then counted; equal numbers of cells from all samples were used. Further processing of cells and cell lysates was carried out at 4° C. Cells were washed once in ice-cold PBS and were incubated in lysis buffer T (20 mM Tris-Cl, pH 7.5, 1% TritonX-100, 137 mM NaCl, 25 mM ®-glycerophosphate, 2 mM EDTA, 1 mM Na$^5$VO$_4$, 2 mM sodium pyrophosphate, 10% (v/v) glycerol, 10 µg/ml leupeptin, and 2 Mm phenylmethylsulfonyl fluoride) for 1 hour. Lysates were subjected to centrifugation at 13000 rpm for 30 minutes, supernatants were transferred to other tubes and total proteinconcentration was determined. Equal amounts of total protein from each sample were used in subsequent immunoprecipitations. Samples were pre-cleared by incubation with 5 µl/sample of normal rabbit sera for 30 minutes followed by addition of 25 µl protein A/G PLUS-Agarose (Santa Cruz Biotechnology, Santa Cruz, Calif.) and further incubation for 30 minutes. Samples were then centrifuged at 13000 rpm for 1 minute, and the supernatants were transferred into new tubes and incubated at 4° C. overnight with 5 µl of a mixture of anti-IG20 N, C and M antibodies. These antibodies were generated against three different peptides derived from the N-terminus (N) C-terminus (C) and the middle part (M) of the protein as described by Al-Zoubi et al. (2001). To detect specific IG20 variants, the above immunoprecipitated samples were separated and then transferred onto nitrocellulose membrane and detected using anti-His monoclonal antibodies (Clonetech).

TNFα Treatment of Cells

Cells were plated in 6-well plates at 1.2×10$^5$ in growth medium. Twenty four hours later, cells were either untreated or treated with 10 ng/ml TNF-α and 10 µg/ml cyclohexamide (CHX) for 6 hours. To assess the effects of TNFα and CHX treatment, cells were either stained with 100 nM tetramethylrhodamine ethyl ester (TMRE) (Molecular Probes, Eugene, Oreg.) for 10 minutes, harvested by trypsinization, washed once with ice-cold PBS and then subjected to FACS analysis, or were stained with either trypan blue and evaluated for viability using a light microscope, or with 1 µg/ml Hoechst 33342 (Sigma) for 10 minutes and evaluated for chromatin condensation in situ using a Diaphot 200 inverted microscope with an epifluorescence attachment (Nikon, Melville, N.Y.).

Drug Treatment of Cells

Cells were plated (10$^5$ cells/well) the day before treatment into 6 well plates. Cells were treated with etoposide for 24 hours or vinblastine for 1 hour at indicated concentrations. After treatment, cells were washed 3 times with PBS and then replenished with fresh media and incubated at 37° C. Two weeks later, cells were fixed in ice-cold methanol and stained with crystal violet for visualization.

TRAIL Treatment of Cells

PA-1 cells were plated in 6 well dishes (5×10$^5$ cells/well). Next day, cells were treated in situ with 50 ng/ml TRAIL (Peprotech, Rocky Hill, N.J.) for 3 hours with or without 50 µMz-VAD (30 minute pre-incubation). Cells were then assayed for levels of active caspase 3.

Active Caspase 3 Assay

Cells were harvested, washed once with PBS and then fixed in Cytofix/Cytoperm solution and washed with Perm/Wash buffer as suggested by the manufacturer (Pharmingen, SanDiego, Calif.). Cells were then stained with PE-conjugated rabbit anti-active caspase 3 antibody according to the manufacturer's protocol (Pharmingen). Cells were then subjected to FACS analysis to determine percentage of cells with active caspase 3.

Proliferation and Colony Formation in Soft Agar

To measure cell proliferation, cells were plated in triplicates at 1×10$^5$ Cells/100 mm$^2$ plate, and then were harvested and counted on days 1, 3 and 5 after plating. To assess the ability of cells to form colonies in soft agar, 1.4% Agarose in water was mixed with 2×DMEM (20% FCS, 2× pen/strep) to create the bottom layer; 1 ml of this was used to line the bottom of each well (6 well dishes). Variable numbers of cells diluted in 1 ml of DMEM (supplemented with 10% FCS, pen/strep) were mixed with 1 ml of 0.7% agarose in DMEM (liquid form) and used to form the top layer (final 0.35% Agarose in DMEM 10% FCS, penicillin/streptomycin). Colony formation was observed under a microscope.

CFDA Staining of Cells

1×10$^5$ Cells/100 mm$^2$ plate were stained with 2 µM CFDA (Molecular Probes, Eugene, Oreg.) in situ in 5 ml PBS/100 mm$^2$ for 10 minutes at 37° C. Cells were then washed 3 times and replenished with new media Cells were harvested 5 days later and analyzed by FACS.

Hoechst Staining

Cells were stained in situ with 1 µg/ml of Hoechst 33342 (Sigma, St. Louis, Mo.) in DMEM for 10 minutes at 37° C. Chromatin condensation was then visualized in situ using a Diaphot 200 inverted microscope with an epifluorescence attachment (Nikon, Inc., Melville, N.Y.). 10 different fields were randomly chosen to determine the average number of cells with condensed chromatin (apoptotic) as compared to live cells.

Luciferase Assay for NFκB Activation

Measurement of NFκB activation was performed using the Dual-Luciferase Assay System (Promega, Madison, Wis.) according to manufacturer's protocol. Briefly, cells were plated in 12 well dishes (5×10$^5$ PA-1 cells/plate) and 18-24 hours later were co-transfected with 0.01 µg/well of NFκB firefly luciferase reporter construct and 0.001 µg/well of Renillaluciferase control vector pRL-SV40. Cells were allowed to recover for 24 hours and then replenished with serum free medium. Next day, cells were left untreated or treated for 5 hours with TNFα or TRAIL. Subsequently, they were washed and lysed in situ for 30 minutes with gentle agitation using the manufacturer's lysis buffer. 20 µL of each lysate was then used to test for levels of firefly luciferase activity and normalized with the levels of Renilla luciferase activity.

Transfection of Cells with DN-IκBα and CrmA

Cells were plated in 6-well plates at 1.5×10$^5$/well in growth media Twenty-four hours later, cells were transfected with either a cDNA encoding farnesylated GFP (GFP-f) alone, or co-transfected with either an empty vector, or a vector containing cDNA encoding either CrmA or DN-IκBα, at a 1:5 ratio. At 24 hours post-transfection, cells were either untreated or treated with TNFα and cyclohexamide for 6 hours, as described herein. Then, cells were stained with TMRE and subjected to FACS analysis; only GFP-f-gated cells were included in the analysis.

RT-PCR of TNFα-Resistant HeLa Cells

To separate cells that were undergoing apoptosis, or resistant to apoptosis upon TNFα treatment, the Annexin V microbeads (Miltenyi Biotec, Inc.) were used according to manufacturer's protocol. Annexin V is a phospholipid-binding protein that recognizes phosphatidylserine on the surface of apoptotic cells. Briefly, cells were plated and treated with TNFα and CHX for 6 hours as described herein, washed once with PBS to remove dead cells and debri, collected, passed through 30 µM filter, and incubated with Annexin Vmicrobeads for 15 minutes at 6-12° C., and then washed once and resuspended in 500 µl buffer. Cells were then passed through a magnetic column. Flow through included non-apoptotic, TNFα-resistant cells, whereas cells bound to the column represented apoptotic cells. Columns were washed three times with buffer, removed from magnet and cells bound to the matrix were eluted. Untreated control, TNFα-resistant, and apoptotic cells were then used for isolation of Poly-A+ mRNA using the µMACS mRNA Isolation Kit (Miltenyi Biotec), or were used for TMRE staining to determine percentage of apoptotic cells, as described herein.

Construction of plasmids—A cDNA encoding IG20 pro-apoptotic splice variant (GenBank Accession Code-AF440101, termed IG20 was cloned in-frame into pcDNA3.1/NT/GFP/TOPO vector (invitrogen, Carlsbad, Calif.) using the TA cloning site from the pBKRSV clone described by Al-Zoubi et al., (2001). The His-tagged IG20 construct has been described herein. IG20 was also subcloned into Bgl II and Apa I sites of the EYFP-C1 vector (Clontech, Palo Alto, Calif.). The IG20 construct was made by specific PCR amplification of a 748-residue fragment (amino acid 628 to 1376) from the full length IG20. This PCR amplified product was directly ligated into the TA cloning site of pcDNA3.1/NT/GFP/TOPO vector. The DR4-Flag construct, a gift from Vishva M. Dixit (Genentech, South San Francisco, Calif.), was used to sub clone DR4 into the Bgl II and EcoR I sites of ECFP-N1 vector (Clontech). The DR5-Myc was a gift from W. S. El-Deiry (University of Pennsylvania, Philadelphia, Pa.) and was used to clone the DR5 construct into the Bgl II and Eco RI sites of ECFP-N1 vector.

Cell lines—IG20 tagged with GFP and the pcDNA3.1/NT/GFP/TOPO empty vector (10 µg each) were transfected into HeLa cells using the superfect reagent from Qiagen Inc. Valencia, Calif. Three hours post-transfection, cells were washed with 1×PBS and replenished with Dulbecco's Modified Eagle's medium (Gibco Invitrogen Co., Carlsbad, Calif.) with 10% Fetal Bovine serum, 2 mM L-glutamine and antibiotics (penicillin G-100 units/mL and streptomycin-100 µg/mL). All cell lines were cultured at 37° C. in a humidified atmosphere containing 5% $CO_2$. Stably transfected cells of HeLa IG20 and Vector Control were established by culturing cells in growth medium containing G418 (400 µg/mL) for 3 weeks, with weekly change of the medium and expression was confirmed by immunoprecipitation of IG20-GFP protein.

Antibodies and other reagents—The anti-IG20 peptide polyclonal antibody, raised against 3 different peptides from the N-terminal, middle and C-terminal region of IG20, has been described by Al-Zoubi et al., (2001). Anti Caspase-8 antibody (C-15) was a gift from Marcus E. Peter (Ben May Institute of Cancer Research, University of Chicago, Chicago). Anti caspase-8 monoclonal antibody 6B6 was purchased from Cell Signaling Technology Inc, Beverly, Mass. PE-conjugated rabbit anti active Caspase-3 antibody and anti-FADD antibodies were obtained from BD PharMingen, San Diego, Calif., anti-His antibody was purchased from Clontech Palo Alto, Calif., anti-Flag M2 monoclonal from Sigma-Aldrich Corp., St. Louis, Mo., USA; anti-DR5 (IMG 120, rabbit polyclonal), anti-DR4 (H-130, rabbit polyclonal) and B-9 (mouse monoclonal) antibodies were obtained from Santa Cruz Biotechnology, Inc., Santa Cruz, Calif. TNF-α and Cycloheximide were obtained from Sigma-Aldrich Corp and recombinant human TRAIL was purchased from Peprotech Inc., Rocky Hill, N.J.

Mitochondrial depolarization and chromatin condensation—$2\times10^5$ HeLa IG20 and Vector control cells were plated into a 12-well culture dish and allowed to grow for 48 hours. Duplicate wells were left untreated or treated with 10 ng/mL of TNF-α and 10 µg/mL of cycloheximide. Equal numbers of cells were left untreated or treated with recombinant TRAIL at 100 ng/mL and both treatments lasted for 5-hours. Cells were assessed for loss of mitochondrial membrane potential by staining with tetramethylrhodamine ethyl ester (100 nm, Molecular Probes, Eugene, Oreg.) for 10 minutes, washed once with ice-cold PBS, collected and subjected to FACS analysis. Cells from parallel samples were stained with 1 µg/mL Hoechst 33342 (Sigma-Aldrich Corp) for 10 minutes and viewed under a Diaphot 200 inverted microscope with an epifluorescence attachment to analyze chromatin condensation.

Caspase activation—To assess the general activation of caspases, cells were stained with FITC tagged caspase inhibitor Val-Ala-Asp-flouromethyl ketone Promega, Madison, Wis.) for 10 minutes at 37° C., washed and analyzed by FACS for percentage of FITC positive cells. The initiator caspases were analyzed by using carboxyflourescein labeled peptide flouromethylketone inhibitors (FAM-peptide-FMK) directed against active caspase-8, 9 and 10 (APOLOGIX caspase detection kit, Cell Tech Inc., Minneapolis, Minn.). For testing levels of activecaspase-3, cells were fixed and permeabilized using cytofix/cytoperm solution (BDPharmingen, San Diego, Calif.) for 30 minutes at 4° C. Cells were washed with Perm/wash buffer (BD Pharmingen) and stained for 1 hour in the dark at room temperature with 10 µl per sample of active-anti-caspase-3 PE conjugated antibody. Cells were collected, washed once, resuspended in Perm/wash buffer and analyzed by FACS for PE positive population. For detecting the caspase-8 cleaved fragment, $1\times10^7$ of vector and IG20 transfected HeLa cells were treated with 100 ng/mL of TRAIL for 1 or 3 hours, lysed with RIPA lysis buffer and normalized for protein concentration. The proteins were separated by SDS-PAGE, transferred and probed for the p10 cleaved caspase-8 fragment using the 6B6 antibody.

Cell surface expression levels of TRAIL receptor—A total of $5\times10^5$ HeLa control and IG20 cells were collected in enzyme free solution, washed once with PBS containing 0.5% BSA and let stand in the same buffer for 10 minutes at 4° C. PE-conjugated anti-DR4 (DJR1 clone), anti-DR5 (DJR2-4 clone), anti-DcR1 (DJR3 clone) and anti-DcR2 (DJR4-1 clone) antibodies purchased from eBiosciences, San Diego, Calif. were used. Each sample was incubated with 20 µL of specific as well as control mouse IgG antibody per sample for 30 minutes at 4° C. The cells were then washed with 1×PBS and analyzed by FACS using a FACScan (Becton Dickinson, San Jose, Calif.).

Brefeldin A treatment—Equal number of control and IG20 HeLa cells were treated with brefeldin A (1 µg/mL, Sigma-Aldrich Corp.) for the indicated time periods and analyzed by FACS after staining with anti-DR5 antibody (DJR2-4 clone).

Transfection with dominant negative FADD, CrmA and p35 constructs—Control vector and IG20 stably transfected HeLa cells were plated at $5\times10^5$ overnight and the dominant negative FADD, Crm A and p35 constructs were co-transfected (2 µg each) with farnesylated EGFP at a ratio of 1:5. Equal numbers of wells were co-transfected with an appropriate control vector along with EGFP-F at the same ratio. The transfected cells were left untreated or treated with the TRAIL, or with TNF-α and cycloheximide, for 5 hours and cells were collected and stained for active caspase-3 (anti caspase-3 antibody) and subjected to FACS analysis to detect active caspase-3 staining in GFP-positive cells.

Co-localization studies—$2\times10^4$ HeLa cells plated on chamber slides were co-transfected with the DR4-CFP and IG20-YFP constructs in a ratio of 1:5 (total 5 µg of DNA). At 12 hours, the cells were treated with 10 µM of Z-VAD. After 24 hours of transfection, the cells were fixed in 4% formaldehyde fixative solution, washed with PBS and mounted with cover slips using the vectashield-mounting medium (Vector Labs, Burlingame, Calif.). Slides were then imaged on an Olympus 1×70 epiflourescensce microscope using the slide book program (Intelligent-ImagingInnovations, Denver, Colo.) under a 100× oil-immersion objective. The individual channels used were captured in a Z-series on a CCD digital camera Co-immunoprecipitation—Either IG20-His or. IG20-GFP were co-transfected with DR4-Flag in a ratio of 2:1 (a total of 15 µg of DNA) into 0.5×10$^6$ 293 T cells using calcium phosphate transfection method. Co-transfections of IG20-His, IG20-GFP were also done with DR5-Myc constructs. Cells were collected and lysed 24 hours after transfection in lysis buffer [20 mM Tris/HCl, pH 7.5, 137 mM NaCl, 2 mM β-glycerophosphate, 2 mM EDTA, 1 mMNa$_3$ VO$_4$, 2 mM sodium pyrophosphate, 2 mM phenylmethylsulfonyl fluoride (PMSF), protease inhibitors cocktail (Roche), 1% Triton X-100 and 10% glycerol] for half hour on ice and then clarified by centrifugation at 12,000 rpm for 30 minutes at 4° C. Cell lysates were immunoprecipitated overnight with either 10 µL/mL of anti-IG20 peptide antibodies, 5 µg/mL of anti-Flag M2 antibodies, 5 µg/mL of Myc antibody (Zymed, South San Francisco, Calif.) or 5 µg/mL of DR5 (IMG 120). Protein A/G beads were added and samples were conjugated for 2 hours after which beads were washed three times with lysis buffer and boiled in SDS lysis buffer. The eluates were then subjected to SDS-PAGE for subsequent immunoblot analysis.

Immunoprecipitation and DISC analysis—Control and IG20 HeLa cells (2×10$^7$) were collected and left untreated or treated with TRAIL at a concentration of 1 µg/ml in a 37° C. water bath for 10 minutes or 30 minutes. At the end of the treatment, the cells were immediately washed with ice-cold 1×PBS and pelleted. The washed cells were then lysed with 1 mL of lysis buffer [30 mM Tris/HCl, pH 7.5, 150 mM NaCl, 2 mM EDTA, 1 mM phenyhnethylsulfonyl fluoride (PMSF), protease inhibitors cocktail (Roche, Mannheim, Germany), 1% Triton X-100 and 10% glycerol] on ice for 30 minutes and clarified by centrifugation at 12000 rpm for 30 minutes at 4° C. The supernatants, normalized for protein concentration, were immunoprecipitated with 2 µg of H-130 DR-4 antibody on a roto shaker at 4° C. for 4 hours followed by the addition of 25 µL of 50% slurry of Protein A/G (Amersham, Piscataway, N.J.) beads for another 2 hours. The beads were washed thrice with lysis buffer and the complex was separated from the beads by boiling it in SDS lysis buffer for 5 minutes. The eluate was subjected to SDS-PAGE using a 12% gel for subsequent Immunoblot analysis.

Western blot analysis—The membranes were blocked with 5% milk (for coimmunoprecipitation assays) or 2% BSA (for DISC analysis) in PBS with 0.5% Tween 20 for one hour and the primary and secondary antibodies were incubated in PBST with 5% milk. The primary antibodies were used at concentrations of 1 µg/mL and the secondary antibodies at a concentration of 1:2000 to 1:10,000. All blots were developed using the ECL plus kit from Amersham following manufacturer's protocol Cell culture—HeLa and PA-1 cells were grown in DMEM (Gibco BRL, Rockville, Md.) supplemented with 10% fetal calf serum, L-glutamine (2 mM) and penicillin (100 units/mL)/streptomycin (100 µg/mL). To study the effects of CM, the regular growth medium was replaced with spent medium obtained from different cell cultures as indicated under a given experiment.

γ-irradiation—HeLa cells were harvested by trypsinization and irradiated in tubes. Cells were then plated at an initial density of 10$^6$ cells per p100 plate (PA-1 cells were plated at 2×10$^6$ cells per p100 plate) and replenished with fresh culture medium. Cells were allowed to grow for 2 weeks after which they were fixed with ice-cold methanol and stained with crystal violet to observe the outgrowth.

TRAIL treatment—PA-1 cells were plated in 6 well dishes (5×10$^5$ cells/plate). Next day cells were treated in situ with 50 ng/mL of 1 mL/well TRAIL (Peprotech, Rocky Hill, N.J.) for 3 hours. Cells were then assayed for levels of active caspase 3 as an indicator of apoptosis.

Active Caspase 3 assay—Cells were harvested, washed once with PBS and then fixed in Cytofix/Cytoperm solution and washed with Perm/Wash buffer as suggested by the manufacturer (Pharmingen, San Diego, Calif.). Cells were then stained with PE-conjugated rabbit antiactive caspase 3 antibodies according to the manufacturer's protocol (Pharmingen, San Diego, Calif.). The cells were then subjected to FACS analysis to determine the percentage of cells positive for active caspase 3.

Staining for mitotic Cells—PA-1 cells were plated (5×10$^5$/p100). Next day, growth medium was replaced with either fresh medium or conditioned media from control, HeLa IG20 or HeLa DENN-SV cells. Twenty-four hours later, cells were fixed with ice-cold methanol, washed 3 times and stained with DAPI (1 µg/mL, Sigma, St. Louis, Mo.) in order to visualize mitotic cells.

CFSE staining of cells—Cells were stained with 2 µM CFSE (Molecular Probes, Eugene, Oreg.) in situ (1 mL PBS/well (12 well plate)) for 10 minutes at 37° C., washed 3 times with PBS and replenished with new media Cells were harvested 48 or 72 hours later and analyzed using a BD FACS-Calibur equipped with CellQuest software. In the case of PA-1 cells, cells were stained in p100 plates as directed above (5×10$^5$ (cells/plate).

Cell cycle staining—PA-1 cells (p100 plate) were harvested and washed in PBS 3 times. Cells were then treated with ice-cold 70% ethanol for 30 minutes on ice and washed with PBS+2% FCS2 times and blocked for 10 minutes at room temperature with PBS+2% FCS. PBScontaining PI (40 ug/mL, Sigma, St. Louis, Mo.) and RNAse A (20 ug/mL, Roche, Indianapolis, Ind.) was used to resuspend washed cells. Finally the cells were incubated at 37° C. for 5 minutes before the analysis using a FACScalibur. Data were analyzed using Cell Quest and ModFit software.

Mpm2 staining—Cells were harvested, washed once with PBS and then fixed in Cytofix/Cytoperm solution and washed with Perm/Wash buffer as suggested by the manufacturer (Pharmingen, San Diego, Calif.). Cells were blocked with 2% FCS at RT for 15 minutes, and then stained with a mouse anti-mpm2 antibody (provided by Ig or Roninson. University of Illinois at Chicago) for 1 hour and then washed 2× in PBS+2% FCS. The mpm2 antibody recognizes a phosphorylated epitope (S/T) P found in phosphoproteins such as MAP2, HSP70, cdc25 and DNA topoisomerase II, most of which are phosphorylated at the onset of mitosis. The anti-Mpm2 binding was detected using an anti-mouse PE-conjugated secondary antibody (1/100 dilution: Caltag, Burlingame, Calif.) for 30 minutes. After 2 washes the cells were analyzed using a FACS calibur.

Luciferase Assay—Measurement of NF-κB activation was performed using the Dual-Luciferase AssaySystem (Promega, Madison, Wis.) as outlined in the manufacturer's protocol. Briefly, cells were plated in 12 well dishes (5×10$^5$ PA-1 cells/plate) and 18-24 hours later they were co-transfected with 0.01 µg/well of NF-κB firefly luciferase reporter construct and 0.001 µg/well renilla luciferase vector pRL-SV40. The constitutively expressing renilla luciferase vector was used to normalize for transfection efficiency. Cells were allowed to recover for 24 hours after which they were fed with serum free culture medium. The next day, cells were washed and lysed in situ for 30 minutes with gentle agitation using the manufacturer's lysis buffer. 20 µL of each lysate was then used to test for the levels of firefly luciferase activity and normalized to the levels of renilla luciferase activity. Since firefly and renilla luciferase fluoresce at different wavelengths, their emissions may be read from the same sample.

Multiplex assay for cytokines in conditioned media—Multiplex analysis was performed using multiplexed kits purchased from BioSourceinternational (Camarillo, Calif.) according to the manufacturer's protocol. The assays were performed in 96-well microplate format. A filter-bottom 96-well microplate (Millipore) was blocked for 10 min with PBS/BSA. To generate a standard curve, serial dilutions of appropriate standards provided by the manufacturer were prepared and used. Prepared standards and conditioned media were (50 µl/well) mixed with 50 µl of bead mixture in duplicate in the wells of a microtiter plate, and incubated for 1 h at room temperature on shaker. Wells were then washed three times with washing buffer using a vacuum manifold. PE-conjugated secondary antibodies were added to the appropriate wells and incubated for 45 min in the dark with constant shaking. Wells were washed twice, assay buffer was added to each well and samples were analyzed using the Bio-Plex suspension array system, which includes a fluorescence reader and Bio-Plex Manager analytical software (Bio-Rad Laboratories, Hercules, Calif.). Data analysis was done using five parametric-curve fitting.

Supernatants from confluent HeLa vector controls and HeLa IG20 cells were tested for the amounts of various cytokines as described in Materials and Methods and concentrations of various cytokines are expressed as pg/mL. ND denotes cytokines not detected.

IL6 ELISA—HeLa cells ($5 \times 10^5$) were plated in p100 petri dishes in serum free or serum containing media 4 days later, supernatants (conditioned media) were harvested, diluted (1/10) and assayed for the presence of IL-6 cytokine using a human IL-6 ELISA kit (BioSourceInternational, Camarillo, Calif.) as outlined by the manufacturer.

IL-6 neutralization—PA-1 cells were plated at $5 \times 10^5/12$ well plate. Next day, media from the PA-1 cells were replaced with 1 mL CM from HeLa IG20, HeLa DENN-SV or control cells alone or along with an IL-6 neutralizing antibody (50 µg/mL, Biosource, Camarillo, Calif.). 48 hours later, cells were harvested and counted.

Documents Cited

The following document is incorporated by reference to the extent it relates to protocols used in this disclosure.

Al-Zoubi A M, Efimova E V, Kaithamana S, Martinez O, El-Azami El-Idrissi M, Dogan R E, Prabhakar B S Contrasting Effects of IG20 and Its Isoforms, MADD and DENN-SV, on Tumor Necrosis Factor α-induced Apoptosis and Activation of Caspase 8 and -3 *J. Biol. Chem.* 276 (50): 47202-47211, 2001.

The invention claimed is:

1. A method to increase cancer cell death by modulating expression of human splice variants of IG20 in the cell, the method comprising decreasing cell replication by administering siRNA to a cancer cell, wherein the siRNA is configured to knock down a splice variant with a nucleic acid sequence selected from the group consisting of SEQ ID NO: 13, and both SEQ ID NOS: 13 and 14, in the cell, and wherein not all isoforms of IG20 present in non-cancerous cells are knocked down.

2. The method of claim 1, further administering chemotherapy to the cancer cell.

3. The method of claim 1, further comprising increasing cancer cell death and slowing cancer cell growth by increasing the expression of splice variant IG20pa.

* * * * *